United States Patent [19]

Danho et al.

[11] Patent Number: 5,128,448
[45] Date of Patent: Jul. 7, 1992

[54] CCK ANALOGS WITH APPETITE REGULATING ACTIVITY

[75] Inventors: Waleed Danho, Wayne; David J. Nelson, Nutley; Gary L. Olson, Westfield; Shian-Jan Shiuey, Nutley; Jefferson W. Tilley, North Caldwell, all of N.J.; Rolf Wagner, Waukegan, Ill.

[73] Assignee: Hoffman-La Roche Inc., Nutley, N.J.

[21] Appl. No.: 463,212

[22] Filed: Jan. 10, 1990

[51] Int. Cl.$^5$ .............................. C07K 7/06; C07K 7/64; A61K 37/02
[52] U.S. Cl. ........................... 530/329; 530/317; 530/330
[58] Field of Search ............... 530/317, 329, 330; 514/16, 17, 18

[56] References Cited

FOREIGN PATENT DOCUMENTS 0248440 6/1987 European Pat. Off. .
0339549 4/1989 European Pat. Off. .

OTHER PUBLICATIONS

Schick et al., Biological abstracts, vol. 82(8), 1986 BA:76466.
Gourch et al., Biological Abstracts vol. 89(9), 1990, BA:97018.

Primary Examiner—Lester L. Lee
Assistant Examiner—Avis Davenport
Attorney, Agent, or Firm—George M. Gould; William H. Epstein; Bruce A. Pokras

[57] ABSTRACT

The invention is directed to novel CCK analogs wherein Tryptophan and/or Phenylalamine are substituted with a radical which provides enhanced appetite suppressant activity to the peptide.

47 Claims, No Drawings

CCK ANALOGS WITH APPETITE REGULATING ACTIVITY

BACKGROUND OF INVENTION

Peptides are ubiquitous biological molecules and have, in recent years, become the subject of extensive research and investigation. For example, the possibilities for utilizing natural biological substances, such as peptides, as therapeutics for various disease states is being aggressively explored.

Elucidation of the amino acid sequences of such peptides such as Growth Hormone, Growth Hormone Releasing Factor, or Cholecystokinin (CCK) has lead to advancements in the understanding of how these molecules work in treating various disorders. However, peptides are generally poorly adsorbed and suffer from rapid degradation upon exposure to peptidases often resulting in low bioavailability. It has been recently discovered that in many instances if the amino acid constituency of many naturally occurring peptides is altered by single or multiple amino acid substitutions at different sites, the analogs of the natural peptide may have better bioavailability or degrade less rapidly and hence exhibit greater efficacy.

For example, CCK is a family of peptide hormones which vary in length up to 58 amino acids. The sequence of CCK first isolated contained 33 amino acids (CCK-33). CCK-33 as well as fragments thereof, such as CCK-8 and Acetyl-CCK-7, have been shown to have satietyinducing effects when administered peripherally to animals. CCK-8 has the amino acid sequence:

$$Asp^{26}\text{-}Tyr\text{-}(SO_3H)^{27}\text{-}Met^{28}\text{-}Gly^{29}\text{-}Trp^{30}\text{-}Met^{31}\text{-}Asp^{32}\text{-}Phe^{33}\text{-}NH_2.$$

CCK-7 lacks the amino acid Asp in position 26.

While CCK analogs are known to have satiety inducing effects, they are not selective and also exhibit low bioavailability. This has led to the synthesis of various CCK analogs wherein the attempt to improve properties such as stability and bioavailability has been made. A multitude of CCK analogs with various amino acid substitutions have yielded compounds with altered properties which enhance their potential usefulness in human therapeutics.

SUMMARY OF THE INVENTION

The invention is directed to compounds selected from the group consisting of:

I(a) X-Tyr(SO$_3$H)-Met-Gly-Trp-Met-Asp-R$^1$-NH$_2$
I(b) X-Tyr(SO$_3$H)-Met-Gly-R$^2$-Met-Asp-Phe-NH$_2$
I(c) X-Tyr(SO$_3$H)-Met-Gly-R$^2$-Met-Asp-R$^3$-NH$_2$
I(d) R$^7$-Met-Gly-Trp-Met-Asp-R$^3$-NH$_2$

wherein
R$^1$ is a radical of the formula:

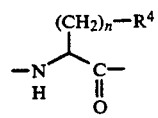

R$^2$ is a radical of the formula:

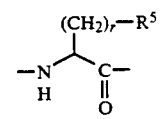

R$^3$ is a radical of the formula:

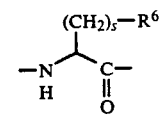

R$^4$ is a substituted or unsubstituted C$_5$ or C$_{7-12}$ mono or polycyclic alkyl where the substitutent is C$_{1-7}$ alkyl; C$_{4-15}$ linear or branched chain alkyl; tetrahydronaphthyl; or naphthyl.

R$^5$ is a substituted phenyl where the substituents are selected from the group consisting of C$_{1-7}$ alkyl, C$_{1-7}$ alkoxy, or halogen; benzothiophenyl; quinolinyl; tetrahydronaphthyl; or substituted or unsubstituted naphthyl with the substituents selected from the groups consisting of halogen, C$_{1-7}$ alkyl, or C$_{1-7}$ alkoxy.

R$^6$ is a substituted or unsubstituted C$_{5-12}$ mono or polycyclic alkyl where the substitutent is C$_{1-7}$ alkyl; C$_{4-15}$ linear or branched chain alkyl; tetrahydronaphthyl; or substituted or unsubstituted naphthyl with the substituents selected from the groups consisting of halogen, C$_{1-7}$ alkyl, or C$_{1-7}$ alkoxy.

R$^7$ is

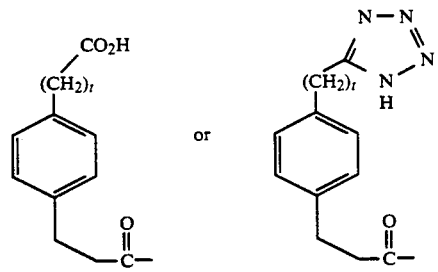

n is an integer from 1-3
r is an integer from 1-3
s is an integer from 1-3
t is an integer from 0-2
X is C$_{1-7}$ alkanoyl or C$_{1-7}$ alkoxy carbonyl.

The invention is also directed to a method for regulating appetite in subjects comprising administering a therapeutically effective amount of the compound of claim 1 or its pharmaceutically acceptable salts.

DETAILED DESCRIPTION

With respect to all of compounds I(a)-(c) it is preferred that X=Ac (acetyl). Also included within the scope of the instant claims are when X-Tyr(SO$_3$H) is substituted with desaminotyrosine sulfate. All compounds I(a)-(c) wherein the X-Tyr(SO$_3$H) moiety is substituted with desaminotyrosine sulfate are included within the scope of the invention.

With respect to Compound I(a) R$^4$ may be preferably a substituted or unsubstituted C$_5$ or C$_{7-12}$ mono or polycyclic alkyl where the substituent is C$_{1-7}$ alkyl; a C$_{4-15}$ linear or branched chain alkyl; tetrahydronaphthyl; or naphthyl. When R⁴ is substituted or unsubstituted C₅ cyclic alkyl, preferred is where:
R⁴ is a substituted or unsubstituted cyclopentyl and n=1, said compound having the formula:

When R⁴ is a C₄₋₁₅ linear or branched chain alkyl and particularly preferred is where:
R⁴ is tert.-butyl and n=1, said compound having the formula

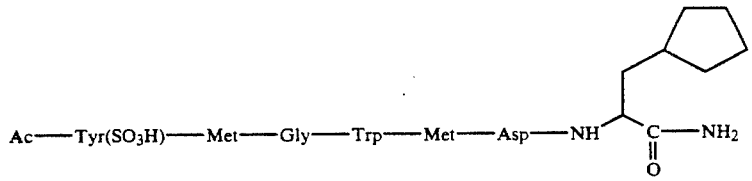

When R⁴ is a substituted or unsubstituted C₇₋₁₂ mono or polycyclic alkyl, particularly preferred is where:
R⁴ is cyclooctyl and n=1, said compound having the formula:

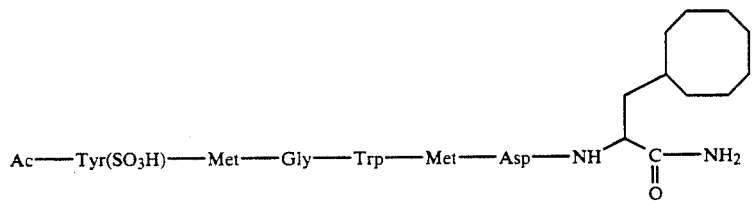

R⁴ is 2-adamantyl and n=1, said compound having the formula

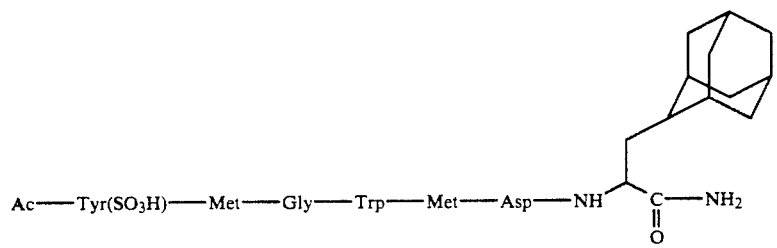

R⁴ is cyclohexyl and n=2, said compound having the formula:

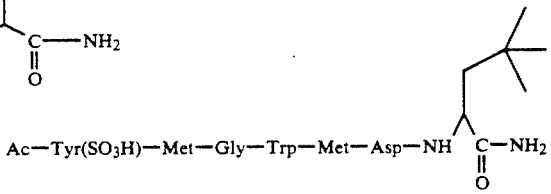

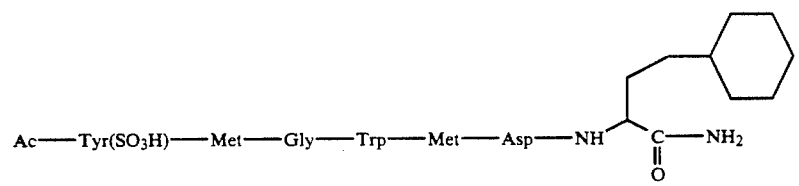

R⁴ is trans-4-tert-butylcyclohexyl and n=1, said compound having the formula

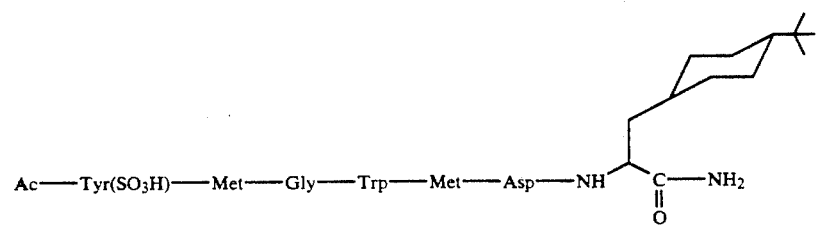

$R^4$ is decyl and n=2, said compound having the formula

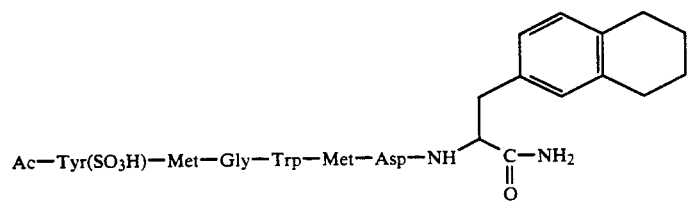

When $R^4$ is tetrahydronaphthyl, particularly preferred is where:
$R^4$ is 5,6,7,8-tetrahydro-2-naphthyl and n=1, said compound having the formula:

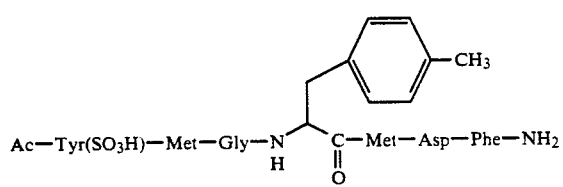

With respect to Compound I(b), $R^5$ may be a substituted phenyl wherein the substituents are selected from the group consisting of $C_{1-7}$ alkyl, $C_{1-7}$ alkoxy, or halogen; benzothiophenyl; quinolinyl; tetrahydronaphthyl; or substituted or unsubstituted naphthyl with the substituents selected from the group consisting of halogen, $C_{1-7}$ alkyl, or $C_{1-7}$ alkoxy.

When $R^5$ is a substituted phenyl with the substituents selected from the group consisting of $C_{1-7}$ alkyl, $C_{1-7}$ alkoxy, or halogen, preferred is where:
$R^5$ is 4-methylphenyl and r=1, said compound having the formula:

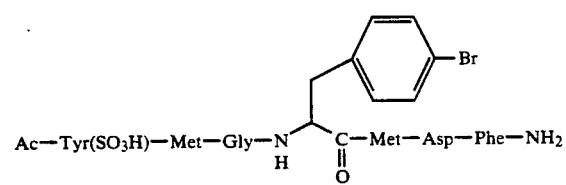

$R^5$ is 4-bromophenyl and r=1, said compound having the formula:

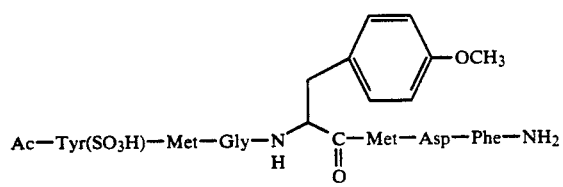

$R^5$ is 4-methoxyphenyl and r=1, said compound having the formula

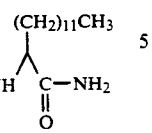

$R^5$ is 3-methylphenyl and r=1, said compound having the formula:

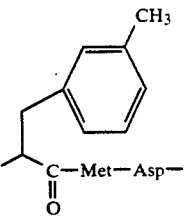

$R^5$ is 4-propylphenyl and r=1, said compound having the formula:

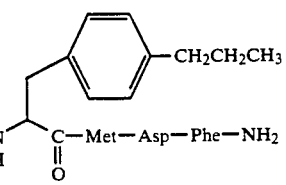

Where $R^5$ is quinolinyl, preferred is where:
$R^5$ is 3-quinolinyl and r=1, said compound having the formula:

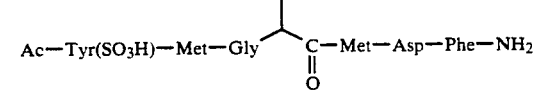

When $R^5$ is tetrahydronaphthyl, particularly preferred is where:
$R^5$ is 5,6,7,8-tetrahydro-2-naphthyl and r=1, said compound having the formula:

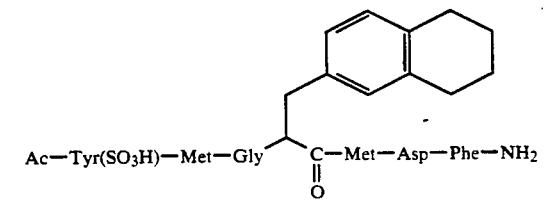

When $R^5$ is benzothiophenyl and particularly preferred is where:
$R^5$ is 2-benzo[b]thiophenyl and r=1, said compound having the formula:

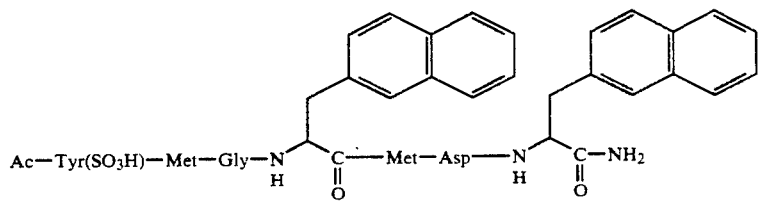

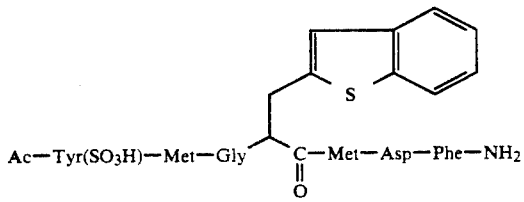

With respect to Compound I(c) $R^5$ is as set forth above and $R^6$ may be a $C_{4-12}$ linear or branched chain alkyl; a substituted or unsubstituted $C_{5-12}$ mono or polycyclic alkyl where the substituent is $C_{1-7}$ alkyl; $C_{4-15}$ linear or branched chain alkyl; tetrahydronaphthyl; or substituted or unsubstituted naphthyl with the substituents selected from the group consisting of halogen, $C_{1-7}$ alkyl, or $C_{1-7}$ alkoxy. Preferred is where $R^5$ is a substituted or unsubstituted naphthyl where the substituents are selected from the group consisting of $C_{1-7}$ alkyl, or $C_{1-7}$ alkoxy and $R^6$ is a substituted or unsubstituted naphthyl with the substituents selected from the group consisting of halogen, $C_{1-7}$ alkyl, or $C_{1-7}$ alkoxy; or a substituted or unsubstituted $C_{5-12}$ mono or polycyclic alkyl where the substituent is $C_{1-7}$ alkyl.

More preferred is where $R^5$ is 2-naphthyl and $R^6$ is a $C_{5-12}$ mono or polycyclic alkyl wherein the substituent is $C_{1-7}$ alkyl.

Particularly preferred is:
wherein $R^5$ is 2-naphthyl, $R^6$ is cyclohexyl, $r=1$ and $s=1$, said compound having the formula:

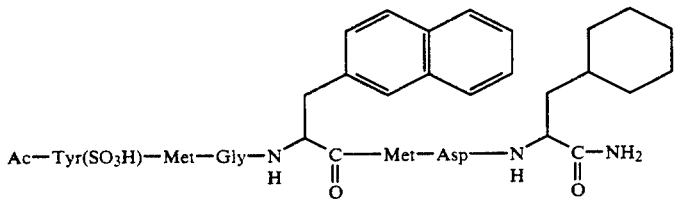

wherein $R^5$ is 2-naphthyl, $R^6$ is cyclooctyl, $r=1$ and $s=1$, said compound having the formula:

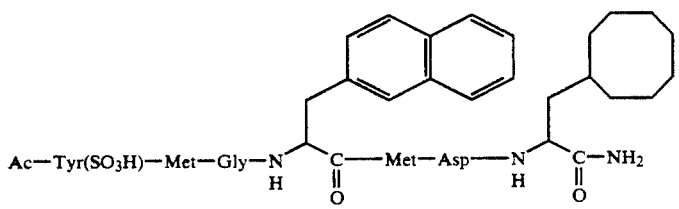

Also preferred is wherein $R^5$ is 2-naphthyl and $R^6$ is a substituted or unsubstituted naphthyl where the substituents are selected from the group consisting of halogen, $C_{1-7}$ alkyl, or $C_{1-7}$ alkoxy, and particularly preferred is where $R^6$ is 2-naphthyl and $r$ and $s=1$, said compound having the formula:

With respect to compounds I(d) and I(e), $R^6$ may be a substituted or unsubstituted $C_{5-12}$ mono or polycyclic alkyl where the substituent is $C_{1-7}$ alkyl; $C_{4-15}$ linear or branched chain alkyl; tetrahydronaphthyl; or substituted or unsubstituted naphthyl with the substituents selected from the group consisting of halogen, $C_{1-7}$ alkyl, or alkoxy.

Preferably $R^6$ is a substituted or unsubstituted $C_{5-12}$ mono or polycyclic alkyl where the substituent is $C_{1-7}$ alkyl.

More preferred is:
where $R^6$ is cyclohexyl or cyclooctyl and $R^7$ is:

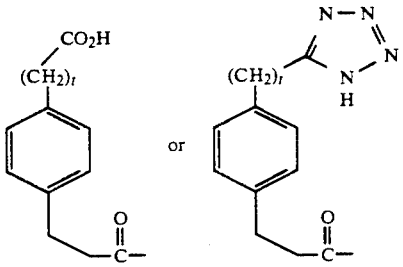

Particularly preferred are the compounds having the formula:

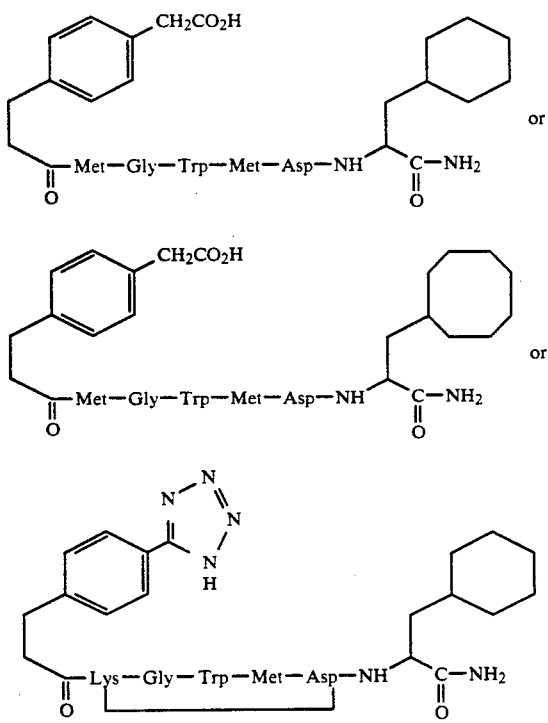

Amino acid substitutions in polypeptides which do not essentially alter their biological activities are known in the art and described, e.g., by H. Neurath and R. L. Hill in "The Proteins", Academic Press, New York (1979). The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and vice versa. The compounds of the invention include such substitutions.

Particularly, the amino acids, Met and Nle are interchangeable so that where the amino acid Met in any peptide of the invention may be substituted by Nle without any significant change in activity. The invention is intended to cover all peptides with substitutions which do not essentially alter the character of the peptides.

The invention is also directed to a method of regulating appetite in a subject comprising administering a therapeutically effective amount of the compound of claim 1 or its pharmaceutically acceptable salts.

A "therapeutically effective amount" as used herein refers to the amount of the peptide (on a weight basis) per kg. of body weight of the subject which must be administered to suppress appetite. It is well within the skill of the art to calculate such amounts considering the method of administration, the particular subject and the weight of the subject. See Morley, J. E. "Minireview. The Ascent of Cholecystokinin (CCK) from Gut to Brain" *Life Sciences*, 1982, 30, 479.

The analogs of the invention may be administered to the subject by any suitable route including, nasal, sublingual, buccal, intraperitoneal, or parenteral including intravenous, intramuscular, or transdermal. The analogs may be administered as water soluble salts, generally as salts of alkaline metals such as sodium or potassium salts, as amine salts, preferably ammonium salts, or as acid addition salts. The analogs of the invention can be converted to the pharmaceutically acceptable salts by known methods.

If the analogs of the invention are administered intranasally such vehicles of administration may include foams, creams, inhalants, etc. The effective appetite suppressing amount of the analog as the active ingredient is dissolved in pharmaceutically acceptable foams or inhalant compositions suitable for intranasal administration, which compositions are known to those skilled in the art.

Where the peptides of the invention are administered parenterally, or intraperitoneally the appropriate amount of the analog as the active ingredient is dissolved in sterile injectable solutions or suspensions. These types or solutions are well known to skilled artisans and comprise for example saline solutions, etc.

PREPARATION OF THE ANALOGS OF THE INVENTION

The protected amino acids required as intermediates for the synthesis of the compounds of the invention are either known compounds or can be prepared by methods generally known to those skilled in the art. While many synthetic approaches to chiral protected amino acids suitable for use in solid phase peptide synthesis have been described lately, the methodology described by Evans and his coworkers (D. A. Evans and T. C. Britton, *J. Am. Chem. Soc.* 1987, 109, 6881; D. A. Evans, T. C. Britton, R. L. Dorow and J. F. Dellaria, *Tetrahedron* 1988, 44, 5525; D. A. Evans and J. A. Ellman, *J. Am. Chem. Soc* . 1989, 111, 1063) is particularly convenient for preparation of intermediates required for the synthesis of the compounds of this invention.

In brief, an acetic acid derivative such as compound 1 is converted to an acid halide or a mixed anhydride using standard methodology and is reacted with a metal salt, for example the lithium salt, of a chiral oxazolidinone derivative such as 2 to give a chiral intermediate 3. Azidation is then effected by formation of the potassium enolate derivative of 3 at low temperature, for example at −78° C. in an inert solvent, for example THF, and quenching with a low temperature solution of 2,4,6-triisopropylphenylsulfonyl azide followed by treatment with acetic acid and warming to give an azide derivative such as 4. The resulting compound 4 can be formed in high diastereomeric purity by this technique depending on the nature of R$^1$ and the stereochemistry of the oxazolidinone 2. When R$^1$ is for example benzyl, a diastereomeric excesse of greater than 95% is readily attained. This compound can either be hydrolyzed to give an azidoacid which in turn can be reduced by conventional means to the desired amino acid, or preferably it can be reduced catalytically for example using hydrogen in the presence of palladium on carbon and an excess of di-tert-butyl dicarbonate to give a Boc protected amino derivative such as 5. Hydrolysis with a suitable base, for example lithium hydroxide or preferably, lithium hydroperoxide, then leads to the protected amino acid derivative 6. Alternatively, the potassium enolate derived from 3 can be trapped with di-tert-butyl-azodicarboxylate to give a bis-(tert-butoxycarbonyl)hydrazine 7. This material provides an alternative source of the amino acid 6 by hydrolytic removal of the oxazolidinone group as above followed by treatment with an appropriate acid, for example trifluoroacetic acid, to remove the butoxycarbonyl groups, catalytic hydrogenation for example over Raney nickel, to form the amino acid 8 and finally amino group protection, for example by treatment with di-tert-butyl dicarbonate to give 6. Suitable variations on these procedures could be used to prepare analogous amino acids with different nitrogen protecting groups.

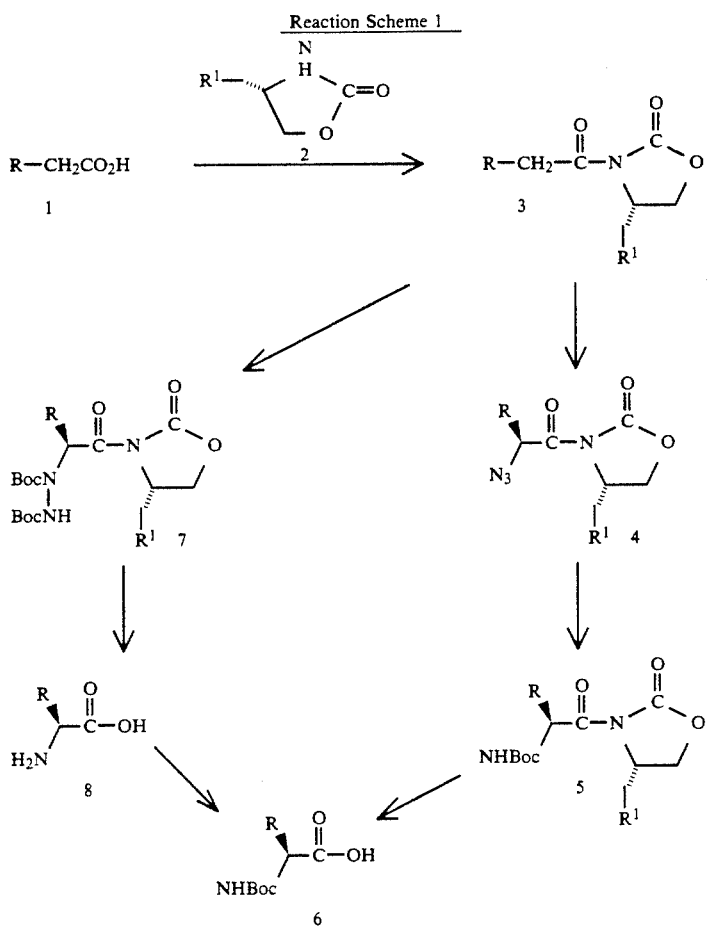

Reaction Scheme 1

R is a straight or branched chain alkyl group optionally substituted by substituted or unsubstituted aryl, a mono or bicyclic heteroaromatic ring, naphthyl or partially hydrogenated naphthyl, or a optionally substituted mono or polycyclic alkyl group.

$R^1$ is a branched chain alkyl or benzyl

The peptides of the invention may be prepared using solid phase synthesis by the method generally described by Merrifield, *J. Am. Chem. Soc.*, 1963 85, 2149, although other equivalent chemical syntheses known in the art may also be used. Solid-phase synthesis is commenced from the C-terminal end of the peptide by coupling a protected a-amino acid by an amide bond to a suitable resin, e.g., benzhydrylamine (BHA), methylbenzhydrylamine (MBHA), 4-(oxymethyl)-phenylacetamidomethyl (PAM) or 5-[(2' or 4')-aminomethyl-3',5'-dimethoxyphenoxy]valerate (PAL). BHA, MBHA, PAM and PAL resin supports are commercially available.

In solid phase synthesis methods, the reactive side chain groups of the various amino acid moieties are typically protected with suitable protecting groups which will prevent a chemical reaction from occurring at that site until the protecting group is ultimately removed. While specific protecting groups are disclosed in regard to the solid phase synthesis aspect, it should be noted that each amino acid can be protected by any protective groups conventionally used for the respective amino acids in solution phase synthesis.

For the synthesis of the protected amino acids used as intermediates (Examples 1-69), all reactions were performed under an argon atmosphere. Melting points were taken on a Thomas-Hoover apparatus and are uncorrected. Optical rotations were determined with a Perkin-Elmer model 141 polarimeter. $^1$H-NMR spectra were recorded with Varian XL-200 and XL-400 spectrometers, using tetramethylsilane (TMS) as internal standard. IR spectra were recorded on a Beckman IR-9 or IR-12 spectrophotometer. Electron impact (EI, 70 ev) and fast atom bombardment (FAB) mass spectra were taken on VG ZAB-1F or VG 7070E-HF mass spectrometers. Combustion analysis were performed on TLC homogeneous or recrystallized samples. In all cases, the physicalchemical data were consistent with the assigned structures. Flash silica gel chromatography employed Kiesel gel 60, 230-400 mesh, as supplied by E. Merck, Darmstadt under a nitrogen pressure of 2-5 psi. Concentration refers to removal of solvent under aspirator pressure using a Buchi rotary evaporator. Solvents were commercially available reagent grade as obtained from Fisher Scientific; anhydrous THF was freshly distilled over sodiumbenzophenone ketyl; anhydrous DMF was obtained by distillation from $CaH_2$. TLC was carried out using kieselgel 60 $F_{254}$ plates as supplied by E. Merck, Darmstadt, and were visualised with 254 nm light, 0.3% ninhydrin in n-butanol containing 3% acetic acid or 10% phosphomolybdic acid in methanol.

To determine the enantiomeric purities of aminoacid derivatives prepared as described herein, a 1 mg sample of the test substance was dissolved in 0.5 mL of 6N HCl and sealed under vacuum. The vial was heated at 110° C. for 18 hrs and allowed to cool. The hydrolysate was concentrated to dryness and then heated in a sealed reaction vessel in 3N HCl in isopropanol for 1 hr at 110° C. The reaction mixture was evaporated to dryness and dissolved in 0.3 mL of ethyl acetate and 0.2 mL of pentafluoropropionic anhydride. After heating in a sealed reaction vessel for 10 min at 150° C., the solvent and excess reagent was evaporated under a stream of nitrogen. The residue was dissolved in 1.0 mL of $CH_2Cl_2$ and was analyzed by gas chromatography on a Hewlett-Packard 5710A instrument equipped with a 50M X 0.28 mm Chirasil-Val III capillary column. The column temperature was programmed from 90° C. to 200° C. at a rate of 4° C./min using hydrogen as the carrier gas and FID detection.

For the synthesis of the peptides of the invention (Examples 70–94), all solvents used in the preparations described herein, e.g. methylene chloride ($CH_2Cl_2$), 2-propanol, and dimethylformamide (DMF), methanol, were Burdick and Jackson "distilled in glass" grade and used without additional distillation. Trifluoroacetic acid (TFA), diisopropylethylamine (DIPEA, piperidine (PIP), dicyclohexylcarbondiimide (DCC), 1-hydroxybenzotriazole (HOBt), and [benzotriazole-1-yl-oxytris(dimethyl)phosphonium hexafluorophosphate] (BOP) were purchased from Chemical Dynamics Corp. and were sequential grade purity. 1-2-ethanedithiol (EDT) was purchased from Sigma Chemical Co. and used without further purification. All protected amino acids were of the L-configuration unless otherwise indicated and were obtained from Bachem.

Purity of the protected amino acids was confirmed by thin layer chromatography (TLC), elemental analysis, IR, MS, NMR and optical rotation.

The following instrumentation was utilized. TLC was performed on glass backed precoated silica gel 60 $F_{254}$ plates purchased from E. Merck using appropriate solvent systems. Detection of spots was by UV fluorescence quenching (254 nm absorption), iodine staining, or ninhydrin spray for primary and secondary amines.

For amino acid analyses, peptides were hydrolyzed in 6N HCl containing phenol at 115° C. for 24 hours in evacuated Reacti-Therm hydrolysis tubes. Analyses were performed on a Beckman 121M amino acid analyzer.

High pressure liquid chromatography (HPLC) was conducted on an LDC apparatus consisting of a Constametric I pump, a Constametric III pump, a Gradient Master solvent programmer and mixer, and a Spectromonitor III variable wavelength UV detector. Analytical HPLC chromatography was performed on reversed phase with Waters Micro Bondapack C-18 columns (0.4×25) cm. Preparative HPLC separations were run on (2.5×50) cm Partisil M20 10/50 ODS-3 column, or (2.3×30) cm micro Bondapack C-18 column; in both cases, a pre-column of Whatman Co:Pell ODS pellicular packing was used. The peptides were assembled in a stepwise manner on a solid support using a Vega 1000 peptide synthesizer. The Vega 1000 peptide synthesizer was controlled by an Apple IIe microprocessor with manual operations at steps 16 and 20 for the Boc-protocol and 7 and 10 for the Fmoc-protocol.

The protocol for a typical Boc-synthetic cycle was as follows:

| Step | Reagent | Time |
| --- | --- | --- |
| 1 | 1% EDT/$CH_2Cl_2$ | 1 × 30 sec. |
| 2 | 50% TFA/$CH_2Cl_2$/w 1% EDT | 1 × 1 min. |
| 3 | Repeat Step 1 | |
| 4 | 50% TFA/$CH_2Cl_2$/w 1% EDT | 1 × 15 min. |
| 5 | $CH_2Cl_2$ | 1 × 30 sec. |
| 6 | Methanol | 1 × 30 sec. |
| 7–8 | Repeat steps 5 and 6 | |
| 9 | $CH_2Cl_2$ | 2 × 30 sec. |
| 10 | 8% DIPEA | 2 × 2 min. |
| 11–15 | Repeat step 5–9 | |
| 16 | 3 equiv. Boc-AA, DCC, HOBt | 1 × 60 min. |
| 17 | 1% DIPEA | 1 × 30 min. |
| 18–19 | Repeat steps 6 and 9 | |
| 20–21 | Repeat steps 16 and 17 if Kaiser test is positive | |
| 22 | Methanol | 1 × 30 sec. |
| 23–24 | Repeat steps 5 and 6 | |
| 25 | $CH_2Cl_2$ | 1 × 30 sec. |
| 26 | Methanol | 2 × 30 sec. |
| 27 | $CH_2Cl_2$ | 3 × 30 sec. |

The protocol for a typical Fmoc-synthetic cycle was as follows:

| Step | Reagent | Time |
| --- | --- | --- |
| 1 | 20% piperidine/DMF | 1 × 5 min. |
| 2 | 20% piperidine/DMF | 1 × 5 min. |
| 3 | DMF | 2 × 1 min. |
| 4 | $CH_2Cl_2$ | 2 × 1 min. |
| 5 | 2-propanol | 2 × 1 min. |
| 6 | $CH_2Cl_2$/DMF | 2 × 1 min. |
| 7 | 3 equiv. Fmoc-AA,DCC,HOBt | 1 × 60 min. |
| 8 | $CH_2Cl_2$ | 2 × 1 min. |
| 9 | DMF | 2 × 1 min. |
| 10–12 | Repeat steps 7,8,9 if Kaiser test is positive | |
| 13 | $CH_2Cl_2$ | 2 × 1 min. |
| 14 | DMF | 2 × 1 min. |
| 15 | 2-propanol | 2 × 1 min. |
| 16 | DMF | 2 × 1 min. |

Solvents for all washings and couplings were measured to volumes of 10–20 mL/g resin. Couplings were performed using the DCC/HOBt procedure. Coupling reactions were monitored by the Kaiser ninhydrin test to determine whether coupling was complete at step 19 by the Boc-synthetic protocol or at step 9 by the Fmoc-synthetic protocol as set forth by Kaiser et al., *Analytical Biochemistry* 1970, 34, 595–598.

The fully assembled peptide-resins were dried under high vacuum overnight. For the Boc-synthesis the modified procedures of Tam et al. *Tetrahedron Letters*, 1982, 23, 4425–4438 were used. In brief: The peptide-resin was treated in a teflon HF apparatus (Peninsula) with HF, dimethylsulfide and anisol (5:13:2) for 1h at 0° C. After evaporation to a low volume fresh anhydrous HF was distilled into the reaction vessel (18 mL) for second treatment for 1.5h at 0° C. After thorough evaporation, the dry resin was washed with 3 volumes each of $Et_2O$ and EtOAc, then triturated with 4×15 mL of 30% acetic acid and filtered. Lyophilization of the aqueous filtrate yielded the crude peptide.

For the Fmoc-synthesis the procedure of Barany et al., *Int. J. Pept. and Prot. Res.* 1987, 30, 206–216 was used. In brief: the peptide-resin was treated with TFA/CH$_2$Cl$_2$/EDT (14/5/1) by volume for 1h at room temperature. The filtrate was collected and combined with further washes by TFA/CH$_2$Cl$_2$ (7:3), CH$_2$Cl$_2$ and TFA. These extracts were evaporated to dryness at 25° and the residue triturated with ether.

Preparative purification was carried out directly on the crude unsulfated peptide by HPLC on a (2.3×30) cm micro Bondapack C-18. The peptides were applied in a minimum volume of 50% AcOH, and eluted with a slow gradient (4 hr) of 5-65%, 0.022% TFA/CH$_3$CN, at a flow rate of 8.0 mL/min. Fractions were collected at 3 minute intervals and cuts were made after inspection by analytical HPLC. Fractions, judged to be greater than 97% pure, were pooled and lyophilized.

Purity of the individual peptides was checked by HPLC and determined to be 99% in all cases Amino acid analyses of the individual peptides were performed and the expected values were obtained in each case. U.V., N.M.R. and M.S. were also performed on the analogs confirming the chemical integrity of the peptides.

The sulfation procedure was as follows:

The sulfate-ester containing peptides were prepared by sulfation of the phenolic (tyrosine) group using pyridinium acetyl sulfate reagent. A typical sulfation was carried out as follows: 60-240 mg of pyridinium acetyl sulfate (PAS) was dissolved in 5% mL of pyridine and mixed at 60° C. for 10 minutes. N-acetyl-CCK-7 analog (10 mg) is dissolved in 5 mL of pyridine to which the PAS reagent is added. After stirring for 6 hours at room temperature, it is neutralized with 2 volumes 1.15M ammonium hydroxide, lyophilized and purified by HPLC.

The sulfated peptides were purified by preparative reverse phase HPLC on a C-18 10 m (ES Industries) (1.00×30) cm column using a 1 hour gradient (10-40%) of acetonitrile in 0.01M ammonium acetate with a flow rate of 6 mL/min and detection of 290 nm. Fractions pooling and peptide purity were determined by analytical HPLC using a Bondapack C-18, 10 micron Waters column (0.30×30) cm, and an acetonitrile in ammonium acetate gradient with a flow of 2 mL and detection at 215 nm.

The purity of the sulfated peptides was determined by analytical HPLC, amino acid analysis, UV and IR.

EXAMPLE 1

2-Propynoic acid phenylmethyl ester

To a stirring mixture of propiolic acid (1.79 mL (2.04 g), 28.65 mmol) and potassium carbonate (4.87 g, 35.2 mmol) in anhydrous DMF (40 mL) was added benzyl bromide (3.78 mL (5.43 g of 99% pure), 31.4 mmol). The reaction mixture was stirred at room temperature for 16 h. The resulting heterogeneous mixture was poured into 40 mL of H$_2$O and was extracted with ethyl ether (3×40 mL). The combined ether extracts were dried (Na$_2$SO$_4$). Filtration and concentration provided 12.16 g of crude product, which upon high vacuum distillation yielded 2-propynoic acid phenylmethyl ester (bp 60° C. 0.5 mm) as a clear oil (3.57 g, 22.3 mmol) in 78% yield.

EXAMPLE 2

3-(Tributylstannyl)-2-propenoic acid phenylmethyl ester

To a stirring mixture of 2-propynoic acid phenylmethyl ester (2.46 g, 15.4 mmol) and tributyltin hydride (3.89 mL, 14.9 mmol, 97% purity) was added 2,2'-azobisisobutyronitrile (99.4 mg) and the reaction mixture was slowly warmed to 65° C. After stirring for 8 h at 65° C., the cooled reaction mixture was purified by flash chromatography, eluting with a mixture of hexane and EtOAc (50:1) to give 3-(tributylstannyl)-2-propenoic acid phenylmethyl ester (4.80 g, 10.65 mmol) as a mixture of E and Z isomers, in 69% yield.

EXAMPLE 3

(E)-3-[4-(1,1-Dimethylethyl)phenyl]-2-propenoic acid phenylmethyl ester

To a mixture of 3-(tributylstannyl)-2-propenoic acid phenylmethyl ester (5.24 g, 11.6 mmol), 1-bromo-4-tert-butylbenzene (4.11 mL (5.05 g, 98% pure), 23.2 mmol) and lithium chloride (958 mg, 23.2 mmol) suspended in 26 mL of anhydrous DMF was added, ((C$_6$H$_5$)$_3$P)$_2$PdCl$_2$ (0.26 g, 0.37 mmol). The mixture was deoxygenated by bubbling argon through it for 35 minutes and then stirred at a bath temperature of 94° C. for 24 h. The brown reaction mixture was concentrated by evaporating most of DMF under vacuum and the brown residue was triturated with 50 mL of a mixture of CH$_2$Cl$_2$ and hexane (1/1). The resulting solid was separated by filtration and the crude brown product (9.7 g) was obtained by concentration of the filtrate to dryness (using an oil pump vacuum to remove last traces of DMF). The product was purified via flash chromatography, eluting with a mixture of CH$_2$Cl$_2$ and hexane (1/1) to give (E)-3-[4-(1,1-dimethylethyl)phenyl]-2-propenoic acid phenylmethyl ester (2.04 g, 6.93 mmol) in 60% yield, m.p. 59°-62° C.,

EXAMPLE 4

4-(1,1-Dimethylethyl)benzenepropanoic acid

A stirring solution of (E)-3-[4-(1,1-dimethylethyl)-phenyl]-2-propenoic acid phenylmethyl ester (2.04 g, 6.93 mmol) in 136 mL of abs. EtOH in the presence of 377 mg of 10% Pd/C was hydrogenated at room temperature at atmospheric pressure. After removing the catalyst by filtration through a pad of celite, the filtrate was concentrated to give 4-(1,1-dimethylethyl)benzene-propanoic acid, (1.39 g, 6.74 mmol) in 97% yield, m.p. 110°-113° C.

EXAMPLE 5

(S)-3-[3-[4-(1,1-Dimethylethyl)phenyl]-1-oxopropyl]-4-(phenylmethyl)-2-oxazolidinone To a stirring solution at −78° C. of 4-(1,1-dimethylethyl)benzenepropanoic acid (1.29 g, 6.25 mmol) and triethylamine (1.05 mL, 7.51 mmol) in dry THF (26 mL) was added pivaloylchloride (0.77 mL, 6.25 mmol) dropwise. After the addition, the mixture was stirred at −78° C. for 10 minutes and at 0° C. for 30 minutes. During this time metalated oxozolidinone was prepared separately by dropwise addition of n-butyl lithium (4.29 mL of a 1.6M solution in hexane) to a solution of (S)-(−)-4-benzyl-2-oxazolidinone (1.23 g of 99% pure, 6.88 mmol) in dry THF (26 mL). The metalated oxazolidinone solution was then added, at −78° C., via a cannula to the previously prepared reaction mixture and stirred for 1 h at 0° C. The reaction was quenched at 0° C. by addition of saturated NH$_4$Cl solution (16 mL) and was concentrated. Saturated NH$_4$Cl solution (25 mL) was added to the residue and the mixture was extracted with CH$_2$Cl$_2$ (3×100 mL). The combined organic phases were washed with saturated NaHCO$_3$ (100 mL) and dried (NaSO$_4$). Filtration and concentration provided crude product (2.50 g) which was purified via flash chromatography, eluting with a mixture of EtOAc and hexane (1:3) to provide (S)-3-[3-[4-(1,1-dimethylethyl)-phenyl]-1-oxopropyl]-4-(phenylmethyl)-2-oxazolidinone (1.82 g, 4.98 mmol) in 80% yield, mp 123°-126° C.

EXAMPLE 6

[4S-3-(2S)]-3-[2-azido-3-[4-(1,1-dimethylethyl)phenyl]-1-oxopropyl]-4-(phenylmethyl)-2-oxazolidinone Under anhydrous conditions, a precooled solution (−78° C.) of (S)-3-[3-[4-(1,1-dimethylethyl)phenyl]-1-oxopropyl]-4-(phenylmethyl)-2-oxazolidinone (1.075 g, 2.94 mmol) in dry THF (37 mL) was transferred via a cannula into a precooled solution (−78° C.) of potassium bis(trimethylsilyl) amide (12.7 mL of a 0.5M solution in toluene, 6.37 mmol) dissolved in dry THF (44 mL). The reaction mixture was stirred at −78° C. for 20 minutes. Then a precooled solution (−78° C.) of 2,4,6-triisopropylbenzenesulfonyl azide (2.35 g, 7.58 mmol) in dry THF (22 mL) was transferred via a cannula into the enolate solution. The mixture was stirred for 1 h at −78° C., was quenched with glacial acetic acid (0.764 mL) and was stirred at 30° C. for 2 h. Saturated NaHCO$_3$ solution (34 mL) was added and the mixture was concentrated. The residue was partitioned between CH$_2$Cl$_2$ (150 mL) and saturated brine (150 mL). The aqueous layer was extracted with CH$_2$Cl$_2$ (2×75 mL) and the combined organic layers were washed with saturated NaHCO$_3$ (50 mL), dried (Na$_2$SO$_4$) and concentrated to yield the crude product (2.83 g) which was purified via flash chromatography, eluting with CH$_2$Cl$_2$/hexane (75:25) to give [4S-3-(2S)]-3-[2-azido-3-[4-(1,1-dimethylethyl)phenyl]-1-oxopropyl]-4-(phenylmethyl)-2-oxazolidinone (0.885 g, 2.18 mmol) in 74% yield as an oil: $[\alpha]^{25}_D$+96.9° (c 0.45, CHCl$_3$).

EXAMPLE 7

[4S-3-(2S)]-3-[3-[4-(1,1-Dimethylethyl)phenyl]-2-[[(1,1-dimethylethoxy)carbonyl]amino]-1-oxopropyl]-4-(phenylmethyl)-2-oxazolidinone To a solution of [4S-3-(2S)]-3-[2-azido-3-[4-(1,1-dimethylethyl)phenyl]-1-oxopropyl]-4-(phenylmethyl)-2-oxazolidinone (1.15 g, 2.83 mmol) and di-tert-butyl dicarbonate (2.30 g of 97% pure, 10.24 mmol) in dry DMF (27 mL) was added 10% Pd/C (267 mg). The suspension was hydrogenated at 50 psi in a Parr hydrogenator for 3 hrs and filtrated through Celite. The filtrate was concentrated and partitioned between EtOAc (200 mL) and saturated brine (50 mL). The organic layer was washed with brine (3×50 mL), dried (Na$_2$SO$_4$) and concentrated to yield crude product (2.57 g) which was purified via flash silica gel chromatography eluting with a mixture of EtOAc and hexane (30:70) to yield [4S-3-(2S)]-3-[3-[4-(1,1-dimethylethyl)phenyl]-2-[[(1,1-dimethylethoxy)carbonyl]amino]-1-oxopropyl]-4-(phenylmethyl)-2-oxazolidinone (1.33 g, 2.77 mmol) in 98% yield as an oil. $[\alpha]^{25}_D$+76.3° (C 0.78, CHCl$_3$).

EXAMPLE 8

N-[(1,1-Dimethylethoxy)carbonyl]-4-(1,1-dimethylethyl)-L-phenylalanine

To a solution of [4S-3-(2S)]-3-[3-[4-(1,1-dimethylethyl)phenyl]-2-[[(1,1-dimethylethoxy)carbonyl]amino]-1-oxopropyl]-2-oxo-4-(phenylmethyl)oxazolidinone (1.33 g, 2.77 mmol) in THF (42 mmol) and H$_2$O (13 mL) at 0° C. was added 30% H$_2$O$_2$ (1.4 mL) and LiOH.H$_2$O (144 mg, 3.43 mmol). The reaction mixture was stirred at 0° C. for 1.25 h and was quenched with aqueous Na$_2$SO$_3$ (1.53 g in 8.4 mL) followed by sat. NaHCO$_3$ (28 mL). The mixture was concentrated and the residue was acidified to pH 2-3 with 6N HCl and extracted with CH$_2$Cl$_2$ (4×50 mL). The aqueous extracts were dried (Na$_2$SO$_4$) and concentrated to give the crude product which was purified via flash chromatography, eluting with EtOAc and then with 1% HOAc in EtOAc to give N-[(1,1-dimethylethoxy)carbonyl]-4-(1,1-dimethylethyl)-L-phenylalanine (0.80 g, 2.49 mmol) in 90% yield as an amorphous solid: $[\alpha]^{25}_D$+32.9° (c 0.96, CHCl$_3$). Chiral gc analysis, >99% enantiomeric purity.

EXAMPLE 9

Benzo[b]thiophene-2-carboxaldehyde

To a solution of thianaphthene (1.45 g, 10.5 mmol (97% pure)) in anhydrous Et$_2$O (20 mL) at −15° C. was added dropwise a 1.6M solution of n-BuLi in hexane (9.9 mL, 15.7 mmol). The mixture was stirred at −15° C. (1.75 h) and at 25° C. (15 min). After recooling to −15° C., anhydrous N-methylformanilide (1.6 mL, 12.7 mmol) (distilled from CaH$_2$) was added dropwise and the mixture was heated at reflux (30 min). The reaction mixture was quenched by addition of a mixture of 3N HCl (9 mL) and ice chips (20 mL). The organic phase was separated and the aqueous phase was extracted with Et$_2$O (3×75 mL). The combined organic layers were washed with 1N HCl (3×40 mL), saturated aq. NaHCO$_3$ (40 mL), dried (MgSO$_4$), and evaporated to dryness. The residue was dissolved in EtOH (3 mL) and mixed with saturated aq. NaHSO$_3$ (15 mL). The resulting mixture was allowed to stand for 30 min and the crystalline bisulfite addition product was collected by filtration, washing with Et$_2$O (50 mL) and dried in a vacuum desicator. The yellow solid was dissolved in warm H$_2$O (30 mL) and cooled to 0° C. Saturated aq. Na$_2$CO$_3$ was added and the mixture was stirred at 25° C. for 15 min. Filtration, washing with H$_2$O and drying afforded benzo[b]thiophene-2-carboxaldehyde as an amorphous solid (1.25 g, 7.68 mmol) in 73% yield.

EXAMPLE 10

(E)-3-(Benzo[b]thien-2-yl)-2-propenoic acid ethyl ester

To a solution of benzo[b]thiophene-2-carboxaldehyde (4.40 g, 27.1 mmol) and triethyl phosphonoacetate (16.6 mL, 83.2 mmol) in absolute EtOH (120 mL) was added a solution of EtONa/EtOH (made from 1.92 g of Na and 70 mL of EtOH) at 40° C. with stirring. The mixture was then heated at reflux for 40 min. After cooling to r.t. the mixture was concentrated to remove most of the solvent, mixed with crushed ice (60 mL) and water (60 mL), and was extracted with Et$_2$O (3×450 mL). The combined extracts were washed with brine (2×200 mL), dried (MgSO$_4$), and evaporated to dryness. The crude solid was purified by a flash chromatography on silica gel using 15% EtOAc/hexane as the eluent to give-(E)-3-(benzo[b]thien-2-yl)-2-propenoic acid ethyl ester (4.44 g, 19.1 mmol) in 71% yield as an amorphous solid.

EXAMPLE 11

Benzo[b]thiophene-2-propanoic acid ethyl ester

A mixture of (E)-3-(benzo[b]thienyl)-2-propenoic acid ethyl ester (3.65 g, 15.7 mmol), absolute EtOH (200 mL) and 5% Pd/C (800 mg) was hydrogenated at 1 atm for 3 h. An additional 200 mg of 5% Pd/C was added and the mixture was again hydrogenated for 1.5 h. The mixture was filtered through a pad of Celite washing thoroughly with $CH_2Cl_2$. The combined filtrates were concentrated to dryness and the resulting glass was purified by flash chromatography, eluting with 15% EtOAc/hexane to give benzo[b]thiophene-2-propanoic acid ethyl ester (3.55 g, 15.2 mmol) in 96.5% as a glass.

EXAMPLE 12

Benzo[b]thiophene-2-propanoic acid

To a solution of benzo[b]thiophene-2-propanoic acid ethyl ester (3.52 g, 15.0 mmol) in MeOH (200 mL) was added at 0° C. 10% KOH/MeOH (70 mL, 144 mmol) and $H_2O$ (30 mL). The solution was stirred at 25° C. for 6 h then kept in a refrigerator (0° C.) overnight. After addition of $H_2O$ (20 mL), the mixture was concentrated under reduced pressure to remove most of MeOH then acidified carefully with 3N HCl to pH 2. The resultant turbid mixture was extracted with $Et_2O$ (3×500 mL). The combined extracts were washed with brine (200 mL), dried ($MgSO_4$), and concentrated to dryness to give benzo[b]thiophene-2-propanoic acid (3.04 g, 14.7 mmol) in 98% yield as a solid, mp 140°-142° C.

EXAMPLE 13

(S)-3-[3-(Benzo[b]thien-2-yl)-1-oxopropyl]-4-(phenylmethyl)-2-oxazolidinone.

To a solution of benzo[b]thiophene-2-propanoic acid (1.10 g, 5.33 mmol) and $Et_3N$ (0.89 mL, 6.4 mmol) in dry THF (22 mL) at −78° C. was added dropwise pivaloyl chloride (0.66 mL, 5.4 mmol). After the resultant white suspension was stirred for 10 min at −78° C. and 30 min at 0° C., it was recooled to −78° C. and a precooled (−78° C.) solution of metallated oxazolidinone, prepared by addition of n-BuLi (1.6M in hexane, 3.66 mL, 5.85 mmol) to a −78° C. solution of (S)-(−)-4-benzyl-2-oxazolidinone (1.05 g, 5.87 mmol) in THF (22 mL), was added via a cannula. The reaction mixture was stirred for an additional 1 h and then was quenched by addition of saturated aq. $NH_4Cl$ (36 mL). The mixture was concentrated and the residue was extracted with $CH_2Cl_2$ (3×100 mL). The combined organic phases were washed with saturated aq. $NaHCO_3$ (85 mL), dried ($Na_2SO_4$) and concentrated to dryness. The crude solid (2.31 g) was purified by flash chromatography, eluting with EtOAc-hexane (1:2.5) to give (S)-3-[3-(benzo[b]thien-2-yl)-1-oxopropyl]-4-(phenylmethyl)-2-oxazolidinone (1.82 g, 4.98 mmol) in 93% yield as a solid, mp 119°-122° C. $[\alpha]^{25}_D + 54.9°$ (c 0.55, $CHCl_3$).

EXAMPLE 14

[4S-3-(2S)]-3-[2-Azido-3-(benzo[b]thien-2-yl)-1-oxopropyl]-4-(phenylmethyl)-2-oxazolidinone To a flask containing dry THF (72 mL) at −78° C., under argon was added a solution of potassium bis(trimethylsilyl)amide (0.5M in toluene, 20.8 mL, 10.4 mmol). The mixture was stirred for 15 min, then a precooled (−78° C.) solution of (S)-3-[3-(benzo[b]thien-2-yl)-1-oxopropyl]-4-(phenylmethyl)-2-oxazolidinone (1.73 g, 4.73 mmol) in THF (60 mL) was transferred via a cannula into the potassium bis(trimethylsilyl)amide solution. The mixture was stirred at −78° C. for 20 min. Then a precooled (−78° C.) solution of 2,4,6-triisopropylbenzenesulfonyl azide (3.83 g, 12.4 mmol) in THF (36 mL) was transferred via a cannula to the above enolate solution. The mixture was stirred for another 1.5 h at −78° C. and the reaction was quenched by the dropwise addition of acetic acid (1.24 mL). The mixture was stirred at 25° C. for 10 min then at 30° C. for 2 hr. After addition of saturated aq. $NaHCO_3$ (54 mL), the mixture was concentrated to remove most of THF and partitioned between $CH_2Cl_2$ (250 mL) and brine (150 mL). The aqueous phase was extracted with $CH_2Cl_2$ (2×250 mL). The combined organic extracts were washed with brine (100 mL), dried ($Na_2SO_4$) and concentrated to dryness. The residual oil (5.3 g) was purified by a flash chromatography, eluting with $CH_2Cl_2$ to give [4S-3-(2S)]-3-[2-azido-3-(benzo[b]thien-2-yl)-1-oxopropyl]-4-(phenylmethyl)-2-oxazolidinone (1.36 g, 3.35 mmol) in 71% yield as a solid: mp 101°-102° C.; $[\alpha]^{25}_D + 60.7°$ (c 0.60, $CHCl_3$); IR(KBr).

EXAMPLE 15

[4S-3-(2S)]-3-[3-(Benzo[b]thien-2-yl)-2-[[(1,1-dimethylethoxy)carbonyl]amino]-1-oxopropyl]-4-(phenylmethyl)-2-oxazolidinone A solution of [4S-3-(2S)]-3-[2-azido-3-(benzo[b]thien-2-yl)-1-oxopropyl]-4-(phenylmethyl)-2-oxazolidinone (1.20 g, 2.95 mmol) in dry DMF (30 mL) was hydrogenated over 10% Pd/C (302 mg) and di-tert-butyl dicarbonate (2.40 g, 10.7 mmol) in a Parr hydrogenation flask at 50 psi for 2 h. The mixture was diluted with $CH_2Cl_2$ (30 mL) and filtered through a pad of Celite washing thoroughly with $CH_2Cl_2$. The combined filtrates were concentrated and the residue was partitioned between EtOAc (300 mL) and brine (60 mL). The aqueous layer was extracted with EtOAc (100 mL) and the combined organic extracts were washed with brine (2×60 mL), dried ($Na_2SO_4$) and concentrated to dryness. The crude solid (2.98 g) was purified by a flash chromatography, eluting with EtOAc/hexane (2:3) to give [4S-3-(2S)]-3-[3-(benzo[b]thien-2-yl)-2-[[(1,1-dimethylethoxy)carbonyl]amino]-1-oxopropyl]-4-(phenylmethyl)-2-oxazolidinone (1.21 g, 2.52 mmol) in 85% yield, mp 177°-178° C.; $[\alpha]^{25}_D + 73.8°$ (c 0.38, $CHCl_3$); IR(KBr).

EXAMPLE 16

(S)-α-[[(1,1-Dimethylethoxy)carbonyl]amino]benzo[b]thiophene-2-propanoic acid To a solution of [4S-3-(2S)]-3-[3-(benzo[b]thien-2-yl)-2-[[(1,1-dimethylethoxy)carbonyl]amino]-1-oxopropyl]-4-(phenylmethyl)-2-oxazolidinone (1.17 g, 2.43 mmol) in THF (37 mL) and $H_2O$ (11 mL) was added 30% $H_2O_2$ (1.23 mL) and solid $LiOH \cdot H_2O$ (126 mg, 3.00 mmol). The mixture was stirred at 0° C. for 1 h and was quenched by the addition of $Na_2SO_3$ solution (1.33 g in 7 mL $H_2O$) followed by the addition of saturated aq. $NaHCO_3$ (25 mL) at 0° C. After concentration to remove most of THF, the residue was diluted with $H_2O$ (70 mL) and extracted with $CH_2Cl_2$ (3×70 mL). The aqueous layer was acidified with 5N HCl to a pH of 2-3, and was extracted with EtOAc (5×100 mL). The combined extracts were washed with brine (80 mL), dried ($Na_2SO_4$) and concentrated to dryness to give (S)-α-[[(1,1-dimethylethoxy)carbonyl]amino]benzo[b]thiophene-2-propanoic acid (0.768 g, 2.39 mmol) in 98% yield as a foamy glass: mp 128°-129° C., $[\alpha]^{25}_D + 83.2°$ (c 0.31, $CHCl_3$). Chiral gc analysis, >99.5% enantiomeric purity.

EXAMPLE 17

(E)-3-(3-Quinolinyl)-2-propenoic acid methyl ester

A Fisher-Porter pressure bottle was charged with 3-bromoquinoline (2.77 mL, 20 mmol), methyl acrylate (2.25 mL, 25 mmol), palladium diacetate (44 mg, 0.2 mmol), and tri-o-tolylphosphine (244 mg, 0.802 mmol) in Et$_3$N (10 mL). The atmosphere was replaced with argon, the bottle sealed and the mixture was stirred and heated at 100° C. for 6 h. The cooled mixture was partitioned between CH$_2$Cl$_2$ (200 mL) and H$_2$O (100 mL) and the aqueous layer was extracted with CH$_2$Cl$_2$ (2×100 mL). The combined organic layers were washed with H$_2$O (100 mL) dried (Na$_2$SO$_4$) and concentrated to give 5.56 g of crude product which was purified by silica gel chromatography, eluting with a mixture of EtOAc and hexane in (1:1) to give (E)-3-(3-quinolinyl)-2-propenoic acid methyl ester (4.26 g, 20 mmol) in quantitative yield, mp 118°-120° C.

EXAMPLE 18

3-Quinolinepropanoic acid methyl ester

A mixture of (E)-3-(3-quinolinyl)-2-propenoic acid methyl ester (3.6 g, 16.9 mmol) and 5% Pd/C (0.4 g) in EtOAc (300 mL) was hydrogenated at atmospheric pressure. Upon sessation of hydrogen uptake, the catalyst was separated by filtration through a pad of Celite and the filtrate was evacuated to dryness to give the crude product (3.48 g) which was purified via flash chromatography eluting with a mixture of CH$_2$Cl$_2$ and ether (1:1) to give 3-quinolinepropanoic acid methyl ester (2.77 g, 12.9 mmol) in 76% yield as a glass.

EXAMPLE 19

3-Quinolinepropanoic acid

A solution of 3-quinolinepropanoic acid methyl ester (2.21 g, 10.3 mmol) in 10% KOH/MeOH (48.2 mL), H$_2$O (20 mL) and methanol (134 mL) was stirred at room temperature for 3 h. Upon completion of reaction, the solution was concentrated and the aqueous residue was acidified to pH 5-6 with glacial HOAc. A crystalline solid formed which was filtered, washing with H$_2$O until the filtrate was neutral and dried to give 3-quinolinepropanoic acid (1.84 g, 9.14 mmol) in 89% yield as a solid, mp 180°-181° C.

EXAMPLE 20

(S)-4-(Phenylmethyl)-3-[3-(3-quinolinyl)-1-oxopropyl]-2-oxazolidinone

In a manner analogous to that described in example 5, 1.60 g (7.95 mmol) of 3-quinolinepropanoic acid was converted to 2.87 g (7.95 mmol) of (S)-4-(phenylmethyl)-3-[3-(3-quinolinyl)-1-oxopropyl]-2-oxazolidinone in quantitative yield as a glass: $[\alpha]^{25}_D+61.4°$ (c 0.53, CHCl$_3$).

EXAMPLE 21

[4S-3-(2S)]-3-[2-Azido-3-(3-quinolinyl)-1-oxopropyl]-4-(phenylmethyl)-2-oxazolidinone In a manner analogous to that described in example 6, 2.88 g (7.99 mmol) of (S)-4-(phenylmethyl)-3-[3-(3-quinolinyl)-1-oxopropyl]-2-oxazolidinone was converted to 2.17 g (5.41 mmol) of [4S-3-(2S)]-3-[2-azido-3-(3-quinolinyl)-1-oxopropyl]-4-(phenylmethyl)-2-oxazolidinone in 67% yield as a solid: mp 113°-116° C.; $[\alpha]^{25}_D+63.2°$ (C 0.51, CHCl$_3$).

EXAMPLE 22

[4S-3-(2S)]-3-[2-[[(1,1-dimethylethoxy)carbonyl]amino]-3-(3-quinolinyl)-1-oxopropyl]-4-(phenylmethyl)-2-oxazolidinone In a manner analogous to that described in example 7, 2.17 g (5.41 mmol) of [4S-3-(2S)]-3-[2-azido-3-(3-quinolinyl)-1-oxopropyl]-4-(phenylmethyl)-2-oxazolidinone was converted to [4S-3-(2S)]-3-[2-[[(1,1-dimethylethoxy)carbonyl]amino]-3-(3-quinolinyl)-1-oxopropyl]-4-(phenylmethyl)-2-oxazolidinone in 88% yield as a crystalline solid, mp 176°-177° C.: $[\alpha]^{25}_D+72.2°$ (c 0.97, CHCl$_3$).

EXAMPLE 23

(S)-α-[[(1,1-Dimethylethoxy)carbonyl]amino]-3-quinolinepropanoic acid

To a solution of [4S-3-(2S)]-3-[2-[[(1,1-dimethylethoxy)carbonyl]amino]-3-(3-quinolinyl)-1-oxopropyl]-4-(phenylmethyl)-2-oxazolidinone (2.17 g, 4.56 mmol) in peroxide free THF (70 mL) and H$_2$O (20 mL) was added LiOH.H$_2$O (237 mg, 5.65 mmol) and 30% H$_2$O$_2$ (2.31 mL). The mixture was stirred at 0° C., under argon for 1.5 h and was quenched by addition of Na$_2$SO$_3$ solution (2.52 g in 13.9 mL of H$_2$O), followed by addition of sat. NaHCO$_3$ (46 mL). The mixture was concentrated, H$_2$O (140 mL) was added and the aqueous residue was extracted with EtOAc (3×100 mL). The basic aqueous layer was acidified with 6N HCl to pH 6-7, saturated with solid NaCl and extracted with EtOAc (3×200 mL). The combined organic layers were washed with brine (100 mL) dried (Na$_2$SO$_4$) and concentrated to give (S)-α-[[(1,1-dimethylethoxy)carbonyl]amino]-3-quinolinepropanoic acid (1.3 g, 4.11 mmol) in 90% yield as a white solid, mp 159°-160° C.; $[\alpha]^{25}_D-12.1°$ (c 1.0, CH$_3$OH).

EXAMPLE 24

(S)-3-(1-Oxotetradecyl)-4-(phenylmethyl)-2-oxazolidinone

In a manner analogous to that described in example 5, 3.00 g (13.1 mmol) of myristic acid was converted to 4.45 g (11.0 mmol) of (S)-3-(1-oxotetradecyl)-4-(phenylmethyl)-2-oxazolidinone in 84% yield as an amorphous solid: $[\alpha]^{25}_D+39.5°$ (C 0.51, CHCl$_3$).

EXAMPLE 25

[4S-3-(2S)]-3-(2-Azido-1-oxotetradecyl)-4-(phenylmethyl)-2-oxazolidinone

In a manner analogous to that described in example 6, 2.00 g (4.96 mmol) of (S)-3-(1-oxotetradecyl)-4-(phenylmethyl)-2-oxazolidinone was converted to 1.48 g (3.45 mmol) of [4S-3-(2S)]-3-(2-azido-1-oxotetradecyl)-4-(phenylmethyl)-2-oxazolidinone in 70% yield as an oil: $[\alpha]^{25}_D+75.5°$ (c 0.45, CHCl$_3$).

EXAMPLE 26

[4S-3-(S)]-3-[2-[[(1,1-Dimethylethoxy)carbonyl]amino]-1-oxotetradecyl]-4-(phenylmethyl)-2-oxazolidinone In a manner analogous to that described in example 7, 1.31 g (3.06 mmol) of [4S-3-(2S)]-3-(2-azido-1-oxotetradecyl)-4-(phenylmethyl)-2-oxazolidinone was converted to 1.23 g (2.45 mmol) of [4S-3-(S)]-3-[2-[[(1,1-dimethylethoxy)carbonyl]amino]-1-oxotetradecyl]-4-(phenylmethyl)-2-oxazolidinone in 80% yield as an amorphous solid: $[\alpha]^{25}_D+39.8°$ (C 0.59, CHCl$_3$).

EXAMPLE 27

(S)-α-[[(1,1-Dimethylethoxy)carbonyl]amino]tetradecanoic acid

In a manner analogous to that described in example 8, 1.18 g (2.35 mmol) of [4S-3-(S)]-3-[2-[[(1,1-dimethylethoxy)carbonyl]amino]-1-oxotetradecyl]-4-(phenylmethyl)-2-oxazolidinone was converted to 790 mg (2.30 mmol) of (S)-α-[[(1,1-dimethylethoxy)carbonyl]amino]-tetradecanoic acid in 98% yield as an amorphous solid: $[\alpha]^{25}_D$ −1.61° (c 1.0, MeOH). Chiral gc analysis >99.6% enantiomerically pure.

EXAMPLE 28

(S)-3-(4-cyclohexyl-1-oxobutyl)-4-(phenylmethyl)-2-oxazolidinone

A solution of pivaloyl chloride (3.57 g, 2.96 mmol) in THF (25 ml) was added to a cold (−78° C.) solution of 4-cyclohexylbutyric acid (5.042 g, 29.62 mmol) and triethyl amine (3.60 g, 35.6 mmol) in THF (100 mL). The resultant white suspension was stirred for 10 min. at −78° C. and then warmed to 0° C. and kept there for 30 min. The reaction mixture was recooled to −78° C. and a cold (−78° C.) metallated oxazolidinone solution in THF (125 ml) [prepared by the addition of n-BuLi (17.65 ml. of 1.65M solution in hexane, 28.2 mmol) to a −78° C. solution of (S)-4-(phenylmethyl)-2-oxazolidinone in THF (125 ml)] was added via a cannula under the positive pressure of argon. The reaction mixture was then warmed to 0° C. and kept there for another 30 min. The reaction was quenched by the addition of saturated NH4Cl (75 ml). The volatiles were removed on rotavapor at reduced pressure and the residue was extracted with CH2Cl2 (3×200 ml). The combined organic phases were washed with 1N NaOH (150 ml) and dried (Na2SO4). The organic layer was concentrated and the residue was purified by flash silica gel chromatography, eluting with hexane:ethyl acetate (3:1) to yield 8.066 g (85%) of (S)-3-(4-cyclohexyl-1-oxobutyl)-4-(phenylmethyl)-2-oxazolidinone: Rf 0.34 (3:1 hexane:ethyl acetate), m.p. 69°-70° C. $[\alpha]_D^{25}$ +47.3° (c 0.97 CHCl3).

EXAMPLE 29

[4S-3-(2S)]-3-(2-Azido-4-cyclohexyl-1-oxobutyl)-4-(phenylmethyl)-2-oxazolidinone A solution of potassium bis(trimethylsilyl) amide (KHDMS) (24.1 ml of 0.5M solution in toluene, 12.05 mmol) was added to a flask containing THF at −78° C. under argon. The mixture was stirred for 15 min. The a precooled (−78° C.) solution of (S)-3-(4-cyclohexyl-1-oxobutyl)-4-(phenylmethyl)-2-oxazolidinone (3.485 g, 10.56 mmol) in THF (35 ml) was transferred into the above solution via a cannula. The mixture was stirred for 60 min. at −78° C. and a cold (−78° C.) solution of triisopropylbenzene sulfonyl azide (4.04 g, 13.09 mmol) in THF (35 ml) was transferred into the above stirred solution via a cannula. The mixture was kept at −78° C. for another 60 min. The reaction was then quenched by the addition of acetic acid (2.2 ml, 38.16 mmol) and the reaction mixture was allowed to warm up to room temperature over night (15 h) Saturated NaHCO3 (50 ml) was added to the mixture. The volatiles were removed on rotavapor at reduced pressure. The aqueous solution was extracted with CH2Cl2 (3×150 mL). The organic layer was washed with brine (2×50 ml) and dried (Na2SO4). Concentration and purification of the residue by flash silica gel chromatography, eluting with CH2Cl2:hexane (1:1) yielded 2.367 g (61%) of [4S-3-(2S)]-3-(2-azido-4-cyclohexyl-1-oxobutyl)-4-(phenylmethyl)-2-oxazolidinone: Rf 0.64 (100% CH2Cl2). $[\alpha]_D^{25}$ +86.07 (c 0.82, CHCl3).

EXAMPLE 30

[4S-3-(S)]-3-[4-Cyclohexyl-2-[[(1,1-dimethylethoxy)carbonyl]amino]-1-oxobutyl]-4-(phenylmethyl)-2-oxazolidinone A solution of [4S-3-(2S)]-3-(2-azido-4-cyclohexyl-1-oxobutyl)-4-(phenylmethyl)-2-oxazolidinone (80 mg, 0.22 mmol) in DMF (2 ml) was hydrogenated in a Parr hydrogenator at 50 psi, in the presence of di-tert-butyl dicarbonate (171.3 mg, 0.78 mmol), over 10% Pd-C (20.5 mg) for 2.5 h The reaction mixture was diluted with ethyl acetate (150 ml), washed with brine (2×50 ml) and dried (Na2SO4). The organic layer was concentrated and the residue was purified by flash silica gel chromatography eluting with CH2Cl2:hexane (4:1) to yield [4S-3-(S)]-3-[4-cyclohexyl-2-[[(1,1-dimethylethoxy)carbonyl]amino]-1-oxobutyl]-4-(phenylmethyl)-2-oxazolidinone (72.3 mg, 75%); Rf 0.22 (100% CH2Cl2); m.p. 135° C.; $[\alpha]_D^{25}$ +47.35 (c 0.62 CHCl3).

EXAMPLE 31

(S)-α-[[(1,1-dimethylethoxy)carbonyl]amino]cyclohexanebutanoic acid

A solution of 30% H2O2 in water (1 ml) and solid LiOH.H2O (102.8 mg, 2.45 mmol) was added to a solution of [4S-3-(S)]-3-[4-cyclohexyl-2-[[(1,1-dimethylethoxy)carbonyl]amino]-1-oxobutyl](4-phenylmethyl)-2-oxazolidinone (879.5 mg, 1.98 mmol), in THF (30 ml) and water (9 ml) 0° C. The mixture was stirred for 1 h. The reaction was quenched by the addition of Na2SO3 (1.09 g in 6 ml H2O) solution, followed by 0.5N NaHCO3 (20 ml) solution. The reaction mixture was then diluted with water (60 ml) and extracted with CH2Cl2 (3×50 ml). The aqueous layer was acidified with 5N HCl to pH 2-3, the aqueous layer was extracted with ethyl acetate (4×80 ml) and dried (Na2SO4). The organic layer was concentrated to yield (S)-α-[[(1,1-dimethylethoxy)carbonyl]amino]cyclohexanebutanoic acid (517.5 mg, 92%); Rf 0.35 (1:1 hexane:ethyl acetate with 1% acetic acid); $[\alpha]_D^{25}$ +15.2 (c 0.59 CHCl3).

EXAMPLE 32

α-Methoxy-α-trimethylsilyl-2-hydroxy-tricyclo[3.3.1.1-3,7]decane-2-methane

Preparation of this compound has been described: Magnus, P.; Roy, G. *Organometallics*, 1982, 1, 553. To a pre-cooled (−78° C.) solution of (methoxymethyl)-trimethyl silane (0.083 mol, 9.84 g) in tetrahydrofuran (100 mL) was added sec-butyl lithium (1.3M in cyclohexane, 0.083 mol, 64.0 mL) over the course of 25 min. After the addition of the base was complete the reaction temperature was brought up to −20° C. for 30 min. The anion was re-cooled to −35° C. and a solution of 2-adamantanone (0.076 mol, 11.36 g) in tetrahydrofuran (30 mL) added over the course of 20 min. The resulting pale yellow solution was stirred at low temperature (−20° C.) for 20 min then warmed to room temperature over the course of 1.5 h. The reaction mixture was cooled to 0° C. then quenched by the cautious addition of saturated aqueous ammonium chloride until the evolution of gas ceased. The heterogeneous mixture was concentrated and the resulting residue partitioned with diethyl ether (150 mL) and distilled water (25 mL). The layers were separated and the aqueous phase extracted with diethyl ether (3×150 mL). The combined ethereal extracts were dried (K$_2$CO$_3$) and concentrated to provide a moist white solid. The crude product was recrystallized from hexanes/diethyl ether to provide the title compound as small white needles (76%, 15.43 g). mp 65°-66° C.

EXAMPLE 33

Tricyclo[3.3.1-3,7]decane-2-carboxaldehyde

Preparation of this compound has been described: Magnus, P.; Roy, G. *Organometallics*, 1982, 1, 553. A pre-cooled flask (0° C.) containing α-methoxy-α-trimethylsilyl-2-hydroxytricyclo[3.3.1.1-3,7]decane-2-methane (0.034 mol, 9.07 g) was charged with cold (0° C.) formic acid (500 mL). The pale yellow heterogeneous mixture was stirred at 0° C. for 10 min then allowed to warm to ambient temperature. After stirring an additional 30 min, the reaction was found to be complete by TLC analysis (SiO$_2$, 6:1 hexanes/EtOAc). The formic acid was removed in vacuo by distillation (25° C.) and the resulting yellowish gummy residue was partitioned with diethyl ether (150 mL) and saturated aqueous sodium bicarbonate (100 mL). The aqueous phase was separated, extracted with diethyl ether (3×150 mL), the combined ethereal layers dried (K$_2$CO$_3$), and concentrated. This provided tricyclo[3.3.1-3,7]decane-2-carboxaldehyde as a white solid which was of sufficient purity to be used directly in the next reaction (97%, 5.38 g). mp 99°-102° C.

EXAMPLE 34

(E)-3-Tricyclo[3.3.1.1-3,7]dec-2-yl-2-propenoic acid ethyl ester and
(Z)-3-Tricyclo[3.3.1.1-3,7]dec-2-yl-2-propenoic acid ethyl ester To a solution of tricyclo[3.3.1.1-3,7]decane carboxaldehyde (0.033 mol, 5.38 g) in toluene (pre-dried over 4 Å molecular sieves, 109 mL, 0.3M) was added (carbethoxymethylene)triphenylphosphorane (0.036 mol, 12.55 g) in several portions. The clear, colorless solution was heated overnight (14 h) at 85°-90° C. (oil bath temperature). The resulting pale yellow solution was concentrated and the residue was purified by flash chromatography, eluting with hexanes/EtOAc (20:1) to provide an 82:18 mixture of (E)-3-tricyclo[3.3.1.1-3,7]dec-2-yl-2-propenoic acid ethyl ester and (Z)-3-tricyclo[3.3.1.1-3,7]dec-2-yl-2-propenoic acid ethyl ester, respectively, as a viscous colorless oil (90%, 6.89 g). These isomers were not separated prior to reduction of the olefin by catalytic hydrogenation.

EXAMPLE 35

Tricyclo[3.3.1.1-3,7]decane-2-propanoic acid ethyl ester

The mixture of (E)-3-tricyclo[3.3.1.1-3,7]dec-2-yl-2-propenoic acid ethyl ester and (Z)-3-tricyclo[3.3.1.1-3,7]dec-2-yl-2-propenoic acid ethyl ester (0.018 mol, 4.23 g), dissolved in ethyl acetate (500 mL) was hydrogenated over 10% Pd/C catalyst (450 mg), (1 atm H$_2$) with vigorous stirring until the uptake of hydrogen ceased (1 h). The reaction mixture was filtered through a pad of celite, and the filtrate dried (Na$_2$SO$_4$) and concentrated in vacuo to provide tricyclo[3.3.1.1-3,7]decane-2-propanoic acid ethyl ester as a colorless oil.

EXAMPLE 36

Tricyclo[3.3.1.1-3,7]decane-2-propanoic acid

To a solution of tricyclo[3.3.1.1-3,7]decane-2-propanoic acid ethyl ester (0.011 mol, 2.68 g) in anhydrous ethanol (135 mL) was added potassium hydroxide (0.057 mol, 3.18 g) in several portions. The clear solution was heated at reflux for 1 h, cooled to ambient temperature, and concentrated. The yellow residue was partitioned with CH$_2$Cl$_2$ (100 mL) and water (50 mL), and the basic, aqueous phase extracted with CH$_2$Cl$_2$ (100 mL). The aqueous phase was re-acidified (pH 2) by the addition of 10% aqueous hydrochloric acid, and extracted with CH$_2$Cl$_2$ (3×50 mL). The combined organic extracts were dried (Na$_2$SO$_4$) and concentrated to provide tricyclo[3.3.1.1-3,7]decane-2-propanoic acid as a white solid (96%, 2.27 g). mp 115.5°-116° C.

EXAMPLE 37

(S)-3-[1-Oxo-3-(tricyclo[3.3.1.1-3,7]dec-2-yl)propyl]-4-(phenylmethyl)-2-oxazolidinone To a cold (−78° C.) solution of tricyclo[3.3.1.1-3,7]decane-2-propanoic acid (9.63 mmol, 2.006 g) in tetrahydrofuran (25 mL) was added triethylamine (11.5 mmol, 1.170 g, 1.61 mL), and the resulting mixture stirred for 10 min. Dropwise addition of pivaloyl chloride (9.63 mmol, 1.161 g, 1.19 mL) to the carboxylate provided a thick suspension, which was stirred at low temperature (−78° C.) for 15 min and then warmed to 0° C. (30 min). In a separate flask, while the mixed anhydride was forming, was introduced a solution of (S)-4-(phenylmethyl)-2-oxazolidinone (9.44 mmol, 1.673 g) in tetrahydrofuran (25 mL). This mixture was cooled to −78° C. and n-butyl lithium (1.6M in hexanes, 9.44 mmol, 5.90 mL) was added over the course of 10 min. The oxazolidinone anion was allowed to form for 30 min at low temperature (−78° C.). The mixed anhydride was recooled to −78° C. (15 min) and the anion added dropwise via cannulae. The flask containing the anion was rinsed with tetrahydrofuran (5 mL) and the washings transferred via a cannulae to the reaction mixture. The reaction mixture was stirred at low temperature (−78° C.) for 15 min, warmed to 0° C. over the course of 45 min, and quenched by the addition of saturated aqueous ammonium chloride (20 mL). The heterogeneous mixture was concentrated in vacuo and partitioned with CH$_2$Cl$_2$ (100 mL) and water (25 mL). The aqueous phase was extracted with CH$_2$Cl$_2$ (3×100 mL), and the combined organic layers dried (Na$_2$SO$_4$) then concentrated in vacuo. This pale yellow oil was purified by flash chromatography, eluting with hexanes/EtOAc (6:1), to provide (S)-3-[1-oxo-3-(tricyclo[3.3.1.1-3,7]dec-2-yl)propyl]-4-(phenylmethyl)-2-oxazolidinone as a colorless glass that crystallized upon standing overnight at room temperature (93%, 3.234 g). mp 82°-83° C.

EXAMPLE 38

[4S-3-(2S)]-1-[(1-Tricyclo[3.3.1.1-3,7]dec-2-ylmethyl)-2-[2-oxo-4-(phenylmethyl)-3-oxazolidinyl]-2-oxoethyl]-1,2-hydrazinedicarboxylic acid bis (1,1-dimethylethyl) ester Lithium diisopropylamide was prepared by the dropwise addition of n-butyl lithium (1.6M in hexanes, 6.76 mmol, 4.23 mL) to a cold (−78° C.) solution of diisopropyl amine (6.76 mmol, 648 mg, 950 μL) in tetrahydrofuran (20 mL). The anion was allowed to form for 30 min (−78° C.) then transferred, via a cannulae, to a pre-cooled (−78° C.) solution of (S)-3-[1-oxo-3-(tricyclo[3.3.1.1-3,7]dec-2-yl)propyl]-4-(phenylmethyl)-2-oxazolidinone (6.15 mmol, 2.26 g) in tetrahydrofuran (25 mL). The reaction mixture was stirred at low temperature (−78° C.) for 30 min, then a pre-cooled (−78° C.) solution of di-tert-butyl-azodicarboxylate (7.37 mmol, 1.70 g) in CH$_2$Cl$_2$ (20 mL) added via cannulae. This mixture was stirred at −78° C. (1 h), then quenched by the addition of glacial acetic acid (1 mL). The reaction was allowed to slowly warm up to ambient temperature overnight (14 h), and concentrated. The resulting residue was partitioned with ½ saturated aqueous sodium bicarbonate (50 mL) and CH$_2$Cl$_2$ (100 mL), the aqueous phase extracted with CH$_2$Cl$_2$ (3×100 mL), and the combined organic layers dried (Na$_2$SO$_4$). The solvent was removed by rotary evaporation and the resulting thick yellow oil purified by flash chromatography, eluting with hexanes/EtOAc (6:1) to provide [4S-3-(2S)]-1-[(1-tricyclo[3.3.1.1-3,7]dec-2-ylmethyl)-2-[2-oxo-4-(phenylmethyl)-3-oxazolidinyl]-2-oxoethyl]-1,2-hydrazinedicarboxylic acid bis (1,1-dimethylethyl) ester as a viscous colorless oil that solidified upon evaporation overnight (0.1 torr) (82%, 3.01 g), mp 93° C. decomp. [α]$_D^{25}$+27.22 (c 0.61, CHCl$_3$).

EXAMPLE 39

(S)-1-[Carboxy(tricyclo[3.3.1.1-3,7]dec-2-ylmethyl)methyl]-1,2-hydrazinedicarboxylic acid 1,2-bis(1,1-dimethylethyl)ester.

A solution of [1S-(4S)]-1-[(1-tricyclo[3.3.1.1-3,7]dec-2-ylmethyl)-2-[2-oxo-4-(phenylmethyl)-3-oxazolidinyl]-2-oxoethyl]-1,2-hydrazinedicarboxylic acid bis(1,1-dimethylethyl) ester (4.94 mmol, 2.95 g) in 2:1 tetrahydrofuran/water (98 mL) was cooled to 0° C. and lithium hydroxide monohydrate (11.4 mmol, 0.477 g) added in one portion. The reaction was stirred at 0° C. for 45 min then allowed to slowly warm to ambient temperature while monitoring the progress of the reaction by TLC (SiO$_2$, 2:1 hexanes/EtOAc). After TLC analysis indicated complete consumption of starting material (4 h), the reaction was cautiously acidified (pH 2.4) by the dropwise addition of 10% aqueous hydrochloric acid. The mixture was concentrated, and the residue extracted with CH$_2$Cl$_2$ (4×100 mL), and the combined organic phases dried (Na$_2$SO$_4$). Concentration provided a white foam which was purified by gradient flash chromatography (1.5% MeOH/CH$_2$Cl$_2$; 5% MeOH/CH$_2$Cl$_2$ with 1% HOAc) to provide (S)-1-[carboxy(tricyclo[3.3.1.1-3,7]dec-2-ylmethyl)methyl]-1,2-hydrazinedicarboxylic acid 1,2-bis(1,1-dimethylethyl) ester as a white powder (71%, 1.54 g). mp 169°-171° C. decomp. [α]$_D^{25}$−22.42° (c=0.35, CHCl$_3$).

EXAMPLE 40

(S)-α-Aminotricyclo[3.3.1.1-3,7]decane-2-propanoic acid (S)-1-[Carboxy(tricyclo[3.3.1.1-3,7]dec-2-ylmethyl)-methyl]-1,2-hydrazinedicarboxylic acid 1,2-bis(1,1-dimethylethyl) ester (3.34 mmol, 1.46 g) was dissolved in the minimum amount of CH$_2$Cl$_2$ (20 mL) and trifluoroacetic acid (10 mL) was added dropwise via syringe. The reaction mixture was stirred at room temperature until analysis by TLC (SiO$_2$, 20% MeOH/CH$_2$Cl$_2$) showed complete consumption of starting material (1 h). This reaction solution was reduced with Raney nickel at 550-570 psi H$_2$ (4 h), to provide a green solution. The solvent was concentrated to dryness to provide a solid emerald green mass (nickel chelate of amino acid). The nickel was removed by dissolving the green solid in hot water (minimum amount) and adding enough ethylenediamine tetraacetic acid disodium salt to change the aqueous solution's color from green to blue. (S)-α-aminotricyclo[3.3.1.1-3,7]decane-2-propanoic acid crystallized as fine white needles upon cooling the blue aqueous solution (99%, 739 mg) mp 183°-186° C. [α]$_D^{25}$+16.76° (c=0.85, EtOH).

EXAMPLE 41

(S)-α-[[[(1,1-Dimethylethyl)oxy]carbonyl]amino]tricyclo[3.3.1.1-3,7]decane-2-propanoic acid A solution of 678 mg (3.03 mmol) of (S)-α-aminotricyclo[3.3.1.1-3,7]decane-2-propanoic acid, 795 mg (3.64 mmol) of di-tert-butyl dicarbonate and 850 μL (6.07 mmol) of triethylamine in 40 mL of DMF was stirred 3 h at room temperature. The mixture was concentrated and the residue was partitioned between dichloromethane and water. The aqueous phase was extracted with dichloromethane and the combined extracts were dried (Na$_2$SO$_4$). Concentration afforded an oil which was purified by flash chromatography eluting with 5% methanol:dichloromethane to afford 777 mg (79%) of (S)-α-[[[(1,1-dimethylethyl)oxy]-carbonyl]amino]tricyclo[3.3.1.1-3,7]decane-2-propanoic acid.

EXAMPLE 42

Cyclooctanepropenoic acid ethyl ester

A mixture of cyclooctanecarboxaldehyde (14.02 g, 100 mmol) and ethyl triphenylphosphoran-ylideneacetate (34.83 g, 100 mmol) in toluene (400 mL) was heated to 90° C. under argon for 8 h. The mixture was allowed to cool and stand at room temperature overnight. The solvent was concentrated and the residue diluted with hexane (500 mL). After 1 h, the mixture was filtered to remove triphenylphosphine oxide. The solution was concentrated and hexane (250 mL) was added. The mixture was allowed to stand overnight and was then filtered again and concentrated to give 20.44 g of crude cyclooctanepropenoic acid, ethyl ester as a light yellow oil.

EXAMPLE 43

Cyclooctanepropanoic acid ethyl ester

A solution of the above crude cyclooctanepropenoic acid, ethyl ester (20.4 g, 97 mmol) in ethyl acetate (300 mL) was hydrogenated at 1 atm over 10% Pd on carbon (0.75 g). After the uptake of hydrogen had stopped, the mixture was filtered to remove the catalyst, and the solvent evaporated to give 15.18 g of crude cyclooctanepropanoic acid as a colorless oil.

EXAMPLE 44

Cyclooctanepropanoic acid

To a solution of the crude cyclooctanepropanoic acid, ethyl ester in ethanol (200 mL) was added KOH (20 g). The resulting mixture was heated to reflux for 1.25 h, cooled to room temperature, and concentrated to remove the bulk of the ethanol. To the residue was added water (250 mL) and the solution was washed with CH$_2$Cl$_2$ (2×200 mL, discarded). The aqueous solution was made acidic with concentrated HCl (30 mL), with ice added to keep the mixture near room temperature. The solution was extracted with $CH_2Cl_2$ (3×200 mL), and the extracts were washed with brine, dried over $MgSO_4$, and concentrated to give crude cyclooctanepropanoic acid (11.45 g) as a colorless oil. An 0.72-g portion was evaporatively distilled to give 0.69 g of pure acid, bp 165° C./0.5 torr.

EXAMPLE 45

(S)-3-[3-Cycloooctyl-1-oxopropyl]-4-(phenylmethyl)-2-oxazolidinone

To as solution of cyclooctanepropanoic acid (3.68 g, 20.0 mmol) and triethylamine (2.22 g, 22.0 mmol) in 125 mL of anhydrous THF at −78° C. was added 2.40 g of pivaloyl chloride (2.40 g, 20.0 mmol). The solution was stirred at −78° C. for 10 min, then warmed to 0° C. and stirred for 30 min to form the mixed anhydride. In a separate flask, a solution of (S)-(−)-4-benzyl-2-oxazolidinone (3.54 g, 20.0 mmol) in 100 mL of anhydrous THF was cooled to −78° C. To the solution was added n-butyllithium (12 mL of 1.6M solution in hexanes, 20.0 mmol). The solution was stirred for 30 min at −78° C. The solution of the mixed anhydride was recooled to −78° C., and the solution of the oxazolidinone anion was transferred via a cannula into the solution of the mixed anhydride at −78° C. The mixture was stirred at −78° C. for 5 min and then at −10° C. for 1 h. To the mixture was added 100 mL of saturated $NH_4Cl$, and the mixture was stirred for 15 min. The organic layer was separated, and the aqueous extracted with $CH_2Cl_2$ (3×50 mL). The combined extracts were concentrated on a rotary evaporator, redissolved in 150 mL of $CH_2Cl_2$, and washed with 3×35 mL of 1N NaOH (cold) and dried over $Na_2SO_4$. Evaporation of the solvent afforded 7.2 g of crude (S)-3-[3-cycloooctyl-1-oxopropyl]-4-(phenylmethyl)-2-oxazolidinone. The crude product was chromatographed on silica gel, eluting with $CH_2Cl_2$, to give 6.85 g of (S)-3-[3-cycloooctyl-1-oxopropyl]-4-(phenylmethyl)-2-oxazolidinone. $[\alpha]_D^{25} = +92.56°$.

EXAMPLE 46

[4S-3-(2S)]-3-[2-Azido-3-cyclooctyl-1-oxopropyl]-4-(phenylmethyl)-2-oxazolidinone To a solution of 15.4 mL of potassium bis(trimethylsilyl) amide (0.5M in toluene, 7.7 mmol) in 35 mL of anhydrous THF at −78° C. was added via a cannula over 20 min a solution (precooled to −78° C.) of (S)-3-[3-cyclooctyl-1-oxopropyl]-4-(phenylmethyl)-2-oxazolidinone (2.4 g, 7.0 mmol) in 21 mL of anhydrous THF. After stirring for 45 min at −78° C., a solution (also precooled to −78° C.) of 2,4,6-triisopropylbenzenesulfonyl azide (2.5 g, 8.3 mmol) in 21 mL of anhydrous THF was added via a cannula. The mixture was allowed to stir at −78° C. for 20 min, then glacial acetic acid (2.1 g, 35 mmol) was added in one portion. The mixture was stirred at room temperature for 30 min, then heated to 30° C. for 1 h. The mixture was then poured into ice water (100 mL) and extracted with 3×50 mL of $CH_2Cl_2$. The combined organic phase was concentrated to give an oil, which was redissolved in $CH_2Cl_2$ (100 mL), dried over $Na_2SO_4$, and concentrated to give 5.4 g of crude [4S-3-(2S)]-3-[2-azido-3-cyclooctyl-1-oxopropyl]-4-(phenylmethyl)-2-oxazolidinone, containing some unreacted 2,4,6-triisopropylbenzenesulfonyl azide. The material was chromatographed on silica gel (240 g, 70-230 mesh) eluting with ethyl acetate-hexanes (15:85, 1000 mL), then with ethyl acetate-hexanes (20:80). Rechromatography of the fractions containing the product on silica gel (240 g, 70-230 mesh) eluting with $CH_2Cl_2$ gave 1.95 g of [4S-3-(2S)]-3-[2-azido-3-cyclooctyl)-1-oxopropyl]-4-(phenylmethyl)-2-oxazolidinone as a solid. A sample was recrystallized from hexane to give pure material, mp 59°-61° C. $[\alpha]_D^{25} + 129.77°$.

EXAMPLE 47

[4S-3-(2S)]-3-[3-Cyclooctyl-2-[[(1,1-dimethylethoxy)-carbonyl]amino]-1-oxopropyl]-4-(phenylmethyl)-2-oxazolidinone A solution of [4S-3-(2S)]-3-[2-azido-3-cyclooctyl-1-oxopropyl]-4-(phenylmethyl)-2-oxazolidinone (384 mg, 1 mmol) and di-tert-butyldicarbonate (545 mg, 2.5 mmol) in 50 mL of DMF was hydrogenated over 100 mg of 10% Pd/C at 50 PSI in a Parr apparatus. The reduction proceeded at room temperature over 5 h. The solution was diluted with ethyl acetate (50 mL) and filtered to remove the catalyst. The solution was then concentrated to an oil, then mixed with water (25 mL) and extracted with $CH_2Cl_2$ (3×25 mL. The extracts were washed with water (2×25 mL) dried over $Na_2SO_4$, and concentrated to give 762 mg of crude [4S-3-(2S)]-3-[3-cyclooctyl-2-[[(1,1-dimethylethoxy)carbonyl]amino]-1-oxopropyl]-4-(phenylmethyl)-2-oxazolidinone as an oil. Chromatography on silica gel (40 g, 70-230 mesh) eluting with ethyl acetate-hexanes (20:80) gave 300 mg of [4S-3-(2S)]-3-[3-cyclooctyl-2-[[(1,1-dimethylethoxy)carbonyl]amino]-1-oxopropyl]-4-(phenylmethyl)-2-oxazolidinone, which was recrystallized from cyclohexane to give 240 mg of pure [4S-3-(2S)]-3-[3-cyclooctyl-2-[[(1,1-dimethylethoxy)carbonyl]amino]-1-oxopropyl]-4-(phenylmethyl)-2-oxazolidinone, mp 128°-130° C. $[\alpha]_D^{25} = +92.26°$.

EXAMPLE 48

(S)-$\alpha$-[[(1,1-Dimethylethoxy)carbonyl]amino]cyclooctanepropanoic acid

A solution of [4S-3-(2S)]-3-[3-cyclooctyl-2-[[(1,1-dimethylethoxy)carbonyl]amino]-1-oxopropyl]-4-(phenylmethyl)-2-oxazolidinone (230 mg, 0.5 mmol) in 10 mL of 3:1 THF:$H_2O$ containing 0.25 mL of 30% $H_2O_2$ (2.0 mmol) was prepared and cooled to 0° C. To the solution was added lithium hydroxide (48 mg, 2.0 mmol) and the mixture was allowed to stir at 0° C. for 45 min in an ice bath. To the solution was added sodium sulfite (280 mg, 2.2 mmol, dissolved in 2 mL of $H_2O$) and sodium bicarbonate (420 mg, 5 mmol, dissolved in 5 mL of $H_2O$). The solution was concentrated on a rotary evaporator to remove most of the THF, and was then diluted with water (40 mL) and extracted with $CH_2Cl_2$ (4×25 mL). The extracts contained the recovered chiral auxiliary, (S)-4-phenylmethyl-2-oxazolidinone. The aqueous solution was adjusted to pH 1-2 with 6N HCl, and then extracted with ethyl acetate (4×20 mL). The combined extracts were dried over $Na_2SO_4$ and concentrated to give 135 mg of (S)-$\alpha$-[[(1,1-dimethylethoxy)-carbonyl]-amino]cyclooctanepropanoic acid.

EXAMPLE 49

(S)-3-[3-Cyclopentyl-1-oxopropyl]-4-(phenylmethyl)-2-oxazolidinone

Following the procedure described in Example 45, 6.4 g of cyclopentane propionyl chloride and 7.1 g of (S)-4-phenylmethyl-2-oxazolidinone yielded 11.6 g of (S)-3-[3-cyclopentyl-1-oxopropyl]-4-(phenylmethyl)-2-oxazolidinone. $[\alpha]_D^{25} = +99.61°$

EXAMPLE 50

[4S-3-(2S)]-3-[2-Azido-3-cyclopentyl)-1-oxopropyl]-4-(phenylmethyl)-2-oxazolidinone Following the procedure described in Example 46 for the preparation of the corresponding cyclooctyl derivative, 2.1 g of S)-3-[3-cyclopentyl-1-oxopropyl]-4-(phenylmethyl)-2-oxazolidinone and 2.5 g of 2,4,6-triisopropylbenzenesulfonyl azide yielded 1.23 g of [4S-3-(2S)]-3-[2-azido-3-cyclopentyl)-1-oxopropyl]-4-(phenylmethyl)-2-oxazolidinone.

EXAMPLE 51

[4S-3-(2S)]-3-[3-Cyclopentyl-2-[[(1,1-dimethylethoxy)-carbonyl]amino]-1-oxopropyl]-4-(phenylmethyl)-2-oxazolidinone Following the procedure described in Example 47 for the preparation of the corresponding cyclooctyl derivative, 2.7 g of 4S-3-(2S)]-3-[2-azido-3-cyclopentyl)-1-oxopropyl]-4-(phenylmethyl)-2-oxazolidinone was hydrogenated in the presence of 4.0 g of di-tert-butyldicarbonate to give 4.6 g of [4S-3-(2S)]-3-[3-cyclopentyl-2-[[(1,1-dimethylethoxy)-carbonyl]amino]-1-oxopropyl]-4-(phenylmethyl)-2-oxazolidinone, $[\alpha]_D^{25} + 90.74°$.

EXAMPLE 52

(S)-α-[[(1,1-Dimethylethoxy)carbonyl]amino]cyclopentanepropanoic acid

Following the procedure described in Example 48 for the preparation of the corresponding cyclooctyl derivative, 4.57 g of [4S-3-(2S)]-3-[3-cyclopentyl-2-[[(1,1-dimethylethoxy)carbonyl]amino]-1-oxopropyl]-4-(phenylmethyl)-2-oxazolidinone was hydrolyzed with 5.5 mL of 30% $H_2O_2$ and 1.05 g of lithium hydroxide to give 2.8 g of (S)-a-[[(1,1-dimethylethoxy)carbonyl]amino]cyclopentanepropanoic acid, $[\alpha]_D^{25} - 5.46°$. A 200-mg sample was converted to its dicyclohexylamine salt with 180 mg of dicyclohexylamine in ether (8 mL). The dicyclohexylamine salt, 220 mg, was recrystallized from cyclohexane to give pure (S)-α-[[(1,1-dimethylethoxy)carbonyl]amino]cyclopentanepropanoic acid, cyclohexylamine salt, as a white solid, mp 155°–156° C., $[\alpha]_D^{25} + 3.44°$

EXAMPLE 53

4-(1,1-Dimethylethyl)cyclohexanemethanol

To a solution of 4-tert-butylcyclohexane carboxylic acid (10.0 g, 54.3 mmol of a mixture of cis and trans isomers) in anhydrous THF (distilled over Na/benzophenone) (44 mL) at 0° C., under argon were added dropwise $B_2H_6$ in THF (66.5 mL of 0.98M, 65.2 mmol). The reaction mixture was stirred at 0° C. for 2 hrs and then placed in the freezer overnight. The reaction was quenched by addition of saturated NaCl solution (50 mL) and was concentrated. The aqueous residue was extracted with EtOAc (3×200 mL) and the combined organic extracts were washed with sat. $NaHCO_3$ solution (250 mL), followed by saturated brine (250 mL), dried over $Na_2SO_4$, and filtered. Concentration to dryness yielded 9.96 g of crude product which was purified via flash chromatography eluting with 25% EtOAc in hexane to yield an amorphous 4-(1,1-dimethylethyl)cyclohexanemethanol (9.18 g, 53.9 mmol) as a mixture of cis and trans isomers in 99% yield.

EXAMPLE 54

4-(1,1-Dimethylethyl)cyclohexanecarboxaldehyde

To a solution of 4-(1,1-dimethylethyl)cyclohexanemethanol (1.0 g, 5.9 mmol) in $CH_2Cl_2$ (distilled from $CaH_2$) (43 mL) were added at room temperature under argon anhydrous NaOAc (3.84 g, 46.8 mmol). After stirring at room temperature for 5 minutes pyridinium chlorochromate (3.84 g, 17.8 mmol) was added and after stirring for 1 h at room temperature, the reaction was quenched by addition of ethyl ether (200 mL). The crude reaction was filtered through a Fluorasil column to give crude 4-(1,1-dimethylethyl)cyclohexanecarboxaldehyde (0.862 g, 5.12 mmol) as a mixture of trans and cis isomer in 87% yield.

EXAMPLE 55 trans-4-(1,1-Dimethylethyl)cyclohexanecarboxaldehyde

To a solution of the 4-(1,1-dimethylethyl)cyclohexanecarboxaldehyde (862 mg, 5.12 mmol) as obtained above in $CH_3OH$ (44 mL) at room temperature was added dropwise sodium methoxide (1.44 mL of 25% by weight, ~4.73M, 6.29 mmol). After stirring for 3 hrs at room temperature, the reaction was quenched by addition of glacial HOAc-ether (1:3) dropwise until the pH was 6–7 followed by addition of a few drops of sat. $NaHCO_3$. The $CH_3OH$ was removed under reduced pressure and the residue was partitioned between EtOAc (200 mL deoxygenated by passage of argon) and brine (40 mL). The aqueous layer was extracted with EtOAc (50 mL) and the combined organic extracts were dried ($Na_2SO_4$) and concentrated to give crude product (1.6 g). Purification by flash chromatography, eluting with 25% EtOAc/hexane gave trans-4-(1,1-dimethylethyl)cyclohexanecarboxaldehyde (690 mg, 4.1 mmol) in 80% yield.

EXAMPLE 56 trans-(E)-3-[4-(1,1-Dimethylethyl)cyclohexyl]-2-propenoic acid ethyl ester

To a solution of trans-4-(1,1-dimethylethyl)cyclohexanecarboxaldehyde (200 mg, 1.19 mmol) in abs. EtOH (5.4 mL) at room temperature was added triethyl phosphonoacetate (96% pure, 0.389 mL, 1.96 mmol). The reaction mixture was warmed to 40° C. and a solution of sodium ethoxide (prepared from 41 mg of Na in 1.49 mL of abs. EtOH, 1.78 mmol) was added dropwise. The reaction mixture was stirred at 40° C. for 1.6 h and was quenched by the addition of HOAc/ether (1:3) to pH 6 followed by few drops of sat. $NaHCO_3$. The excess EtOH was removed under reduced pressure and the residue was partitioned between ethyl ether (150 mL) and $H_2O$ (50 mL). The aqueous layer was extracted with ether (2×50 mL). The combined ether layers were washed with brine (75 mL), dried over $MgSO_4$ and concentrated to give crude product (300 mg). Purification by flash chromatography eluting with 2% EtOAc/hexane yielded trans-(E)-3-[4-(1,1-dimethylethyl)cyclohexyl]-2-propenoic acid ethyl ester (239 mg, 1.00 mmol) in 84% yield.

EXAMPLE 57 trans-4-(1,1-Dimethylethyl)cyclohexanepropanoic acid ethyl ester.

A suspension of trans-(E)-3-[4-(1,1-dimethylethyl)cyclohexyl]-2-propenoic acid ethyl ester (3.6 g, 15.1 mmol) in abs. EtOH (388 mL) and 5% Pd/C (1.4 g) was hydrogenated at 1 atm for 2 h. The catalyst was filtered over Celite and the filtrate and washings were concentrated to dryness to give trans-4-(1,1-dimethylethyl)cyclohexanepropanoic acid ethyl ester (3.58 g, 14.9 mmol) in 99% yield.

EXAMPLE 58 trans-4-(1,1-Dimethylethyl)cyclohexanepropanoic acid

To a stirring solution of trans-4-(1,1-dimethylethyl)cyclohexanepropanoic acid ethyl ester (3.58 g, 14.9 mmol) in $CH_3OH$ (198 mL) at 0° C. were added 10% KOH/MeOH (46 mL), followed by $H_2O$ (30 mL). The mixture was stirred at room temperature 5 h, then diluted with $H_2O$ (20 mL) and concentrated. The residue was diluted with $H_2O$ (20 mL) and ice chips and the mixture was acidified to pH 2 with 3N HCl. The aqueous solution was extracted with ethyl ether (4×150 mL). The combined organic extracts were washed with brine (200 mL), dried ($Na_2SO_4$) and concentrated to give crystalline trans-4-(1,1-dimethylethyl)cyclohexanepropanoic acid (3.09 g, 14.5 mmol) in 98% yield mp 105°–107° C.

EXAMPLE 59 trans-(S)-3-[3-[4-(1,1-Dimethylethyl)cyclohexyl]-1-oxopropyl]-4-(phenylmethyl)-2-oxazolidinone In a manner analogous to that described in example 5, 2.50 g (11.8 mmol) of trans-4-(1,1-dimethylethyl)cyclohexanepropanoic acid was converted to 3.61 g (9.70 mmol) of trans-(S)-3-[3-[4-(1,1-dimethylethyl)cyclohexyl]-1-oxopropyl]-4-(phenylmethyl)-2-oxazolidinone in 82% yield as a solids, mp 132°–135° C. $[\alpha]_D^{25}+43.2°$ (c 1.0, $CHCl_3$).

EXAMPLE 60 trans-[4S-3-(2S)[-3-[2-Azido-3-[4-(1,1-dimethylethyl)cyclohexyl[-1-oxopropyl]-4-(phenylmethyl)-2-oxazolidinone In a manner analogous to that described in example 6, 3.23 g (8.70 mmol) of trans-(S)-3-[3-[4-(1,1-dimethylethyl)cyclohexyl]-1-oxopropyl]-4-(phenylmethyl)-2-oxazolidinone was converted to 2.45 g (5.04 mmol) of trans-[4S-3-(2S)]-3-[2-azido-3-[4-(1,1-dimethylethyl)cyclohexyl]-1-oxopropyl]-4-(phenylmethyl)-2-oxazolidinone in 58% yield.

EXAMPLE 61 trans-[4S-3-(2S)]-3-[2-[[(1,1-Dimethylethoxy)carbonyl]amino]-3-[4-(1,1-dimethylethyl)cyclohexyl]-1-oxopropyl]-4-(phenylmethyl)-2-oxazolidinone In a manner analogous to that described in example 7, 2.45 g (5.04 mmol) of trans-[4S-3-(2S)]-3-[2-azido-3-[4-(1,1-dimethylethyl)cyclohexyl]-1-oxopropyl]-4-(phenylmethyl)-2-oxazolidinone was converted to 2.46 g (5.07 mmol) of trans-[4S-3-(2S)]-3-[2-[[(1,1-dimethylethoxy)carbonyl]amino]-3-[4-(1,1-dimethylethyl)cyclohexyl]-1-oxopropyl]-4-(phenylmethyl)-2-oxazolidinone in quantitative yield as a solid, mp 144°–145° C.

EXAMPLE 62 trans-(S)-α-[[(1,1-Dimethylethoxy)carbonyl]amino)]-4-(1,1-dimethylethyl)cyclohexane-propanoic acid In a manner analogous to that described in example 8, 2.47 g (5.04 mmol) of trans-[4S-3-(2S)]-3-[2-[[(1,1-dimethylethoxy)carbonyl]amino]-3-[4-(1,1-dimethylethyl)cyclohexyl]-1-oxopropyl]-4-(phenylmethyl)-2-oxazolidinone was converted to 1.62 g (4.95 mmol) of trans-(S)-α-[[(1,1-dimethylethoxy)carbonyl]amino]-4-(1,1-dimethylethyl)cyclohexanepropanoic acid in 98% yield as a glass. $[\alpha]_D^{25}-3.27°$ (c 0.89, $CHCl_3$).

EXAMPLE 63

(E)-3-(5,6,7,8-Tetrahydro-2-naphthylene)-2-propenoic acid ethyl ester

In a manner analogous to that described in example 10, 1.74 g (10.9 mmol) of (5,6,7,8-tetrahydronaphthylene-2-carboxaldehyde was converted to 2.10 g (8.96 mmol, 82%) of (E)-3-(5,6,7,8-tetrahydro-2-naphthylene)-2-propenoic acid ethyl ester as an oil.

EXAMPLE 64

3-(5,6,7,8-Tetrahydro-2-naphthylene)propanoic acid ethyl ester

In a manner analogous to that described in example 11, 2.07 g (8.83 mmol) of (E)-3-(5,6,7,8-tetrahydro-2-naphthylene)-2-propenoic acid ethyl ester was converted to 1.91 g (8.22 mmol, 93%) of 3-(5,6,7,8-tetrahydro-2-naphthylene)propanoic acid ethyl ester an oil.

EXAMPLE 65

3-(5,6,7,8-Tetrahydro-2-naphthylene)propanoic acid

In a manner analogous to that described in example 12, 1.88 g (8.09 mmol) of 3-(5,6,7,8-tetrahydro-2-naphthylene)propanoic acid ethyl ester was converted to 1.64 g (8.03 mmol, 99%) of 3-(5,6,7,8-tetrahydro-2-naphthylene)propanoic acid, mp 80°–82° C.

EXAMPLE 66

(S)-3-[3-(5,6,7,8-Tetrahydro-2-naphthyl)-1-oxopropyl]-4-(phenylmethyl)-2-oxazolidinone In a manner analogous to that described in example 5, 1.58 g (7.73 mmol) of 3-(5,6,7,8-tetrahydro-2-naphthylene)propanoic acid was converted to 2.31 g (6.36 mmol, 82%) of (S)-3-[3-(5,6,7,8-tetrahydro-2-naphthyl)-1-oxopropyl]-4-(phenylmethyl)-2-oxazolidinone, mp 92°–93° C. $[\alpha]_D^{25}+55.3°$ (c 0.57, $CHCl_3$).

EXAMPLE 67

[4S-3-(2S)]-3-[2-Azido-3-(5,6,7,8-tetrahydro-2-naphthyl)-1-oxopropyl]-4-(phenylmethyl)-2-oxazolidinone In a manner analogous to that described in example 6, 2.28 g (6.27 mmol) of (S)-3-[3-(5,6,7,8-tetrahydro-2-naphthyl)-1-oxopropyl]-4-(phenylmethyl)-2-oxazolidinone was converted to 1.82 g (4.52 mmol, 75%) of [4S-3-(2S)]-3-[2-azido-3-(5,6,7,8-tetrahydro-2-naphthyl)-1-oxopropyl]-4-(phenylmethyl)-2-oxazolidinone as a glass. $[\alpha]_D^{25}+80.3°$ (c 0.41, $CHCl_3$).

EXAMPLE 68

[4S-3-(2S)]-3-[[(1,1-dimethylethoxy)carbonyl]amino]-3-(5,6,7,8-tetrahydro-2-naphthyl)-1-oxopropyl]-4-(phenylmethyl)-2-oxazolidinone In a manner analogous to that described in example 7, 3.89 g (9.62 mmol) of [4S-3-(2S)]-3-[2-azido-3-(5,6,7,8-tetrahydro-2-naphthyl)-1-oxopropyl]-4-(phenylmethyl)-2-oxazolidinone was converted to 4.23 g (8.84 mmol, 92%) of [4S-3-(2S)]-3-[2-[[(1,1-dimethylethoxy)carbonyl]amino]-3-(5,6,7,8-tetrahydro-2-naphthal)-1-oxopropyl]-4-(phenylmethyl)-2-oxazolidinone, mp 141°–143° C. $[\alpha]_D^{25} +78.0°$ (c 0.57, CHCl$_3$).

EXAMPLE 69

(S)-α-[[(1,1-dimethylethoxy)carbonyl]amino]-5,6,7,8-tetrahydro-2-naphthalenepropanoic acid In a manner analogous to that described in example 8, 4.23 g (8.84 mmol) of [4S-3-(2S)]-3-[2-[[(1,1-dimethylethoxy)carbonyl]amino]-3-(5,6,7,8-tetrahydro-2-naphthyl)-1-oxopropyl]-4-(phenylmethyl)-2-oxazolidinone was converted to 2.80 g (8.75 mmol, 99%) of (S)-α-[[(1,1-dimethylethoxy)carbonyl]amino]-5,6,7,8-tetrahydro-2-naphthalenepropanoic acid as a glass. $[\alpha]_D^{25} +17.6°$ (c 0.49, CH$_3$OH).

EXAMPLE 70

Preparation of Ac-Tyr(SO$_3$H)-Met-Gly-Trp-Met-Asp-tert-butylalanine-NH$_2$

Boc-tert-butylalanine (500 mg, 2 mmol) and HOBt (405 mg, 3 mmol) were dissolved in a mixture of 20 mL CH$_2$Cl$_2$ and 20 mL DMF chilled to 0° C. and with stirring (412 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of tert-butylalanine per gram of resin.

1 g (0.41 mmol) of Boc-tert-butyl Ala-BHA resin was then subjected to sequential solid phase synthesis using the Boc protocol. All couplings were performed using the DCC/HOBt procedure. At step 16 the Boc-amino acid, DCC and HOBt, were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL acetic anhydride, 10 mL pyridine in methylene chloride for 60 min yielded 1.5 g of Ac-Tyr(2,6-dichlorobenzyl)-Met-Gly-Trp(For)-Met-Asp(OBzl)-tert-butylalanine-BHA-resin. 1.5 g of the resin was cleaved by treatment with 7 mL of HF containing 3 mL of anisole, 1.0 mL of EDT and 20 mL of dimethylsulfide for 1 h at 0° C. After evaporation to a low volume, fresh anhydrous HF (28 mL) was distilled into the reaction vessel for a second treatment for 2 h at 0° C. After thorough evaporation, the resin was washed with 2 volumes of ethylacetate, then triturated with 4×20 mL of 30% acetic acid, filtered and lyophilized to yield 250 mg of crude peptide. 125 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 31 mg (16%) of Ac-Tyr-Met-Gly-Trp-Met-Asp-tert-butyl-Ala-NH$_2$. This material was homogeneous by HPLC and gave the correct amino acid analysis and MS. Amino acid analysis: Asp 1.00 (1), Gly 0.93 (1), Met 2.03 (2), tert-butylalanine 1.03 (1), Tyr 1.00 (1), Trp 0.96 (1). Empirical formula: C$_{45}$H$_{63}$N$_9$O$_{11}$S$_2$; M.W. 970.20.

To a suspension of 30 mg unsulfated peptide in 3 mL of dry pyridine, there was added 240 mg of pyridinium acetyl sulfate. The reaction mixture was stirred for 18 hours at room temperature, then diluted with 5 mL of 1.5M NH$_4$OH and lyophilized. Purification was achieved by preparative HPLC on an ES Industries C-18 10μ column (1×30) cm using a linear gradient (60 min) of 10 to 40% 0.01M NH$_4$Ac/CH$_3$CN at a flow rate of 6 mL/min detection at 290 nm. The main peak was collected and lyophilized to yield 12 mg (38%) of Ac-Tyr(SO$_3$H)-Met-Gly-Trp-Met-Asp-tert-butylalanine-NH$_2$ monoammonium salt. This material was homogeneous by HPLC, gave the correct amino acid analysis and IR. Empirical formula: C$_{45}$H$_{62}$N$_9$O$_{14}$S$_3$; 1:1 NH$_4^+$; M.W. 1067.19.

EXAMPLE 71

Desamino-Phe(4-CH$_2$COOH)-Met-Gly-Trp-Met-Asp-Cyclohexylalanine-NH$_2$ 1.0 g (0.43 mmol/g) of Fmoc-PAL-resin was deprotected with 20% piperidine/DMF (step 1–6) using the Fmoc protocol and coupled to Fmoc-cyclohexylalanine (850 mg, 1.5 mmol) dissolved in 20 mL DMF using DCC (310 mg, 1.5 mmol) and HOBt (270 mg, 2 mmol) which were dissolved in 30 mL of DMF/CH$_2$Cl$_2$ (1:1) by volume and allowed to react for 60 min at room temperature then washed step (8–16) using the Fmoc-protocol to give Fmoc-cyclohexylalanine-PAL-resin. This was subjected to sequential solid phase synthesis using the Fmoc-protocol. All couplings except the last residue were performed using DCC/HOBt procedures. At step 7 the Fmoc-amino acid, DCC and HOBt were added with the corresponding reaction times as follows: Fmoc-Asp(OtBu)-OH (615 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. Fmoc-Met-OH (550 mg, 1.5 mmol), DCC (310 mg, 1.5 mmol) and HOBt (270 mg, 2 mmol) were dissolved in 320 mL of 1:1 by volume DMF/$CH_2Cl_2$ and allowed to couple for 60 min at room temperature. Fmoc-Trp-OH (650 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature.

Fmoc-Gly-OH (450 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. Fmoc-Met-OH (550 mg, 1.5 mmol), DCC (310 mg, 1.5 mmol) and HOBt (270 mg, 2 mmol) were dissolved in 20 mL of 1:1 by volume of DMF/$CH_2Cl_2$ and allowed to couple for 60 min at room temperature. At this point the Fmoc-Met-Gly-Trp-Met-Asp(OtBu)-cyclohexylalanine-PAL-resin was suspended and shaken in 20% piperidine/DMF (step 1-6) using the Fmoc-protocol and coupled to compound [desamino-Phe(4-$CH_2COOH$)-ONSu] (610 mg, 2 mmol) which was dissolved in 20 mL of DMF/$CH_2Cl_2$ (1:1) by volume and allowed to couple for 6 h at room temperature, then washed (step 8-16) and dried to yield 1.4 g of desamino-Phe(4-$CH_2COOH$)-Met-Gly-Trp-Met-Asp(OtBu)-cyclohexylalanine-PAL-resin. This peptidyl-resin was suspended and shaken in 50 mL of TFA/$CH_2Cl_2$/EDT (14/5/1) by volume for 1 h at room temperature. Then the PAL-resin was filtered off and washed with 20 mL TFA $CH_2Cl_2$ (1:1) by volume. The combined filtrates were concentrated to dryness, precipitated with ether filtered off and dried to yield 285 mg of crude peptide. 100 mg of the crude peptide was purified by preparative HPLC on a (2.3×3.0) cm micro Bondapack C-18 column. The peptide was eluted with a linear gradient of 5 to 65% of 0.022% TFA/$CH_3CN$ at a flow rate of 8 mL/min; detection at 280 nm. The main peak was collected and lyophilized to yield 17 mg (11.4%) of desamino-Phe(4-$CH_2COOH$)-Met-Gly-Trp-Met-Asp-cyclohexylalanine-$NH_2$. This material was homogeneous by HPLC and gave the correct amino acid analysis and MS. Amino acid analysis: Asp 1.07 (1), Gly 1.00 (1), Met 2.00 (2), cyclohexylalanine 1.00 (1), Trp n.d. Empirical formula: $C_{47}H_{64}N_8O_{11}S_2$; M.W. 981.20.

EXAMPLE 72

Preparation of Desamino-Phe(4-Tetrazole)-Lys—Gly—Trp—Met—Asp-Cyclohexylalanine-$NH_2$
(with cyclization between Lys and Asp)

Boc-cyclohexylalanine (540 mg, 2 mmol) and HOBt (405 mg, 3 mmol) were dissolved in a mixture of 20 mL $CH_2CL_2$ and 20 mL DMF chilled to 0° C. and with stirring (412 mg, 2 mmol) DCC was added and the mixture was stirred for 60 min at 0° C. Separately 1 g of benzhydrylamine resin (0.41 mmol/g) was treated in the same manner as described in Example 1 and coupled to the in in situ formed Boc-cyclohexylalanine-HOBt ester for 24 hours at room temperature. The resin was then filtered and washed with methylene chloride, dimethylformamide, isopropanol, methylene chloride and dried under high vacuum. Amino acid analysis showed that the resin contained 0.41 mmoles of cyclohexylalanine per gram of resin.

1 g (0.41 mmol/g) of Boc-cyclohexylalanine-BAH resin was suspended and shaken in TFA/$CH_2Cl_2$ (1:1) by volume (3×40 mL) 10 min each time to remove the Boc group. The product was isolated by filtration and washed (3×50 mL each) with $CH_2Cl_2$, 8% DIEA in $CH_2Cl_2$ and $CH_2Cl_2$ to give the free base of cyclohexylalanine-BHA resin. This was subjected to sequential solid phase peptide synthesis using the Fmoc-protocol. All couplings except the last residue were performed using DCC/HOBt procedure. At step 7 the Fmoc amino acid, DCC and HOBt were added with the corresponding times as follows: Fmoc-Asp(OtBu)-OH (615 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. Fmoc-Met-OH (550 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. Fmoc-Trp-OH (650 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature.

Fmoc-Gly-OH (450 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. Fmoc-Lys(Boc)-OH (720 mg, 1.5 mmol), DCC (310 mg, 1.5 mmol) and HOBt (270 mg, 2 mmol) were dissolved in 20 mL of 1:1 by volume DMF/$CH_2Cl_2$ and allowed to couple for 60 min at room temperature. At this point the peptide-resin was dried under high vacuum to provide 1.32 g of Fmoc-Lys(Boc)-Gly-Trp-Met-Asp(OtBu)-Cyclohexylalanine-BHA resin. This peptidyl resin was suspended and shaken in 50% TFA/$CH_2Cl_2$ with 1% EDT (2×20 mL) 10 min each time at room temperature to remove the OtBu and the Boc groups. The peptidyl-BHA resin was then neutralized with 8% DIPEA in $CH_2Cl_2$, washed (3×50 mL) each with $CH_2Cl_2$, DMF, methanol, and isolated by filtration to yield Fmoc-Lys-Gly-Trp-Met-Asp-cyclohexylalanine-BHA resin. The cyclization on the resin between the ε-amino group of Lys and the β-carboxyl group of Asp was achieved using the BOP reagent (1.0 g, 2 mmol) in DMF (20 mL) containing 1.5% DIEA for 48 h. A negative Kaiser test was observed and the peptide-resin was washed and dried to yield Fmoc-Lys—Gly—Trp—Met—Asp-Cyclohexylalanine-BHA resin.
(with cyclization between Lys and Asp)

The resin was deprotected with 20% piperidine/DMF (step 1-6) using the Fmoc protocol and coupled to 5-[4-[(2-carboxy)ethyl]phenyl]-2-(1,1-dimethylethyl)-2H-tetrazole (475 mg, 1.5 mmol), DCC (310 mg, 1.5 mmol) and HOBt (270 mg, 2 mmol) which were dissolved in 50 mL of DMF/$CH_2Cl_2$ (1:1) by volume and allowed to react for 60 min at room temperature then washed (step 8-16) and dried to yield 1.4 g of Desamino-Phe(4-Tetrazole-tBu)-Lys—Gly—Trp—Met—Asp-Cyclohexylalanine-BHA resin.

1.4 g of the resin was cleaved by treatment with HF using the same condition as described in Example 1 to yield 428 mg of crude peptide. 200 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 16 mg (8.8%) of Desamino-Phe(4-Tetrazole)-Lys—Gly—Trp—Met—Asp-Cyclohexylalanine-NH$_2$.

This material was homogeneous by HPLC and gave the correct amino acid analysis and MS. Amino acid analysis: Asp 0.85 (1), Gly 1.00 (1), Met 1.00 (1), Lys+-cyclohexyl-Ala 1.80 (2). Empirical formula: C$_{47}$H$_{63}$N$_{13}$O$_8$S; M.W. 970.17.

EXAMPLE 73

Preparation of Ac-Tyr(SO$_3$H)-Met-Gly-(2)Nal-Met-Asp-Cyclohexylalanine-NH$_2$ 1 g (0.41 mmol/g) of Boc-cyclohexylalanine-BHA resin prepared as in Example (72) was subjected to sequential solid phase synthesis using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-(2)Nal-OH (480 mg, 1.5 mmol), DCC (310 mg, 1.5 mmol) and HOBt (270 mg, 2 mmol) were dissolved in 20 mL of DMF and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2-6-dichlorobenzyl-tyrosine (660 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Deprotection of the Boc-protecting group and acetylation of the resin with 10 mL acetic anhydride, 10 mL pyridine in methylene chloride for 60 min yielded 1.5 g of Ac-Tyr(2,6-dichlorobenzyl)-Met-Gly-(2)Nal-Met-Asp-(OBzl)-Cyclohexylalanine-BHA resin.

1.5 g of the resin was cleaved by treatment with 10 mL of HF containing 2.5 mL of anisole, and 20 mL of dimethylsulfide for 1 h at 0° C. After evaporation to a low volume, fresh anhydrous HF (30 mL) was distilled into the reaction vessel for a second treatment for 2 h at 0° C. After thorough evaporation the resin was washed with 2 volumes of ethylacetate, triturated with 4×20 mL of 30% acetic acid, filtered and lyophilized to yield 240 mg of crude peptide. 100 mg of the crude peptide was purified by preparative HPLC on a (2.3×30) cm micro Bondapack C-18 column the peptide was eluted with a linear gradient (4 h) of 5 to 65% 0.022% TFA/CH$_3$CN at a flow rate of 8 mL/min; detection at 280 nm. The main peak was collected and lyophilized to yield 19 mg (11%) of Ac-Tyr-Met-Gly-(2)Nal-Met-Asp-Cyclohexylalanine-NH$_2$. This material was homogeneous by HPLC and gave the correct amino acid analysis and MS. Amino acid analysis: Asp 1.05 (1), Gly 1.00 (1), Met 2.10 (2), Tyr 1.00 (1), cyclohexylalanine 1.07, (2) Nal n.d. Empirical formula: C$_{49}$H$_{66}$N$_8$O$_{11}$S$_2$; M.W. 1007.23. To a suspension of 19 mg unsulfated peptide in 2 mL of dry pyridine, there was added 430 mg of pyridinium acetyl sulfate. The reaction mixture was stirred for 18 h at room temperature then diluted with 5 mL of 1.5M NH$_4$OH and lyophilized. Purification was achieved by preparative HPLC on an ES Industries C-18 10μ column (1×30) cm using a linear gradient (60 min) of 20 to 50% 0.01M NH$_4$Ac/CH$_3$CN of a flow rate of 6 mL/min; detection at 278 nm. The main peak was collected and lyophilized to yield 12 mg (57%) of Ac-Tyr(SO$_3$H)-Met-Gly-(2)Nal-Met-Asp-Cyclohexylalanine-NH$_2$ monoammonium salt. This material was homogeneous in HPLC and gave the correct amino acid analysis and IR. C$_{49}$H$_{65}$N$_8$O$_{14}$S$_3$ 1:1 NH$_4$+; M.W. 1104.32.

EXAMPLE 74

Preparation of Ac-Tyr(SO$_3$H)-Met-Gly-Trp-Met-Asp-(2)Nal-NH$_2$ 1 g of Boc-(2)Nal-PAM resin (substitution 0.41 mmol/g), prepared according to the procedure of Merrifield et al., *J. Am. Chem. Soc.* 1976 98, 7357–7362 was subjected to sequential solid phase synthesis using the Boc-protocol. All couplings were performed using DCC/HOBt procedure. At step 16, the Boc-amino acid, DCC and HOBt were added with the corresponding reaction times as follows: Boc-Asp(OFm)-OH (616 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Tyr-OH (420 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-group and acetylation of the resin with 10 mL of acetic anhydride, 10 mL of pyridine in methylene chloride for 60 min yielded 1.4 g of Ac-Tyr-Met-Gly-Trp(For)-Met-Asp(OFm)-(2)Nal-PAM resin. This resin was treated with 20% piperidine/DMF (step 1-6) using the Fmoc-protocol to yield Ac-Tyr-Met-Gly-Trp(For)-Met-Asp-(2)Nal-PAM resin. The peptidyl-PAM resin was then placed in a pressure bottle, suspended in 100 mL of methanol saturated with NH$_3$ at −20° C. and sealed. The suspension was stirred at room temperature for 3 days. After venting the excess NH$_3$, the PAM-resin was filtered off and washed with methanol. The combined filtrates were concentrated to dryness to give 310 mg of crude peptide.

150 mg of the crude peptide was purified by preparative HPLC on a (2.3×30) cm micro Bondapak C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 60 mg (28% of Ac-Tyr-Met-Gly-Trp-Met-Asp-(2)Nal-NH$_2$. This material was homogeneous by HPLC and gave the correct amino acid analysis and MS. Amino acid analysis: Asp 1.01 (1), Gly 0.95 (1), Met 1.90 (2), Tyr 0.95 (1), Trp 0.75 (1), (2)Nal n.d. Empirical formula: C$_{51}$H$_{61}$N$_9$O$_{11}$S$_2$ 1040.24.

To a suspension of 60 mg of unsulfated peptide in 5 mL of dry pyridine, there was added 610 mg of pyridinium acetyl sulfate. The reaction mixture was stirred for 4 hours at room temperature then diluted with 15 mL of 1.5M NH$_4$OH and lyophilized. Purification was achieved by preparative HPLC on an ES Industries C-18 10μ column (1×30) cm using a linear gradient (60 min) 20 to 50% 0.01M NH$_4$Ac/CH$_3$CN at a flow rate of 6 mL/min; detection at 290 nm. The main peak was collected and lyophilized to yield 22 mg (33%) of Ac-Tyr(SO$_3$H)-Met-Gly-Trp-Met-Asp-(2)Nal-NH$_2$ monoammonium salt. This material was homogeneous by HPLC, gave the correct amino acid analysis and IR. Empirical formula: C$_{51}$H$_{60}$N$_9$O$_{14}$S$_3$ 1:1 NH$_4^+$; M.W. 1137.33.

EXAMPLE 75

Preparation of
Ac-Tyr(SO$_3$H)-Met-Gly-Trp-Met-Asp-Cyclopentylalanine-NH$_2$

Boc-cyclopentylalanine [(S)-α-[[(1,1-dimethylethoxy)carbonyl]amino]cyclopentanepropanoic acid] (520 mg, 2 mmol) and HOBt (405 mg, 3 mmol) were dissolved in a mixture of 20 mL CH$_2$Cl$_2$ and 20 mL DMF chilled to 0° C. and with stirring (410 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of cyclopentylalanine per gram of resin.

1 g (0.41 mmol) of Boc-cyclopentylalanine-BHA resin was then subjected to sequential solid phase synthesis using the Boc protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.68 g of Ac-Tyr(2,6-dichlorobenzyl)-Met-Gly-Trp(For)-Met-Asp(OBzl)-cyclopentylalanine-BHA resin. 1.68 of the resin was cleaved by treatment with 9 mL of HF containing 4 mL of anisole, 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, triturated with 4×20 mL of 30% acetic acid, filtered and lyophilized to yield 400 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 12 mg (12%) of Ac-Tyr-Met-Gly-Trp-Met-Asp-Cyclopentylalanine-NH$_2$. This material was homogenous by HPLC and gave the correct amino acid analysis and MS. Amino acid analysis: Asp 1.00 (1), Gly 1.00 (1), Met 1.99 (2), Tyr 1.00 (1), Trp 0.82 (1), cyclopentylalanine n.d. Empirical formula: C$_{46}$H$_{63}$N$_9$O$_{11}$S$_2$; M.W. 982.21.

To a suspension of 12 mL unsulfated peptide in 2 mL of dry pyridine, there was added 355 mg of pyridinium acetyl sulfate. The reaction mixture was stirred for 5 hours at room temperature, diluted with 5 mL of 1.5M NH$_4$OH and lyophilized. Purification was achieved by preparative HPLC on an ES Industries C-18 10μ column (1×30) cm using (60 min) at 10 to 50% 0.01M NH$_4$Ac/CH$_3$CN at a flow rate of 6 mL/min; detection at 290 nm. The main peak was collected and lyophilized to yield 8 mg (62%) of Ac-Tyr(SO$_3$H)-Met-Gly-Trp-Met-Asp-cyclopentylalanine-NH$_2$ monoammonium salt. This material was homogenous by HPLC, gave the correct amino acid analysis and IR. Empirical formula: C$_{46}$H$_{62}$N$_9$O$_{14}$S$_3$ 1:1 NH$_4$+; M.W. 1079.

EXAMPLE 76

Preparation of Ac-Tyr(SO$_3$H)-Met-Gly-Trp-Met-Asp-Cyclooctylalanine-NH$_2$

Boc-cyclooctylalanine [(S)-α-[[(1,1-dimethylethoxy)carbonyl]amino]cyclooctanepropanoic acid] (580 mg, 2 mmol) and HOBt (405 mg, 3 mmol) were dissolved in a mixture of 20 mL CH$_2$Cl$_2$ and 20 mL DMF chilled to 0° C. and with stirring (412 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of cyclooctylalanine per gram of resin.

1 g (0.41 mmol) of Boc-cyclooctylalanine-BHA resin was then subjected to sequential solid phase synthesis using the Boc protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.60 g of Ac-Tyr(2,6-dichlorobenzyl)-Met-Gly-Trp(For)-Met-Asp(OBzl)-cyclooctylalanine-BHA resin. 1.60 of the resin was cleaved by treatment with 9 mL of HF containing 4 mL of anisole, 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate then triturated with 4×20 mL of 30% acetic acid, filtered and lyophilized to yield 250 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 15 mg (9%) of Ac-Tyr-Met-Gly-Trp-Met-Asp-Cyclooctylalanine-NH$_2$. This material was homogenous by HPLC and gave the correct amino acid analysis and MS. Amino acid analysis: Asp 0.99 (1), Gly 1.00 (1), Met 2.00 (2), Tyr 1.00 (1), Trp 0.70 (1), cyclooctylalanine n.d. Empirical formula: C$_{49}$H$_{69}$N$_9$O$_{11}$S$_2$; M.W. 1024.29.

To a suspension of 12 mL unsulfated peptide in 2 mL of dry pyridine, there was added 355 mg of pyridinium acetyl sulfate. The reaction mixture was stirred for 5 hours at room temperature then diluted with 5 mL of 1.5M NH$_4$OH and lyophilized. Purification was achieved by preparative HPLC on an ES Industries C-18 10μ column (1×30) cm using (60 min) at 10 to 50% 0.01M NH$_4$Ac/CH$_3$CN at a flow rate of 6 mL/min; detection 290 nm. The main peak was collected and lyophilized to yield 6 mg (40%) of Ac-Tyr(SO$_3$H)-Met-Gly-Trp-Met-Asp-Cyclooctylalanine-NH$_2$ monoammonium salt. This material was homogenous by HPLC, gave the correct amino acid analysis and IR. Empirical formula: C$_{49}$H$_{68}$N$_9$O$_{14}$S$_3$ 1:1 NH$_4$+; M.W. 1121.37.

EXAMPLE 77

Preparation of Ac-Tyr(SO$_3$H)-Met-Gly-Trp-Met-Asp-Cyclohexylmethylalanine-NH$_2$ Boc-cyclohexylmethylalanine [(S)-α-[[(1,1-dimethylethoxy)carbonyl]amino]cyclohexanebutanoic acid] (568 mg, 2 mmol) and HOBt (405 mg, 3 mmol) were dissolved in a mixture of 20 mL CH$_2$Cl$_2$ and 20% mL DMF chilled to 0° C. and with stirring (412 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of cyclohexylmethylalanine per gram of resin.

1 g (0.41 mmol) of Boc-cyclohexylmethylalanine-BHA resin was then subjected to sequential solid phase synthesis using the Boc protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.60 g of Ac-Tyr(2,6-dichlorobenzyl)-Met-Gly-Trp(For)-Met-Asp(OBzl)-Cyclohexylmethylalanine-BHA resin. 1.60 of the resin was cleaved by treatment with 9 mL of HF containing 4 mL of anisole, 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate then triturated with 4×20 mL of 30% acetic acid, filtered and lyophilized to yield 375 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 15 mg (14%) of Ac-Tyr-Met-Gly-Trp-Met-Asp-Cyclohexylmethylalanine-NH$_2$. This material was homogenous by HPLC and gave the correct amino acid analysis and MS. Amino acid analysis: Asp 1.03 (1), Gly 1.06 (1), Met 2.00 (2), Tyr 1.00 (1), Trp+Cyclohexylmethylalanine 2.17. (2). Empirical formula: C$_{48}$H$_{67}$N$_9$O$_{11}$S$_2$; M.W. 1010.20.

To a suspension of 15 mL unsulfated peptide in 2 mL of dry pyridine, there was added 355 mg of pyridinium acetyl sulfate. The reaction mixture was stirred for 5 hours at room temperature then diluted with 5 mL of 1.5M NH$_4$OH and lyophilized. Purification was achieved by preparative HPLC on an ES Industries C-18 10μ column (1×30) cm using (30 min) at 10 to 50% 0.01M NH$_4$Ac/CH$_3$CN at a flow rate of 6 mL/min; detection 290 nm. The main peak was collected and lyophilized to yield 5.5 mg (33%) of Ac-Tyr(SO$_3$H)-Met-Gly-Trp-Met-Asp-Cyclohexylmethylalanine-NH$_2$ monoammonium salt. This material was homogenous by HPLC and gave the correct amino acid analysis and IR. Empirical formula: C$_{48}$H$_{66}$N$_9$O$_{14}$S$_3$ 1:1 NH$_4$+; M.W. 1107.34.

EXAMPLE 78

Preparation of
Ac-Tyr(SO$_3$H)-Met-Gly-Trp-Met-Asp-(D)-Cyclohexylalanine-NH$_2$

Boc-(D)-cyclohexylalanine (540 mg, 2 mmol) and HOBt (405 mg, 3 mmol) were dissolved in a mixture of 20 mL CH$_2$Cl$_2$ and DMF chilled to 0° C. and with stirring (412 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of (D)-cyclohexylalanine per gram of resin.

1 g (0.41 mmol) of Boc-(D)-cyclohexylalanine-BHA resin was then subjected to sequential solid phase synthesis using the Boc protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.60 g of Ac-Tyr(2,6-dichlorobenzyl)-Met-Gly-Trp(For)-Met-Asp-(D)-cyclohexylalanine-BHA resin. 1.60 g of the resin was cleaved by treatment with 9 mL of HF containing 4 mL of anisole, 1.0 mL of EDT and 25 mL of dimethylsulfide for 1 h at 0° C. After evaporation to a low volume, fresh anhydrous HF (32 mL) was distilled for 2 h at 0° C. After thorough evaporation, the resin was washed with 2 volumes of ethylacetate then triturated with 4×20 mL of 30% acetic acid, filtered and lyophilized to yield 315 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 16 mg (12%) of Ac-Tyr-Met-Gly-Trp-Met-Asp-(D)-cyclohexylalanine-NH$_2$. This material was homogenous by HPLC and gave the correct amino acid analysis and MS. Amino acid analysis: Asp 1.00 (1), Gly 1.02 (1), Met 2.01 (2), Tyr 1.01 (1), cyclohexylalanine 1.00 (1), Trp 0.8 (1). Empirical formula: $C_{47}H_{65}N_9O_{11}S_2$; M.W. 996.23.

To a suspension of 16 mL unsulfated peptide in 2 mL of dry pyridine, there was added 360 mg of pyridinium acetyl sulfate. The reaction mixture was stirred for 6 hours at room temperature then diluted with 5 mL of 1.5M $NH_4OH$ and lyophilized. Purification was achieved by preparative HPLC on an ES Industries C-18 10μ column (1×30) cm using a linear gradient (60 min) of 10 to 50% 0.01M $NH_4Ac/CH_3CN$ at a flow rate of 6 mL/min; detection at 290 nm. The main peak was collected and lyophilized to yield 11 mg (65%) of Ac-Tyr($SO_3H$)-Met-Gly-Trp-Met-Asp-(D)-cyclohexyl-Ala-$NH_2$ monoammonium salt. This material was homogenous by HPLC and gave the correct amino acid analysis and IR. Empirical formula: $C_{47}H_{64}N_9O_{14}S_3$ 1:1 $NH_4^+$; M.W. 1093.32.

EXAMPLE 79

Preparation of Ac-Tyr($SO_3H$)-Met-Gly-(2)Nal-Met-Asp-(2)Nal-$NH_2$ 1 g of Boc-(2)Nal-PAM resin (substitution 0.41 mmol/g), prepared according to the procedure of Merrifield et al., *J. Am. Chem. Soc.* 1976 98, 7357–7362 was subjected to sequential solid phase synthesis using the Boc-protocol. All couplings were performed using DCC/HOBt procedure. At step 16 the Boc-amino acid, DCC and HOBt were added with the corresponding reaction times as follows: Boc-Asp(OFm)-OH (616 mg, 1.5 mmol), DCC (310 mg, 1.5 mmol) and HOBt (270 mg, 2 mmol) were dissolved in 20 mL of 1:1 by volume $DMF/CH_2Cl_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-(2)Nal-OH (546 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Tyr-OH (420 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.4 g of Ac-Tyr-Met-Gly-(2)Nal-Met-Asp(OFm)-(2)Nal-PAM resin. This resin was treated with 20% piperidine/DMF (step 1–6) using the Fmoc-protocol to yield Ac-Tyr-Met-Gly-(2)Nal-Met-Asp-(2)Nal-PAM resin. The peptidyl-PAM resin was then placed in a pressure bottle, suspended in 100 mL of methanol saturated with $NH_3$ at −20° C. and sealed. The suspension was stirred at room temperature for 3 days. After venting the excess $NH_3$, the PAM-resin was filtered off and washed with methanol. The combined filtrates were evaporated to dryness to give 300 mg of crude peptide.

150 mg of the crude peptide was purified by preparative HPLC on a (2.3×30) cm micro Bondapack C-18 column. The peptide was eluted with a linear gradient (4 h) of 5 to 65% 0.022% $TFA/CH_3CN$ at a flow rate of 8 mL/min; detection at 280 nm. The main peak was collected and lyophilized to yield 32 mg (15%) of Ac-Tyr-Met-Gly-(2)Nal-Met-Asp-(2)Nal-$NH_2$. This material was homogenous by HPLC and gave the correct amino acid analysis and MS. Amino acid analysis: Asp 0.98 (1), Gly 1.00 (1), Met (1.95 (2), Tyr 0.98 (1), 2-Nal n.d. Empirical formula: $C_{53}H_{62}N_8O_{11}S_2$; M.W. 1051.26.

To a suspension of 16 mL unsulfated peptide in 3 mL of dry pyridine, there was added 320 mg of pyridinium acetyl sulfate. The reaction mixture was stirred for 6 hours at room temperature, diluted with 10 mL of 1.5M $NH_4OH$ and lyophilized. Purification was achieved by preparative HPLC on an ES Industries C-18 10μ column (1×30) cm using a linear gradient 20 to 50% (over 60 min) of 0.01M $NH_4Ac/CH_3CN$ at a flow rate of 6 mL/min; detection at 290 nm. The main peak was collected and lyophilized to yield 7 mg (41%) of Ac-Tyr($SO_3H$)-Met-Gly-(2)Nal-Met-Asp-(2)Nal-$NH_2$ monoammonium salt. This material was homogenous by HPLC and gave the correct amino acid analysis and IR. Empirical formula: $C_{53}H_{61}N_8O_{14}S_3$ 1:1 $NH_4^+$; M.W. 1148.35.

EXAMPLE 80

Preparation of Ac-Tyr($SO_3H$)-Met-Gly-Trp-Met-Asp-(D)-(2)Nal-$NH_2$ 1 g of Boc-(D)-(2)Nal-PAM resin (substitution 0.41 mmol/g), prepared according to the procedure of Merrifield et al., *J. Am. Chem. Soc.* 1976 98, 7357–7362 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OFm)-OH (616 mg, 1.5 mmol), DCC (310 mg, 1.5 mmol) and HOBt (270 mg, 2 mmol) were dissolved in 20 mL of 1:1 by volume $DMF/CH_2Cl_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Tyr-OH (420 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.4 g of Ac-Tyr-Met-Gly-Trp-(For)-Met-Asp(OFm)-(D)-(2)Nal-PAM resin. This resin was treated with 20% piperidine/DMF (step 1-6) using the Fmoc-protocol to yield Ac-Tyr-Met-Gly-Trp(For)-Met-Asp-(D)-(2)Nal-PAM resin. The peptidyl-PAM resin was then placed in a pressure bottle, suspended in 100 mL of methanol saturated with NH$_3$ at $-20°$ C. and sealed. The suspension was stirred at room temperature for 3 days. After venting the excess NH$_3$, the PAM-resin was filtered off and washed with methanol. The combined filtrates were evaporated to dryness to give 300 mg of crude peptide.

150 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 40 mg (19%) of Ac-Tyr-Met-Gly-Trp-Met-Asp-(D)-(2)Nal-NH$_2$. This material was homogenous by HPLC and gave the correct amino acid analysis and MS. Amino acid analysis: Asp 1.01 (1), Gly 1.02 (1), Met 2.00 (2), Tyr 1.00 (1), Trp 0.90 (1), 2-Nal n.d. Empirical formula: $C_{51}H_{61}N_9O_{11}S_2$; M.W. 1040.24.

To a suspension of 40 mg unsulfated peptide in 5 mL of dry pyridine, there was added 610 mg of pyridinium acetyl sulfate. The reaction mixture was stirred for 4 hours at room temperature then diluted with 15 mL of 1.5M NH$_4$OH and lyophilized. Purification was achieved by preparative HPLC on an ES Industries C-18 10$\mu$ column (1×30) cm using a linear gradient (60 min) 20 to 50% 0.01M NH$_4$Ac/CH$_3$CN at a flow rate of 6 mL/min; detection at 290 nm. The main peak was collected and lyophilized to yield 24 mg (56%) of Ac-Tyr(SO$_3$H)-Met-Gly-Trp-Met-Asp-(D)-2-Nal-NH$_2$ monoammonium salt. This material was homogenous by HPLC and gave the correct amino acid analysis and IR. Empirical formula: $C_{51}H_{60}N_9O_{14}S_3$ 1:1 NH$_4^+$; M.W. 1137.33.

EXAMPLE 81

Preparation of Ac-Tyr(SO$_3$H)-Met-Gly-Trp-Met-Asp-(2-Adamantyl)alanine-NH$_2$

Boc-2-adamantyl)alanine [(S)-$\alpha$-[[[(1,1-dimethylethyl)oxy]carbonyl]amino]tricyclo[3.3.1.1-3,7]decane-2-propanoic acid] (650 mg, 2 mmol) and HOBt (405 mg, 3 mmol) were dissolved in a mixture of 20 mL CH$_2$Cl$_2$ and 20 mL DMF chilled to 0° C. and with stirring (412 mg, 2 mmol) DCC was added and the mixture was stirred for 60 minutes at 0° C. Separately 1 g of benzhydrylamine copolysterene 1% divinylbenzene cross-linked resin (0.41 mmol N/g) was washed with 10% diisopropylethylamine in methylene chloride for 30 min, filtered and washed with methylene chloride dimethylformamide and methylene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of (2-adamantyl)alanine per gram of resin.

1 g (0.41 mmol) of Boc-(2-adamantyl)alanine-BHA resin was subjected to sequential solid phase synthesis using the Boc protocol. All couplings were performed using the DCC/HOBt procedure. At step 16 the Boc-amino acid, DCC and HOBt, were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL acetic anhydride, 10 mL pyridine in methylene chloride for 60 min yielded 1.60 g of Ac-Tyr(2,6-dichlorobenzyl)-Met-Gly-Trp(For)-Met-Asp(OBzl)-(2-Adamantyl)alanine-BHA-resin. 1.68 g of the resin was cleaved by treatment with 9 mL of HF containing 4 mL of anisole, 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, then triturated with 4×20 mL of 30% acetic acid, filtered and lyophilized to yield 700 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 15 mg (24%) of Ac-Tyr-Met-Gly-Trp-Met-Asp-(2-Adamantyl)alanine-NH$_2$. This material was homogeneous by HPLC and gave the correct amino acid analysis and MS. Amino acid analysis: Asp 1.01 (1), Gly 1.00 (1), Met 1.90 (2), Tyr 0.99 (1), Trp 0.90 (1) adamantylalanine n.d. Empirical formula: $C_{51}H_{69}N_9O_{11}S_2$; M.W. 1048.31.

To a suspension of 15 mg unsulfated peptide in 2 mL of dry pyridine, there was added 355 mg of pyridinium acetyl sulfate. The reaction mixture was stirred for 5 hours at room temperature, diluted with 5 mL of 1.5M NH$_4$OH and lyophilized. Purification was achieved by preparative HPLC on an ES Industries C-18 10$\mu$ column (1×30) cm using (30 min) of 10 to 50% 0.01M NH$_4$Ac/CH$_3$CN of a flow rate of 6 mL/min; detection at 290 nm. The main peak was collected and lyophilized to yield 9 mg (56%) of Ac-Tyr(SO$_3$H)-Met-Gly-Trp-Met-Asp-(2-Adamantyl)alanine-NH$_2$ monoammonium salt. This material was homogenous by HPLC, gave the correct amino acid analysis and IR. Empirical formula: $C_{51}H_{68}N_9O_{14}S_3$; 1:1 NH$_4^+$; M.W. 1145.39.

EXAMPLE 82

Preparation of
Ac-Tyr(SO$_3$H)-Met-Gly-(2-Benzo[b]thiophenyl)alanine-Met-Asp-Phe-NH$_2$ 1 g of Boc-Phe-PAM resin (substitution 0.58 mmol/g), was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OFm)-OH (1.23 g, 3 mmol), DCC (620 mg, 3 mmol) and HOBt (540 mg, 4 mmol) were dissolved in 40 mL of 1:1 by volume DMF/CH$_2$Cl$_2$, and allowed to couple for 60 min at room temperature. Boc-Met-OH (760 mg, 3 mmol), DCC (620 mg, 3 mmol) and HOBt (540 mg, 2 mmol) were dissolved in 40 mL of 1:1 by volume DMF/CH$_2$Cl$_2$ and allowed to couple for 60 min at room temperature. Boc-Bta-OH [(S)-α-[[(1,1-dimethylethoxy)carbonyl]-amino]benzo[b]thiophene-2-propanoic acid] (966 mg, 3 mmol), DCC (620 mg, 3 mmol) and HOBt (540 mg, 4 mmol) were dissolved in 40 mL of DMF, and allowed to couple for 60 min at room temperature. Boc-Gly-OH (540 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Met-OH (760 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Tyr-OH (840 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature.

Deprotection of the Boc-protecting group and acetylation of the resin with 20 mL of acetic anhydride, 10 mL of pyridine in methylene chloride for 120 min yielded 1.8 g of Ac-Tyr-Met-Gly-Bta-Met-Asp(OFm)-PAM resin. This resin was treated with 20% piperidine/DMF (step 1-16) using the Fmoc-protocol to yield Ac-Tyr-Met-Gly-Bta-Met-Asp-Phe-PAM resin. The peptidyl-PAM resin was then placed in a pressure bottle, suspended in 100 mL of methanol saturated with NH$_3$ at −20° C. and sealed. The suspension was stirred at room temperature for 4 days. After venting the excess NH$_3$, the PAM-resin was filtered off and washed with methanol. The combined filtrates were evaporated to dryness to give 900 mg of crude peptide.

175 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 20 mg (18%) of Ac-Tyr-Met-Gly-Bta-Met-Asp-Phe-NH$_2$. This material was homogenous by HPLC and gave the correct amino acid analysis and MS. Amino acid analysis: Asp 1.00 (1), Gly 0.93 (1), Met 1.90 (2), Tyr 1.00 (1), Phe 1.10 (1), Bta 1.10 (1). Empirical formula: C$_{47}$H$_{58}$N$_8$O$_{11}$S$_3$; M.W. 1007.2.

To a suspension of 20 mg unsulfated peptide in 3 mL of dry pyridine, there was added 420 mg of pyridinium acetyl sulfate. The reaction mixture was stirred for 6 hours at room temperature, diluted with 10 mL of 1.5M NH$_4$OH and lyophilized. Purification was achieved by preparative HPLC on an ES Industries C-18 10μ column (1×30) cm using a linear gradient 20 to 50% (over 60 min) of 0.01M NH$_4$Ac/CH$_3$CN at a flow rate of 6 mL/min; detection at 290 nm. The main peak was collected and lyophilized to yield 12 mg (55%) of Ac-Tyr(SO$_3$H)-Met-Gly-Bta-Met-Asp-Phe-NH$_2$ monoammonium salt. This material was homogenous by HPLC and gave the correct amino acid analysis and IR. Empirical formula: C$_{47}$H$_{57}$N$_8$O$_{14}$S$_4$; 1:1 NH$_4^+$; M.W. 1104.32.

EXAMPLE 83

Preparation of
Desamino-Phe(4-CH$_2$COOH)-Met-Gly-Trp-Met-Asp-Cyclooctylalanine-NH$_2$ 1 g of Boc-cyclooctylalanine [(S)-α-[[(1,1-dimethylethoxy)carbonyl]amino]-cyclooctanepropanoic acid]-PAM resin (substitution 0.41 mmol/g), prepared according to the procedure of Merrifield et al., *J. Am. Chem. Soc.* 1976 98, 7357–7362 was subjected to sequential solid phase synthesis using the Boc-protocol. All couplings except the last residue were performed using the DCC/HOBt procedure. At step 16 the Boc-amino acid, DCC and HOBt were added with the corresponding reaction times as follows: Boc-Asp(OFm)-OH (616 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Finally, [desamino-Phe(4-CH$_2$COOH)-ONSu] (610 mg, 2 mmol) which was dissolved in 20 mL of DMF/CH$_2$Cl$_2$ (1:1) by volume was added and allowed to couple for 6 h at room temperature to yield 1.5 g of desamino-Phe(4-CH$_2$COOH)-Met-Gly-Trp-(For)-Met-Asp(OFm)-cyclooctylalanine-PAM resin. This resin was treated with 20% piperidine/DMF (step 1-6) using the Fmoc-protocol to yield desamino-Phe(4-CH$_2$COOH)-Met-Gly-Trp(For)-Met-Asp-cyclooctylalanine-PAM resin.

The peptidyl-PAM resin was then placed in a pressure bottle, suspended in 100 mL of methanol saturated with NH$_3$ at −20° C. and sealed. The suspension was stirred at room temperature for 3 days. After venting the excess NH$_3$, the PAM-resin was filtered off and washed with methanol. The combined filtrates were evaporated to dryness to give 300 mg of crude peptide. 140 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 12 mg (6%) of desamino-Phe(4-CH$_2$COOH)-Met-Gly-Trp-Met-Asp-cyclooctylalanine-NH$_2$. This material was homogeneous by HPLC and gave the correct amino acid analysis and MS. Amino acid analysis: Asp 1.01 (1), Gly 1.15 (1), Met 1.80 (2), Trp n.d., cyclooctylalanine n.d. Empirical formula: 1009.26; M.W. 1009.26.

EXAMPLE 84

Preparation of Ac-Tyr(SO$_3$H)-Met-Gly-(2)Nal-Met-Asp-Cyclooctylalanine-NH$_2$ 1 g (0.41 mmol) of Boc-cyclooctylalanine[(S)-α-[[(1,1-dimethylethoxy)carbonyl]amino]cyclooctanepropanoic acid]-BHA-resin, prepared as in Example 70 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-(2)Nal-OH (546 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1 g of Ac-Tyr-(2,6-dichlorobenzyl)-Met-Gly-(2)Nal-Met-Asp(OBzl)-cyclooctylalanine-BHA resin 1.54 g of the resin was cleaved with 9 mL of HF containing 4 mL of anisole, 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, triturated with 4×20 mL of 30% acetic acid, filtered and lyophilized to yield 323.0 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 15 mg (11%) of Ac-Tyr-Met-Gly-(2)Nal-Met-Asp-Cyclooctylalanine-NH$_2$. This material was homogenous by HPLC and gave the correct amino acid analysis and MS. Amino acid analysis: Asp 0.92 (1), Gly 1.03 (1), Met 2.26 (2), Tyr 0.95 (1), (2)Nal n.d., and cyclooctylalanine n.d. Empirical formula: C$_{51}$H$_{70}$N$_8$O$_{11}$S$_2$; M.W. 1035.30.

To a suspension of 15 mL unsulfated peptide in 2 mL of dry pyridine, there was added 355 mg of pyridinium acetyl sulfate. The reaction mixture was stirred for 5 hours at room temperature, diluted with 5 mL of 1.5M NH$_4$OH and lyophilized. Purification was achieved by preparative HPLC on an ES Industries C-18 10μ column (1×30) cm using (60 min) of 10 to 50% of 0.01M NH$_4$Ac/CH$_3$CN at a flow rate of 6 mL/min; detection at 290 nm. The main peak was collected and lyophilized to yield 12 mg (75%) of Ac-Tyr(SO$_3$H)-Met-Gly-(2)Nal-Met-Asp-Cyclooctylalanine-NH$_2$ monoammonium salt. This material was homogenous by HPLC and gave the correct amino acid analysis and IR. Empirical formula: C$_{51}$H$_{69}$N$_8$O$_{14}$S$_3$; 1:1 NH$_4^+$; M.W. 1132.39.

EXAMPLE 85

Preparation of Ac-Tyr(SO$_3$H)-Met-Gly-(4-Methoxy)Phe-Met-Asp-Phe-NH$_2$ 1 g of Boc-Phe-PAM resin (substitution 0.58 mmol/g), was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OFm)-OH (1.23 g, 3 mmol), DCC (620 mg, 3 mmol) and HOBt (540 mg, 4 mmol) were dissolved in 40 mL of 1:1 by volume DMF/CH$_2$Cl$_2$, and allowed to couple for 60 min at room temperature. Boc-Met-OH (760 mg, 3 mmol), DCC (760 mg, 3 mmol), DCC (620 mg, 3 mmol) and HOBt (540 mg, 2 mmol) were dissolved in 40 mL of 1:1 by volume DMF/CH$_2$Cl$_2$, and allowed to couple for 60 min at room temperature. Boc-Phe(4-OCH$_3$)-OH (890 mg, 3 mmol), DCC (620 mg, 3 mmol) and HOBt (540 mg, 4 mmol) were dissolved in 40 mL of DMF and allowed to couple for 60 min at room temperature. Boc-Gly-OH (540 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Met-OH (760 mg, 3 mmol), DCC (620 mg, 3 mmol) and HOBt (540 mg, 4 mmol) were dissolved in 40 mL of DMF/CH$_2$Cl$_2$ and allowed to couple for 60 min at room temperature. Boc-Tyr-OH (840 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature.

Deprotection of the Boc-protecting group and acetylation of the resin with 20 mL of acetic anhydride, 10 mL of pyridine in methylene chloride for 120 min yielded 1.5 g of Ac-Tyr-Met-Gly-Phe(4-OCH$_3$)-Met-Asp(OFm)-PAM resin. This resin was treated with 20% perperidine/DMF (step 1-16) using the Fmoc-protocol to yield Ac-Tyr-Met-Gly-Phe(4-OCH$_3$)-Met-Asp-Phe-PAM resin. This peptideyl-PAM resin was then placed in a pressure bottle, suspended in 100 mL of methanol saturated with NH$_3$ at −20° C. and sealed. The suspension was stirred at room temperature for 4 days. After venting the excess NH$_3$, the PAM-resin was filtered off and washed with methanol. The combined filtrates were evaporated to dryness to give 500 mg of crude peptide.

100 mg of the crude peptide was purified by preparative HPLC on a (2.3×30) cm micro Bondapack C-18 column. The peptide was eluted with a linear gradient (4 h) of 5 65% 0.022% TFA/CH$_3$CN at a flow rate of 8 mL/min; detection at 280 nm. The main peak was collected and lyophilized to yield 36 mg (36%) of Ac-Tyr-Met-Gly-Phe(4-OCH$_3$)-Met-Asp-Phe-NH$_2$. This material was homogenous by HPLC and gave the correct amino acid analysis and MS. Amino acid analysis: Asp 1.00 (1); Gly 1.00 (1); Met 1.35 (2); Tyr 1.21 (1); Phe 1.00 (1); Phe(4-OCH$_3$) 0.82 (1). Empirical formula: C$_{46}$H$_{60}$N$_8$O$_{12}$S$_2$ MW 981.16.

To a suspension of 30 mg unsulfated peptide in 3 mL of dry pyridine, there was added 420 mg of pyridinium acetyl sulfate. The reaction mixture was stirred for 6 hours at room temperature, diluted with 10 mL of 1.5M NH$_4$OH and lyophilized. Purification was achieved by preparative HPLC on an ES Industries C-18 10 m column (1×30) cm using a linear gradient 20 to 50% (over 60 min) of 0.01M NH$_4$Ac/CH$_3$CN at a flow rate of 6 mL/min; detection at 290 nm. The main peak was collected and lyophilized to yield 13 mg (40%) of Ac-Tyr(SO$_3$H)-Met-Gly-Phe(4-OCH$_3$)-Met-Asp-Phe-NH$_2$ monoammonium salt. This material was homogenous by HPLC and gave the correct amino acid analysis and IR. Empirical formula: C$_{46}$H$_{59}$N$_8$O$_{15}$S$_3$ 1:1 NH$_4^+$ MW 1028.26.

EXAMPLE 86

Preparation of Ac-Tyr(SO$_3$H)-Met-Gly-(3-Methyl)Phe-Met-Asp-Phe-NH$_2$ 1 g (0.41 mmol) of Boc-Phe-BHA resin, prepared as in Example 70 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Phe(3-CH$_3$)-OH (430 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol) DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of acid anahydride, 10 mL of pyridine in methylene chloride for 60 min yielded of Ac-Tyr-(2,6-dichlorobenzyl)-Met-Gly-Phe(3-CH$_3$)-Met-Asp(OBzl)-Phe-BHA resin. 1.54 g of the resin was cleaved with 9 mL of HF containing 4 mL of anisole 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, triturated with 4×20 mL of 30% acetic acid, filtered and lyophilized to yield 310 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 26 mg (20%) of Ac-Tyr-Met-Gly-Phe(3-CH$_3$)-Met-Asp-Phe-NH$_2$. This material was homogenous by HPLC and gave the correct amino acid analysis and MS. Amino acid analysis: Asp 1.00 (1); Gly 1.03 (1); Met 1.98 (2); Tyr 1.00 (1); Phe 0.96 (1); 3-methylphape 1.03 (1). Empirical formula: C$_{46}$H$_{60}$N$_8$O$_{11}$S$_2$ MW 965.16.

To a suspension of 25 mg unsulfated peptide in 2 mL of dry pyridine, there was added 335 mg of pyridinium acetyl sulfate. The reaction mixture was stirred for 5 hours at room temperature, diluted with 5 mL of 1.5M NH$_4$OH and lyophilized. Purification was achieved by preparative HPLC on an ES Industries C-18 10 m column (1×30) cm using (60 min) of 10 to 50% of 0.01M NH$_4$Ac/CH$_3$CN at a flow rate of 6 mL/min; detection at 290 nm. The main peak was collected and lyophilized to yield 8 mg (30%) of Ac-Tyr(SO$_3$H)-Met-Gly-Phe(3-CH$_3$)-Met-Asp-Phe-NH$_2$ monoammonium salt. This material was homogenous by HPLC and gave the correct amino acid analysis and IR. Empirical formula: C$_{46}$H$_{59}$N$_8$O$_{14}$S$_3$ 1:1 NH$_4$ MW 1062.24.

EXAMPLE 87

Preparation of Ac-Tyr(SO$_3$H)-Met-Gly-(4-Methyl)Phe-Met-Asp-Phe-NH$_2$ 1 g (0.41 mmol) of Boc-Phe-BHA-resin, prepared as in Example 70 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Phe(4-CH$_3$)-OH (430 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol) DCC (310 mg, 1.5 mmol) and HOBt (270 mg, 2 mmol) were dissolved in 20 mL of 1:1 by volume DMF/CH₂Cl₂ and allowed to couple for 60 min at room temperature.

Deprotection of the Boc-protecting group and acetylation of the resin with 10 mL of acetic anhydride, 10 mL of pyridine in methylene chloride for 60 min yielded of Ac-Tyr-(2,6-dichlorobenzyl)-Met-Gly-Phe(4-CH₃)-Met-Asp(OBzl)-Phe-BHA resin. 1.54 g of the resin was cleaved with 9 mL of HF containing 4 mL of anisole 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, triturated with 4×20 mL of 30% acetic acid, filtered and lyophilized to yield 410 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH₃CN at a flow rate of 8 mL/min; detection at 280 nm. The main peak was collected and lyophilized to yield 22 mg (23%) of Ac-Tyr-Met-Gly-Phe(4-CH₃)-Met-Asp-Phe-NH₂. This material was homogenous by HPLC and gave the correct amino acid analysis and MS. Amino acid analysis: Asp 1.00 (1); Gly 1.03 (1); Met 1.98 (2); Tyr 0.92 (1); Phe 1.01 (1); (4-Methyl)phe 0.92 (1). Trp 0.81 (1). Empirical formula: C₄₆H₆₀N₈O₁₁S₂ MW 965.16.

To a suspension of 20 mg unsulfated peptide in 2 mL of dry pyridine, there was added 355 mg of pyridinium acetyl sulfate. The reaction mixture was stirred for 5 hours at room temperature, diluted with 5 mL of 1.5M NH₄OH and lyophilized. Purification was achieved by preparative HPLC on an ES Industries C-18 10 m column (1×30) cm using (60 min) of 10 to 50% of 0.01M NH₄Ac/CH₃CN at a flow rate of 6 mL/min; detection at 290 nm. The main peak was collected and lyophilized to yield 10 mg (48%) of Ac-Tyr(SO₃H)-Met-Gly-Phe(4-CH₃)-Met-Asp-Phe-NH₂ monoammonium salt. This material was homogenous by HPLC and gave the correct amino acid analysis and IR. Empirical formula: C₄₆H₅₉N₈O₁₄S₃ 1:1 NH₄⁺ MW 1062.24.

EXAMPLE 88

Preparation of Ac-Tyr(SO₃H)-Met-Gly-(4-Bromo)Phe-Met-Asp-Phe-NH₂

1 g (0.41 mmol) of Boc-Phe-BHA-resin, prepared as in Example 70 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), DCC (310 mg, 1.5 mmol) and HOBt (270 mg, 2 mmol) were dissolved in 20 mL of 1:1 by volume DMF/CH₂Cl₂, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH₂Cl₂ and allowed to couple for 60 min at room temperature. Boc-Phe(4-Br)-OH (518 mg, 1.5 mmol), DCC (310 mg, 1.5 mmol) and HOBt (270 mg, 2 mmol) were dissolved in 20 mL of 1:1 by volume DMF/CH₂Cl₂ and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH₂Cl₂ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH₂Cl₂ and allowed to couple for 60 min at room temperature. Boc-2,6-dichlorobenzyl-tyrosine (660 mg, 1.5 mmol) DCC (310 mg, 1.5 mmol) and HOBt (270 mg, 2 mmol) were dissolved in 20 mL of 1:1 by volume DMF/CH₂Cl₂ and allowed to couple for 60 min at room temperature.

Deprotection of the Boc-protecting group and acetylation of the resin with 10 mL of acetic anhydride, 10 mL of pyridine in methylene chloride for 60 min yielded of Ac-Tyr-(2,6-dichlorobenzyl)-Met-Gly-Phe(4-Br)-Met-Asp(OBzl)-Phe-BHA resin. 1.6 g of the resin was cleaved with 9 mL of HF containing 4 mL of anisole 1.0 mL of EDT and 25 mL of dimethylsulfide for 1 h at 0° C. After evaporation to a low volume, fresh anhydrous HF (32 mL) was distilled into the reaction vessel for a second treatment for 2 h at 0° C. After thorough evaporation, the resin was washed with 2 volumes of ethylacetate, triturated with 4×20 mL of 30% acetic acid, filtered and lyophilized to yield 440 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH₃CN at a flow rate of 8 mL/min; detection at 280 nm. The main peak was collected and lyophilized to yield 24 mg (25%) of Ac-Tyr-Met-Gly-Phe(4-Br)-Met-Asp-Phe-NH₂. This material was homogenous by HPLC and gave the correct amino acid analysis and MS. Amino acid analysis: Asp 1.00 (1); Gly 0.95 (1); Met 1.80 (2); Tyr 0.98 (1); Phe 1.00 (1); (4-Br)Phe 1.10 (1). Empirical formula: C₄₅H₅₇BrN₈O₁₁S₂ MW 1030.02.

To a suspension of 20 mg unsulfated peptide in 2 mL of dry pyridine, there was added 355 mg of pyridinium acetyl sulfate. The reaction mixture was stirred for 5 hours at room temperature, diluted with 5 mL of 1.5M NH₄OH and lyophilized. Purification was achieved by preparative HPLC on an ES Industries C-18 10 m column (1×30) cm using (60 min) of 10 to 50% of 0.01M NH₄Ac/CH₃CN at a flow rate of 6 mL/min; detection at 290 nm. The main peak was collected and lyophilized to yield 11 mg (50%) of Ac-Tyr(SO₃H)-Met-Gly-Phe(4-Br)-Met-Asp-Phe-NH₂ monoammonium salt. This material was homogenous by HPLC and gave the correct amino acid analysis and IR. Empirical formula: C₄₅H₅₆BrN₈O₁₄S₃ 1:1 NH₄⁺ MW 1127.24.

EXAMPLE 89

Preparation of Ac-Tyr(SO₃H)-Met-Gly-(4-Propyl)Phe-Met-Asp-Phe-NH₂

1 g of Boc-Phe-PAM-resin (substitution 0.58 mmol/g), was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp-(OFm)-OH (123 g, 3 mmol), DCC (620 mg, 3 mmol) and HOBt (540 mg, 4 mmol) were dissolved in 40 mL of 1:1 by volume DMF/CH₂Cl₂, and allowed to couple for 60 min at room temperature. Boc-Met-OH (760 mg, 3 mmol), DCC (620 mg, 3 mmol) and HOBt (540 mg, 2 mmol) were dissolved in 40 mL of 1:1 by volume DMF/CH$_2$Cl$_2$ and allowed to couple for 60 min at room temperature. Boc-Phe(4-CH$_2$CH$_2$CH$_3$)-OH (981 mg, 3 mmol), DCC (620 mg, 3 mmol) and HOBt (540 mg, 4 mmol) were dissolved in 40 mL of DMF, and allowed to couple for 60 min at room temperature. Boc-Gly-OH (540 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Met-OH (700 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Tyr-OH (840 mg, 3 mmol) DCC (620 mg, 3 mmol) and HOBt (540 mg, 4 mmol) were dissolved in 40 mL of 1:1 by volume DMF/CH$_2$Cl$_2$ and allowed to couple for 60 min at room temperature.

Deprotection of the Boc-protecting group and acetylation of the resin with 20 mL of acetic anhydride, 10 mL of pyridine in methylene chloride for 120 min yielded of 1.8 g of Ac-Tyr-Met-Gly-Phe(4-CH$_2$CH$_2$CH$_3$)-Met-Asp(OFm)-Phe resin. This resin was treated with 20% piperidine/DMF (step 1-16) using the Fmoc-protocol to yield Ac-Tyr-Met-Gly-Phe(4-CH$_2$CH$_2$CH$_3$)-Met-Asp-Phe-PAM resin. The peptideyl-PAM resin was then placed in a pressure bottle, suspended in 100 mL of methanol saturated with NH$_3$ at $-20°$ C. and sealed. The suspension was stirred at room temperature for 4 days. After venting the excess NH$_3$, the PAM-resin was filtered off and washed with methanol. The combined filtrates were evaporated to dryness to give 550 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 33 mg of Ac-Tyr-Met-Gly-Phe(4-CH$_2$CH$_2$CH$_3$)-Met-Asp-Phe-NH$_2$. This material was homogenous by HPLC and gave the correct amino acid analysis and MS. Amino acid analysis: Asp 0.38 (1); Gly 1.75 (1); Met 1.90 (2); Tyr 1.00 (1); Phe 1.00 (1); (4-CH$_2$CH$_2$CH$_3$)Phe 0.96 (1). Empirical formula: C$_{48}$H$_{64}$N$_8$O$_{11}$S$_2$ MW 993.22.

To a suspension of 30 mg unsulfated peptide in 3 mL of dry pyridine, there was added 420 mg of pyridinium acetyl sulfate. The reaction mixture was stirred for 6 hours at room temperature, diluted with 10 mL of 1.5M NH$_4$OH and lyophilized. Purification was achieved by preparative HPLC on an ES Industries C-18 10 m column (1×30) cm using a linear gradient 20 to 50% (over 60 min) of 0.01M NH$_4$Ac/CH$_3$CN at a flow rate of 6 mL/min; detection at 290 nm. The main peak was collected and lyophilized to yield 22 mg of Ac-Tyr(-SO$_3$H)-Met-Gly-Phe(4-CH$_2$CH$_2$CH$_3$)-Met-Asp-Phe-NH$_2$ monoammonium salt. This material was homogenous by HPLC and gave the correct amino acid analysis and IR. Empirical formula: C$_{48}$H$_{63}$N$_8$O$_{14}$S$_3$ 1:1 NH$_4{}^+$ MW 1090.31.

EXAMPLE 90

Preparation of Ac-Tyr(SO$_3$H)-Met-Gly-(3-Quinolinyl)alanine-Met-Asp-Phe-NH$_2$ 1 g of Boc-Phe-PAM-resin (substitution 0.58 mmol/g), was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OFm)-OH (1.23 g, 3 mmol), DCC (620 mg, 3 mmol) and HOBt (540 mg, 4 mmol) were dissolved in 40 mL of 1:1 by volume DMF/CH$_2$Cl$_2$, and allowed to couple for 60 min at room temperature. Boc-Met-OH (760 mg, 3 mmol), DCC (620 mg, 3 mmol) and HOBt (540 mg, 2 mmol) were dissolved in 40 mL of 1:1 by volume DMF/CH$_2$Cl$_2$ and allowed to couple for 60 min at room temperature. Boc-Qua-OH ((S)-α-[[(1,1-dimethylethoxy)carbonyl]amino]-3-quinolinepropanoic acid) (960 mg, 3 mmol), DCC (620 mg, 3 mmol) and HOBt (540 mg, 4 mmol) were dissolved in 40 mL of DMF, and allowed to couple for 60 min at room temperature. Boc-Gly-OH (540 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Met-OH (760 mg, 3 mmol), DCC (620 mg, 3 mmol) and HOBt (540 mg, 4 mmol) were dissolved in 40 mL of 1:1 by volume DMF/CH$_2$Cl$_2$ and allowed to couple for 60 min at room temperature. Boc-Tyr-OH (840 mg, 3 mmol) DCC (620 mg, 3 mmol) and HOBt (540 mg, 4 mmol) were dissolved in 40 mL of 1:1 by volume DMF/CH$_2$Cl$_2$ and allowed to couple for 60 min at room temperature.

Deprotection of the Boc-protecting group and acetylation of the resin with 20 mL of acetic anhydride, 10 mL of pyridine in methylene chloride for 120 min yielded of 1.6 g of Ac-Tyr-Met-Gly-Qua-Met-Asp(OFm)-Phe-PAM resin. This resin was treated with 20% piperidine/DMF (step 1-16) using the Fmoc-protocol to yield Ac-Tyr-Met-Gly-Qua-Met-Asp-Phe-PAM resin. The peptideyl-PAM resin was then placed in a pressure bottle, suspended in 100 mL of methanol saturated with NH$_3$ at $-20°$ C. and sealed. The suspension was stirred at room temperature for 4 days. After venting the excess NH$_3$, the PAM-resin was filtered off and washed with methanol. The combined filtrates were evaporated to dryness to give 566 mg of crude peptide.

100 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 20 mg (19%) of Ac-Tyr-Met-Gly-Qua-Met-Asp-Phe-NH$_2$. This material was homogenous by HPLC and gave the correct amino acid analysis and MS. Amino acid analysis: Asp 1.00 (1); Gly 1.00 (1); Met 1.96 (2); Tyr 0.98 (1); Phe 1.00 (1); Qua nd. Empirical formula: C$_{48}$H$_{55}$N$_9$O$_{11}$S$_2$ MW 1002.19.

To a suspension of 20 mg unsulfated peptide in 3 mL of dry pyridine, there was added 420 mg of pyridinium acetyl sulfate. The reaction mixture was stirred for 6 hours at room temperature, diluted with 10 mL of 1.5M NH$_4$OH and lyophilized. Purification was achieved by preparative HPLC on an ES Industries C-18 10 m column (1×30) cm using a linear gradient 20 to 50% (over 60 min) of 0.01M NH$_4$Ac/CH$_3$CN at a flow rate of 6 mL/min; detection at 290 nm. The main peak was collected and lyophilized to yield 8 mg (38%) of Ac-Tyr(-SO$_3$H)-Met-Gly-Qua-Met-Asp-Phe-NH$_2$ monoammonium salt. This material was homogenous by HPLC and gave the correct amino acid analysis and IR. Empirical formula: C$_{49}$H$_{54}$N$_9$O$_{14}$S$_3$ 1:1 NH$_4{}^+$ MW 1035.31.

EXAMPLE 91

Preparation of
Ac-Tyr(SO$_3$H)-Met-Gly-(5,6,7,8-Tetrahydro-2-naphthyl)alanine-Met-Asp-Phe-NH$_2$ 1 g (0.41 mmol) of Boc-Phe-PAM-resin, prepared as in Example 70 was subjected to sequential solid phase synthesis using the Boc-protocol. All couplings were performed using the DCC/HOBt procedure. At step 16 the Boc-amino acid, DCC and HOBt were added with the corresponding reaction times as follows: Boc-Asp(OBzl)-OH (485 mg, 1.5 mmol), and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.83 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Tna-OH ((S)-α-[[(1,1-dimethylethoxy)carbonyl]amino]-5,6,7,8-tetrahydro-2-naphthalenepropanoic acid) (560 mg, 1.5 mmol), DCC (310 mg, 1.5 mmol) and HOBt (270 mg, 2 mmol) were dissolved in 20 mL of 1:1 by volume DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol) DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded Ac-Tyr-(2,6-dichlorobenzyl)-Met-Gly-Tna-Met-Asp(OBzl)-Phe-BHA resin, 1.54 g of the resin was cleaved with 9 mL of HF containing 4 ml of anisole, 1.0 mL of EDT and 25 mL of dimethylsulfide for 1 h at 0° C. After evaporation to a lower volume, fresh anhydrous HF (32 mL) was distilled into the reaction vessel for a second treatment for 2 h at 0° C. After thorough evaporation the resin was washed with 2 volumes of ethylacetate, triturated with 4×20 mL of 30% acetic acid, filtered and lyophilized to yield 460 mg of crude peptide. 230 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 25 mg (12%) of Ac-Tyr-Met-Gly-Tna-Met-Asp-Phe-NH$_2$. This material was homogenous by HPLC and gave the correct amino acid analysis and MS. Amino acid analysis: Asp 1.01 (1); Gly 1.02 (1); Met 1.96 (2); Tyr 0.98 (1); Phe 1.00 (1); Tna n.d. Empirical formula: C$_{49}$H$_{64}$N$_8$O$_{11}$S$_2$ MW 1005.2.

To a suspension of 20 mg unsulfated peptide in 2 mL of dry pyridine, there was added 355 mg of pyridinium acetyl sulfate. The reaction mixture was stirred for 5 hours at room temperature, diluted with 5 mL of 1.5M NH$_4$OH and lyophilized. Purification was achieved by preparative HPLC on an ES Industries C-18 10 m column (1×30) cm using (60 min) of 10 to 50% of 0.01M NH$_4$Ac/CH$_3$CN at a flow rate of 6 mL/min; detection at 290 nm. The main peak was collected and lyophilized to yield 11 mg (50%) of Ac-Tyr(SO$_3$H)-Met-Gly-Tna-Met-Asp-Phe-NH$_2$ monoammonium salt. This material was homogenous by HPLC and gave the correct amino acid analysis and IR. Empirical formula: C$_{49}$H$_{63}$N$_8$O$_{14}$S$_3$ 1:1 NH$_4$ MW 1102.3.

EXAMPLE 92

Preparation of
Ac-Tyr(SO$_3$H)-Met-Gly-Trp-Met-Asp-(5,6,7,8-Tetrahydro-2-naphthyl)alanine-NH$_2$ Boc-Tna-OH ((S)-α-[[(1,1-dimethylethoxy)carbonyl]amino]-5,6,7,8-tetrahydro-2-naphthalenepropanoic acid) (640 mg, 2 mmol) and HOBt (405 mg, 3 mmol) were dissolved in a mixture of 20 mL CH$_2$Cl$_2$ and 20 mL DMF chilled to 0° C. and with stirring (412 mg, 2 mmol) DCC was added and the mixture was stirred for 60 minutes at 0° C. Separately 1 g of benzhydrylamine copolysterne 1% divinylbenzene cross-linked resin (0.41 mmol N/g) was washed with 10% diisopropylethylamine in methylene chloride for 30 min, filtered and washed with methylene chloride dimethylformamide and methlene chloride. The chilled mixture above was added to the resin and stirred for 24 hours at room temperature. The resin was filtered and washed with methylene chloride, dimethylformamide, isopropanol, methylene chloride and dried under high vacuum. Amino acid analysis showed the resin to contain 0.41 mmoles of Tna per gram of resin.

1 g (0.41 mmol) Boc-Tna-BHA resin was then subjected to sequential solid phase synthesis using the Boc protocol. All couplings were performed using the DCC/HOBt procedure. At step 16 the Boc-amino acid, DCC and HOBt, were added with the corresponding reaction times as follows: Boc-Asp-(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol) DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyl-tyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.5 g of Ac-Tyr-(2,6-dichlorobenzyl)-Met-Gly-Rna-Met-Asp(OBzl)-Tna-BHA resin, 1.6 g of the resin was cleaved by treatment with 7 mL of HF containing 3 ml of anisole, 1.0 mL of EDT and 20 mL of dimethylsulfide for 1 h at 0° C. After evaporation to a lower volume, fresh anhydrous HF (28 mL) was distilled into the reaction vessel for a second treatment for 2 h at 0° C. After thorough evaporation the resin was washed with 2 volumes of ethylacetate, triturated with 4×20 mL of 30% acetic acid, filtered and lyophilized to yield 540 mg of crude peptide.

180 mg of the crude peptide was purified by preparative HPLC on a (2.3×30) cm micro Bondapack C-18 column. The peptide was eluted with a linear gradient (4 h) of 5 to 65% 0.022% TFA/CH$_3$CN at a flow rate of 8 mL/min; detection at 280 nm. The main peak was collected and lyophilized to yield 22 mg (15%) of Ac-Tyr-Met-Gly-Trp-Met-Asp-Tna-NH$_2$. This material was homogenous by HPLC and gave the correct amino acid analysis and MS. Amino acid analysis: Asp 1.00 (1), Gly 1.00 (1), Met 1.86 (2): Tyr 0.96 (1); Trp 0.71 (1); Tna n.d. Empirical formula: C$_{51}$H$_{65}$N$_9$O$_{11}$S$_2$ MW 1044.2.

To a suspension of 20 mg unsulfated peptide in 3 mL of dry pyridine, there was added 240 mg of pyridinium acetyl sulfate. The reaction mixture was stirred for 18 hours at room temperature, then diluted with 5 mL of 1.5M NH$_4$OH and lyophilized. Purification was achieved by preparative HPLC on an ES Industries C-18 10 m column (1×30) cm using a linear gradient (60 min) of 10 to 40% of 0.01M NH$_4$Ac/CH$_3$CN at a flow rate of 6 mL/min; detection at 290 nm. The main peak was collected and lyophilized to yield 11 mg (50%) of Ac-Tyr(SO$_3$H)-Met-Gly-Trp-Met-Asp-Tna-NH$_2$ monoammonium salt. This material was homogenous by HPLC, gave the correct amino acid analysis and IR. Empirical formula: C$_{51}$H$_{64}$N$_9$O$_{14}$S$_3$ 1:1 NH$_4^+$ MW 1141.20.

EXAMPLE 93

Preparation of
Ac-Tyr(SO$_3$H)-Met-Gly-Trp-Met-Asp-Dodecylalanine-NH$_2$

Boc-Doa-OH ((S)-α-[[(1,1-dimethylethoxy)carbonyl]amino]tetradecanoic acid) (720 mg, 2 mmol) and HOBt (405 mg, 3 mmol) were dissolved in a mixture of 20 mL CH$_2$Cl$_2$ and 20 mL DMF chilled to 0° C. and with stirring (412 mg, 2 mmol) DCC was added and the mixture was stirred for 60 minutes at 0° C. Separately 1 g of benzhydrylamine copolysterne 1% divinylbenzene cross-linked resin (0.41 mmol N/g) was washed with 10% diisopropylethylamine in methylene chloride for 30 min, filtered and washed with methylene chloride dimethylformamide and methlene chloride. The chilled mixture above was added to the resin and stirred for 24 hours at room temperature. The resin was filtered and washed with methylene chloride, dimethylformamide, isopropanol, methylene chloride and dried under high vacuum. Amino acid analysis showed the resin to contain 0.41 mmoles of Doa per gram of resin.

1 g (0.41 mmol) Boc-Doa-BHA resin was then subjected to sequential solid phase synthesis using the Boc protocol. All couplings were performed using the DCC/HOBt procedure. At step 16 the Boc-amino acid, DCC and HOBt, were added with the corresponding reaction times as follows: Boc-Asp-(OBzl)-OH (485 mg, 1.5 mmol), DCC (310 mg, 1.5 mmol) and HOBt (270 mg, 2 mmol) were dissolved in 20 mL of 1:1 by volume DMF/CH$_2$Cl$_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume DMF/CH$_2$Cl$_2$ and allowed to couple for 60 min at room temperature. Boc-2,6-dichlorobenzyltyrosine (660 mg, 1.5 mmol), DCC (310 lmg, 1.5 mmol) and HOBt (270 mg, 2 mmol) were dissolved in 20 mL of 1:1 by volume DMF/CH$_2$Cl$_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.5 g of Ac-Tyr(2,6-dichlorobenzyl)-Met-Gly-Trp(For)-Met-Asp(OBzl)-Doa BHA resin, 1.5 g of the resin was cleaved by treatment with 7 mL of HF containing 3 mL of anisole, 1.0 mL of EDT and 20 mL of dimethylsulfide for 1 h at 0° C. After evaporation, the resin was washed with 2 volumes of ethylacetate, then triturated with 4×20 mL of 30% acetic acid, filtered and lyophilized to yield 150 mg of crude peptide. 150 mg of the crude peptide was purified by preparative HPLC on a (2.3×30) cm micro Bondapack C-18 column. The peptide was eluted with a linear gradient (4 h) of 20 to 80% 0.022% TFA/CH$_3$CN at a flow rate of 8 mL/min; detection at 280 nm. The main peak was collected and lyophilized to yield 8 mg (2%) of Ac-Tyr-Met-Gly-Trp-Met-Asp-Doa-NH$_2$. This material was homogenous by HPLC and gave the correct amino acid analysis and MS. Amino acid analysis: Asp 1.00 (1), Gly 1.00 (1), Met 1.60 (2): Tyr 1.00 (1); Trp 0.90/(1); Dodec/labrine n.d. Empirical formula: C$_{52}$H$_{77}$N$_9$O$_{11}$S$_2$ MW 1068.40.

To a suspension of 8 mg unsulfated peptide in 3 mL of dry pyridine, there was added 240 mg of pyridinium acetyl sulfate. The reaction mixture was stirred for 18 hours at room temperature, then diluted with 5 mL of 1.5M NH$_4$OH and lyophilized. Purification was achieved by preparative HPLC on an ES Industries C-18 10 m column (1×30) cm using a linear gradient (60 min) of 10 to 40% of 0.01M NH$_4$Ac/CH$_3$CN at a flow rate of 6 mL/min; detection at 290 nm. The main peak was collected and lyophilized to yield 4 mg (45%) of Ac-Tyr(SO$_3$H)-Met-Gly-Trp-Met-Asp-Doa-NH$_2$ monoammonium salt. This material was homogenous by HPLC, gave the correct amino acid analysis and IR. Empirical formula: C$_{52}$H$_{76}$N$_9$O$_{14}$S$_3$ 1:1 NH$_4^+$ MW 1165.4.

EXAMPLE 94

Preparation of
Ac-Tyr(SO$_3$H)-Met-Gly-Trp-Met-Asp-trans-[4-(1,1-Dimethylethyl)cyclohexyl]alanine-NH$_2$ Boc-(4-t-Butyl)Cha-OH trans-(S)-α-[[(1,1-dimethylethoxy)carbonyl]amino)]-4-(1,1-dimethylethyl)cyclohexanepropanoic acid(660 mg, 2 mmol) and HOBt (405 mg, 3 mmol) were dissolved in a mixture of 20 mL $CH_2Cl_2$ and 20 mL DMF chilled to 0° C. and with stirring (412 mg, 2 mmol) DCC was added and the mixture was stirred for 60 minutes at 0° C. Separately 1 g of benzhydrylamine copolysterne 1% divinylbenzene cross-linked resin (0.41 mmol N/g) was washed with 10% diisopropylethylamine in methylene chloride for 30 min, filtered and washed with methylene chloride dimethylformamide and methlene chloride. The chilled mixture above was added to the resin and stirred for 24 hours at room temperature. The resin was filtered and washed with methylene chloride, dimethylformamide, isopropanol, methylene chloride, dimethylformamide, isopropanol, methylene chloride and dried under high vacuum. Amino acid analysis showed the resin to contain 0.41 mmoles of (tert-butyl)alanine per gram of resin.

1 g (0.41 mmol) Boc-(4-t-butyl)Cha-BHA resin was then subjected to sequential solid phase synthesis using the Boc protocol. All couplings were performed using the DCC/HOBt procedure. At step 16 the Boc-amino acid, DCC and HOBt, were added with the corresponding reaction times as follows: Boc-Asp-(OBzl)-OH (485 mg, 1.5 mmol), DCC (310 mg, 1.5 mmol) and HOBt (270 mg, 2 mmol) were dissolved in 20 mL of 1:1 by volume $DMF/CH_2Cl_2$, and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Trp(For)-OH (500 mg, 1.5 mmol), DCC (310 mg, 1.5 mmol) and HOBt (270 mg, 2 mmol) were dissolved in 20 mL of DMF, and allowed to couple for 60 min at room temperature. Boc-Gly-OH (270 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-Met-OH (380 mg, 1.5 mmol), DCC (310 mg, 1.5 mmol) and HOBt (270 mg, 2 mmol) were dissolved in 20 mL of 1:1 by volume $DMF/CH_2Cl_2$ and allowed to couple for 60 min at room temperature. Boc-2,6-dichlorobenzyltyrosine (660 mg, 1.5 mmol), DCC (310 lmg, 1.5 mmol) and HOBt (270 mg, 2 mmol) were dissolved in 20 mL of 1:1 by volume $DMF/CH_2Cl_2$ and allowed to couple for 60 min at room temperature.

Deprotection of the Boc-protecting group and acetylation of the resin with 10 mL of acetic anhydride, 10 mL of pyridine in methylene chloride for 60 min yielded 1.5 g of Ac-Tyr(2,6-dichlorobenzyl)-Met-Gly-Trp(For)-Met-Asp(OBzl)-(4-t-Butyl)Cha-BHA resin, 1.5 g of the resin was cleaved by treatment with 7 mL of HF containing 3 mL of anisole, 1.0 mL of EDT and 20 mL of dimethylsulfide for 1 h at 0° C. After evaporation, the resin was washed with 2 volumes of ethylacetate, then triturated with 4×20 mL of 30% acetic acid, filtered and lyophilized to yield 306 mg of crude peptide. 100 mg of the crude peptide was purified by preparative HPLC on a (2.3×30) cm micro Bondapack C-18 column. The peptide was eluted with a linear gradient (4 h) of 5 to 65% 0.022% $TFA/CH_3CN$ at a flow rate of 8 mL/min; detection at 280 nm. The main peak was collected and lyophilized to yield 8 mg (6%) of Ac-Tyr-Met-Gly-Trp-Met-Asp-Cha(4-tBu)-$NH_2$. This material was homogenous by HPLC and gave the correct amino acid analysis and MS. Amino acid analysis: Asp 1.00 (1), Gly 1.00 (1), Met 2.01 (2): Tyr 0.98 (1); Trp n.d. t-Bu-cha n.d. Empirical formula: $C_{51}H_{73}N_9O_{11}S_2$ MW 1052.34.

To a suspension of 8 mg unsulfated peptide in 3 mL of dry pyridine, there was added 200 mg of pyridinium acetyl sulfate. The reaction mixture was stirred for 18 hours at room temperature, then diluted with 5 mL of 1.5M $NH_4OH$ and lyophilized. Purification was achieved by preparative HPLC on an ES Industries C-18 10 m column (1×30) cm using a linear gradient (60 min) of 10 to 40% of 0.01M $NH_4Ac/CH_3CN$ at a flow rate of 6 mL/min; detection at 290 nm. The main peak was collected and lyophilized to yield 4 mg (50%) of Ac-Tyr($SO_3H$)-Met-Gly-Trp-Met-Asp-(4-t-Butyl)Cha-$NH_2$ monoammonium salt. This material was homogenous by HPLC, gave the correct amino acid analysis and IR. Empirical formula: $C_{51}H_{72}N_9O_{14}S_3$ 1:1 $NH_4^+$ MW 1149.43.

EXAMPLE 95

Degradation Studies

Human neutral metalloendopeptidase (0.01 mg) and 5 nmol of peptide were incubated in 2 mmol tris-HCl buffer (pH 7.6) and at 37° C. for varying periods of time. The degradation of the peptide was monitored by analytical HPLC on a 5 micron Adsorbosphere-ODS column with 0–50% $CH_3CN$ gradient in 0.1N potassium phosphate buffer, pH 3.0, with UV detection at 210 nm. Rates are based on presumed production of Asp-Tyr(-$SO_3H$)-Met-Gly for CCK-8 and Ac-Tyr($SO_3H$)-Met-Gly for the compound of example 73.

TABLE 1

Degradation of CCK-8 and the Peptide of Example 73 by Human Metalloendopeptidase

|  | Time of Incubation (min) | % Degradation by Heights | No. of Peaks |
|---|---|---|---|
| CCK-8 | 0 | 0 |  |
|  | 15 | 6.2 |  |
|  | 30 | 33.2 |  |
|  | 60 | 69.7 | 4 |
| Peptide of Example 73 | 0 | 0 |  |
|  | 60 | 10.0 |  |
|  | 120 | 27.0 |  |
|  | 240 | 56.4 | 2* |

*Indicates one peak detected and one peak that co-eluted with substrate that was differentiated based on molar ratios following amino acid analysis.

EXAMPLE 96

Two-Meal Feeding Assay

Male Sprague-Dawley (CD) rats weighing 180–200 grams (Charles River Breeding Laboratories) were acclimated to a 12 h light/dark cycle (6 a.m. to 6 p.m.) in a room kept at 22° C. They were subsequently fasted for two days, weighed, placed in individual cages, and a four-day period of meal training was begun. During this time the rats were given ground laboratory chow (Purina Lab Chow) in jars for one hour from 9:00 a.m. until 10:00 a.m., the jars were removed from 10:00 a.m. to 12:00 p.m., and placed back in the cages from 12:00 until 1:00 p.m. Under this '1-2-1' meal feeding regime, most rats learn to eat approximately as much per day during the two hours they have access to food as rats which have food ad libitum over the entire 24-hour day. On the fourth day, the rats were weighed again, and any which lost more than five grams body weight were excluded from the test. The animals were then distributed into experimental (n=5 to 6) and control groups (n=6-12), but not matched for body weight. Peptides of the invention were suspended either in saline, if soluble, or in 0.5% DMSO/saline, if insoluble, at concentrations of 0 to 320 mg/mL/kg body weight and were administered intraperitoneally 15 min before the first meal on day 5 of meal feeding. The rats were then given their meals as they had been during the previous four days, and the food cups were weighed both before and after each meal to determine food consumption. Food intake was expressed as a mean and standard error of the mean in percent of control values for the various groups. The treated groups were compared to the control groups by t-test analysis. The results are summarized in Table 2.

EXAMPLE 97

In Vitro Receptor Binding Assay

Frozen bovine striatum (approx. 5 g) or fresh rat pancreas (approx. 5 g) cleaned of fat and extraneous tissue were homogenized in HEPES buffer #1 (10 mM HEPES+130 mM NaCl+5 mM MgCl$_2$, pH 7.4) using 35 parts buffer per 1 part tissue on a wet weight/volume basis (approx. 175 mL). The tissue was homogenized 2× for approx. 15 sec. at 0° C. using a Polytron homogenizer at a setting of 6. The tissue was isolated by centrifugation at 48,000×g for 10 min at 0° C. The resulting tissue pellet was resuspended in HEPES buffer #2 (10 mM HEPES+130 mM NaCl+5 mM MgCl$_2$+1 mg/L phenylmethanesulfonyl fluoride (PMSF)+200 mg/L Bacitracin): 1 part striatal tissue (original wet weight) per 80 parts buffer and 1 parts pancreas tissue (original wet weight) per 500 to 1000 parts buffer. Incubation was initiated by combining various concentrations of native CCK-8 or peptides of the invention with $^3$H-CCK-8-(SO$_3$H)(final conc.=0.15 nM) and tissue homogenate (striatum approximately 0.26 mg protein in 2 mL final volume; pancreas approximately 0.100 mg protein in 1 mL final volume). Samples were incubated for 30 min at 25° C. and the incubation terminated by pouring the mixture onto a pre-wetted Whatman GF/B filter on a Sandbeck Vacuum Filtration Manifold. The incubation tubes were washed with 2×3 mL of ice-cold HEPES Buffer #2 and the wash filtered through the GF/B filter. The filter was air dried for 10 min and then placed in a scintillation vial with 12 mL of DuPont/NEN Aquasol scintillation cocktail. The vials were shaken overnight and then counted using a liquid scintillation spectrometer. Non-specific binding was determined in the presence of 1 micromolar native CCK-8 and substracted from all samples to determine specific binding. The concentration of peptide necessary to inhibit 50% of total specific $^3$H-CCK-8-(SO$_3$H) binding (IC$_{50}$ value) was determined by log-probit analysis. The results are summarized in Table 2.

While the invention has been described in connection with the preferred embodiment, it is not intended to limit the scope of the invention to the particular form set forth but, on the contrary, it is intended to cover such alternatives, modifications, and equivalents as may be included within the spirit and scope of the appended claims.

We claim:

1. A compound selected from the group consisting of:

I(a) X-Tyr(SO$_3$H)-Met-Gly-Trp-Met-Asp-R$^1$-NH$_2$

I(b) X-Tyr(SO$_3$H)-Met-Gly-R$^2$-Met-Asp-Phe-NH$_2$

I(c) X-Tyr(SO$_3$H)-Met-Gly-R$^2$-Met-Asp-R$^3$-NH$_2$

I(d) R$^7$-Met-Gly-Trp-Met-Asp-R$^3$-NH$_2$

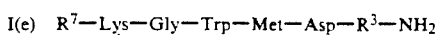

wherein R$^1$ is a radical of the formula:

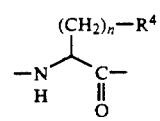

wherein R$^2$ is a radical of the formula:

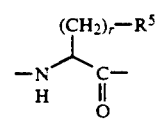

wherein R$^3$ is a radical of the formula

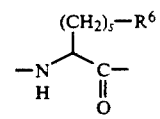

wherein R$^4$ is a substituted or unsubstituted C$_5$ or C$_{7-12}$ mono or polycyclic alkyl where the substitutent is C$_{1-7}$ alkyl; C$_{4-15}$ linear or branched chain alkyl; tetrahydronaphthyl; or naphthyl, R$^5$ is a substituted phenyl where the substituents are selected from the group consisting of C$_{1-7}$ alkyl, C$_{1-7}$ alkoxy, or halogen; benzothiophenyl; quinolinyl; tetrahydronaphthyl; or substituted or unsubstituted naphthyl with the substituents selected from the groups consisting of halogen, C$_{1-7}$ alkyl, or C$_{1-7}$ alkoxy, R$^6$ is a substituted or unsubstituted C$_{5-12}$ mono or polycyclic alkyl where the substitutent is C$_{1-7}$ alkyl; C$_{4-15}$ linear or branched chain alkyl; tetrahydronaphthyl; or substituted or unsubstituted naphthyl with the substituents selected from the groups consisting of halogen, C$_{1-7}$ alkyl, or C$_{1-7}$ alkoxy, R$^7$ is a radical of the formula:

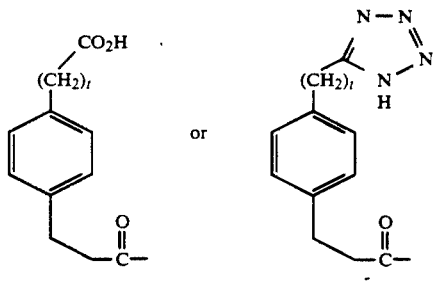

n is an integer from 0-3 r is an integer from 1-3 s is an integer from 1-3 t is an integer from 0-2

X is C$_{1-7}$ alkanoyl or C$_{1-7}$ alkoxy carbonyl.

2. The compound of claim 1 which is I(a).

3. The compound of claim 2 wherein X=Acetyl.

4. The compound of claim 3 wherein $R^4$ is a substituted or unsubstituted cyclopentyl.

5. The compound of claim 4 wherein n=1 said compound having the formula:

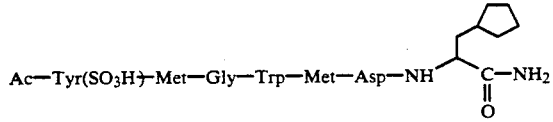

6. The compound of claim 3 wherein $R^4$ is a substituted or unsubstituted $C_{7-12}$ mono or polycyclic alkyl.

7. The compound of claim 6 wherein $R^4$ is cyclooctyl and n=1, said compound having the formula:

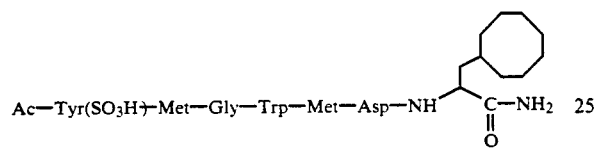

8. The compound of claim 6 wherein $R^4$ is (2-adamantyl) and n=1, said compound having the formula:

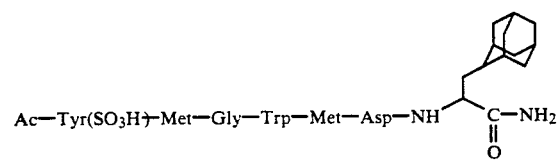

9. The compound of claim 6 wherein $R^4$ is cyclohexyl and n=2, said compound having the formula:

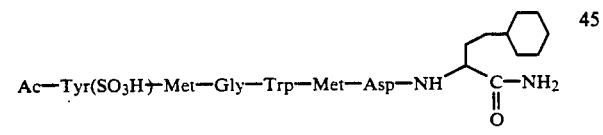

10. The compound of claim 6 wherein $R^4$ is trans-4-t-butylcyclohexyl and n=1, said compound having the formula:

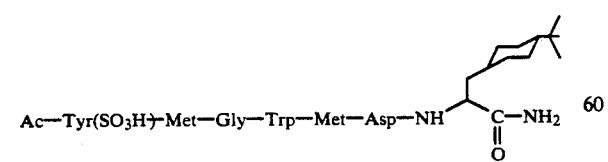

11. The compound of claim 3 wherein $R^4$ is a $C_{4-15}$ linear or branched chain alkyl.

12. The compound of claim 11 wherein $R^4$ is tert.-butyl and n=1, said compound having the formula:

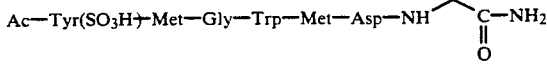

13. The compound of claim 11 wherein $R^4$ is decyl and n=2, said compound having the formula:

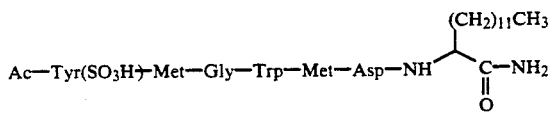

14. The compound of claim 2 wherein $R^4$ is tetrahydronaphthyl.

15. The compound of claim 14 wherein $R^4$ is (5,6,7,8-tetrahydro-2-naphthyl) and n=1, said compound having the formula:

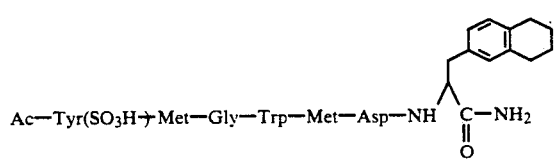

16. The compound of claim 1 which is I(b).

17. The compound of claim 16 wherein X is Acetyl.

18. The compound of claim 17 wherein $R^5$ is a substituted phenyl where the substituents are selected from the group consisting of $C_{1-7}$ alkyl, $C_{1-7}$ alkoxy or halogen.

19. The compound of claim 18 wherein $R^5$ is 4-methylphenyl and r=1, said compound having the formula:

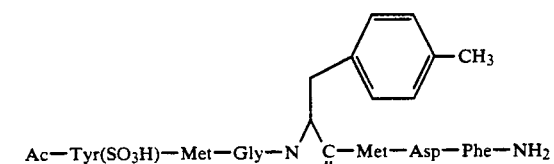

20. The compound of claim 18 wherein $R^5$ is 4-bromophenyl and r=1, said compound having the formula:

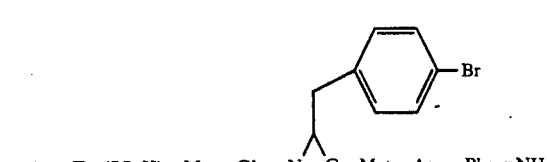

21. The compound of claim 18 wherein $R^5$ is 4-methoxyphenyl and r=1, said compound having the formula:

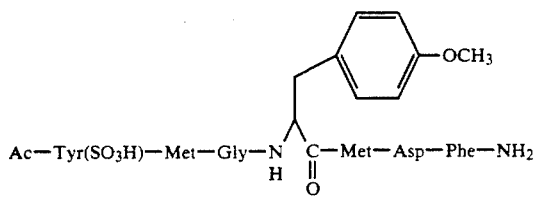

22. The compound of claim 18 wherein $R^5$ is 3-methylphenyl and r=1, said compound having the formula:

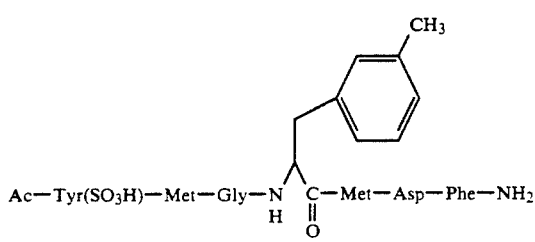

23. The compound of claim 18 wherein $R^5$ is 4-propylphenyl and r=1, said compound having the formula:

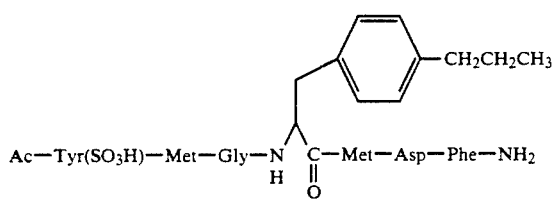

24. The compound of claim 17 wherein $R^5$ is quinolinyl.

25. The compound of claim 24 wherein $R^2$ is 3-quinolinyl and r=1, said compound having the formula:

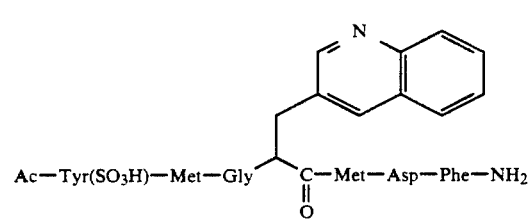

26. The compound of claim 17 wherein $R^5$ is tetrahydronapthyl.

27. The compound of claim 26 wherein $R^5$ is 5,6,7,8-tetrahydro-2-naphthyl and r=1, said compound having the formula:

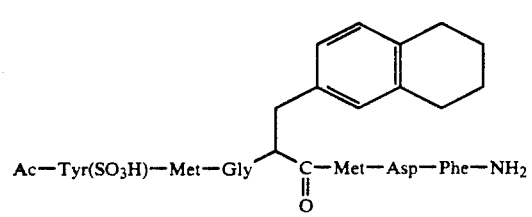

28. The compound of claim 17 wherein $R^5$ is benzothiophenyl.

29. The compound of claim 28 wherein $R^5$ is 2-Benzothiophenyl and r=1, said compound having the formula:

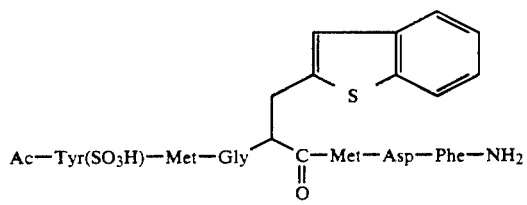

30. The compound of claim 1 which is I(c).

31. The compound of claim 30 wherein X is Acetyl.

32. The compound of claim 31 wherein $R^5$ is a substituted or unsubstituted naphthyl where the substituents are selected from the group consisting of halogen, $C_{1-7}$ alkyl, or $C_{1-7}$ alkoxy.

33. The compound of claim 32 wherein $R^6$ is a substituted or unsubstituted naphthyl with the substituents selected from the group consisting of halogen, $C_{1-7}$ alkyl, or $C_{1-7}$ alkoxy; or a substituted or unsubstituted $C_{5-12}$ mono or polycyclic alkyl where the substitutent is $C_{1-7}$ alkyl; or $C_4$-$C_{12}$ branched or straight chain alkyl.

34. The compound of claim 33 wherein $R^5$ is 2-naphthyl.

35. The compound of claim 33 wherein $R^6$ is a substituted or unsubstituted $C_{5-12}$ mono or polycyclic alkyl where the substitutent is $C_{1-7}$ alkyl.

36. The compound of claim 34 wherein $R^6$ is cyclohexyl and r and s=1, said compound having the formula:

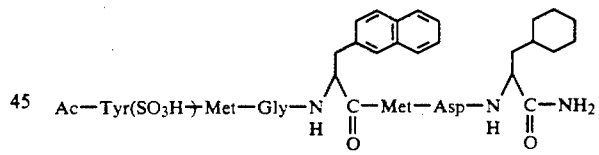

37. The compound of claim 34 wherein $R^6$ is cyclooctyl and r and s=1, said compound having the formula:

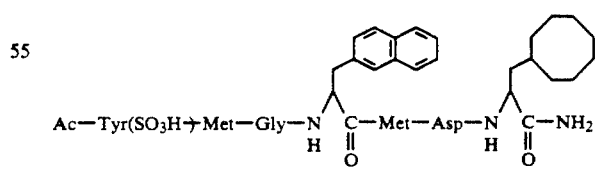

38. The compound of claim 34 wherein $R^6$ is substituted or unsubstituted naphthyl where the substituents are selected from the group consisting of halogen, $C_{1-7}$ alkyl, or $C_{1-7}$ alkoxy.

39. The compound of claim 38 wherein $R^6$ is 2-naphthyl and r and s=1, said compound having the formula:

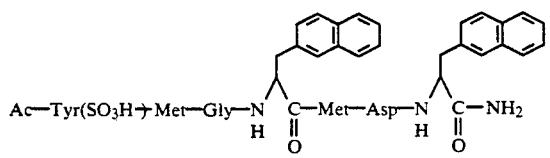

40. The compound of claim 1 which is I(d).

41. The compound of claim 40 wherein $R^7$ is

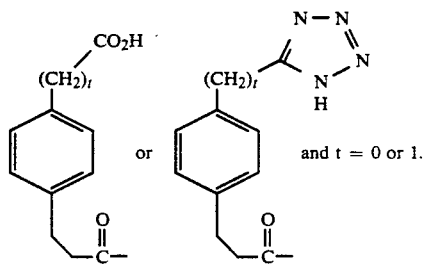

and t = 0 or 1.

42. The compound of claim 41 wherein $R^6$ is a substituted or unsubstituted $C_{5-12}$ mono or polycyclic alkyl where the substitutent is $C_{1-7}$ alkyl.

43. The compound of claim 42 wherein $R^6$ is cyclohexyl or cyclooctyl.

44. The compound of claim 43 wherein $R^6$ is cyclohexyl, s=1 and $R^7$ is

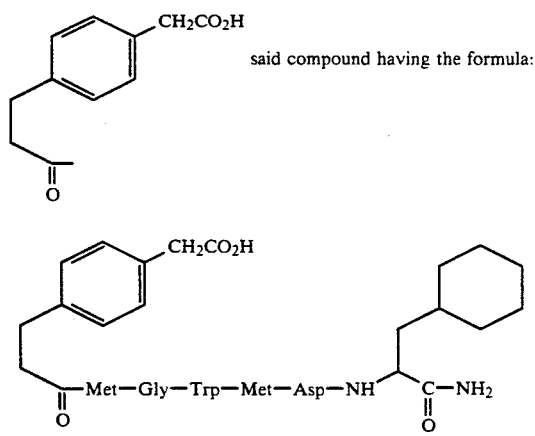

said compound having the formula:

45. The compound of claim 43 wherein $R^6$ is cyclooctyl, s=1 and $R^7$ is

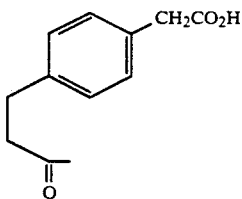

said compound having the formula:

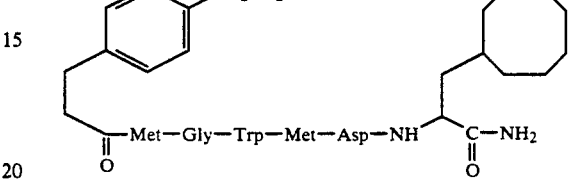

46. The compound of claim 1 which is I(e).

47. The compound of claim 46 wherein $R^6$ is cyclohexyl, s=1, t=0 and $R^7$ is

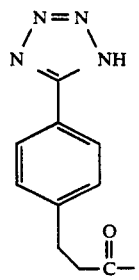

said compound having the formula:

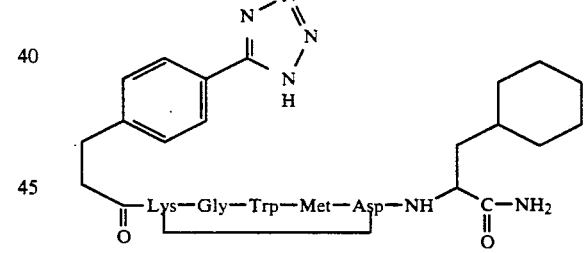

* * * * *